(12) United States Patent
Mancebo et al.

(10) Patent No.: US 7,781,209 B2
(45) Date of Patent: Aug. 24, 2010

(54) GPCR-EXPRESSING CELL LINES

(75) Inventors: Helena S. Mancebo, Fremont, CA (US); Jeng-Horng Her, San Jose, CA (US); Samuel X. Li, Redmond, WA (US); Jianfu L. Wang, Union City, CA (US)

(73) Assignee: Multispan, Inc., Hayward, CA (US)

( * ) Notice: Subject to any disclaimer, the term of this patent is extended or adjusted under 35 U.S.C. 154(b) by 351 days.

(21) Appl. No.: 11/529,826

(22) Filed: Sep. 29, 2006

(65) Prior Publication Data

US 2007/0196867 A1    Aug. 23, 2007

Related U.S. Application Data

(60) Provisional application No. 60/730,997, filed on Oct. 28, 2005, provisional application No. 60/721,845, filed on Sep. 25, 2005.

(51) Int. Cl.
| | |
|---|---|
| *C12N 15/00* | (2006.01) |
| *C12N 1/20* | (2006.01) |
| *C12N 5/00* | (2006.01) |
| *C12N 5/02* | (2006.01) |
| *C12N 15/74* | (2006.01) |
| *C12P 21/06* | (2006.01) |
| *C07K 1/00* | (2006.01) |
| *C07K 14/00* | (2006.01) |
| *C07K 17/00* | (2006.01) |

(52) U.S. Cl. ............... 435/320.1; 435/69.1; 435/252.3; 435/325; 435/471; 530/350

(58) Field of Classification Search ........................ None
See application file for complete search history.

(56) References Cited

U.S. PATENT DOCUMENTS

| | | | |
|---|---|---|---|
| 4,391,904 A | 7/1983 | Litman et al. | |
| 5,283,317 A | 2/1994 | Saifer et al. | |
| 5,288,514 A | 2/1994 | Ellman | |
| 5,506,337 A | 4/1996 | Summerton et al. | |
| 5,519,134 A | 5/1996 | Acevedo et al. | |
| 5,525,735 A | 6/1996 | Gallop et al. | |
| 5,539,083 A | 7/1996 | Cook et al. | |
| 5,549,974 A | 8/1996 | Holmes | |
| 5,569,588 A | 10/1996 | Ashby et al. | |
| 5,593,853 A | 1/1997 | Chen et al. | |
| 5,801,037 A * | 9/1998 | Behnke et al. | 435/220 |
| 5,861,272 A | 1/1999 | Li et al. | |
| 6,852,510 B2 | 2/2005 | Bremel et al. | |
| 2003/0100031 A1 * | 5/2003 | Dower et al. | 435/7.9 |
| 2004/0146907 A1 * | 7/2004 | Smith | 435/6 |

FOREIGN PATENT DOCUMENTS

| | | |
|---|---|---|
| WO | WO 91/19735 | 12/1991 |
| WO | WO 92/00091 | 1/1992 |
| WO | WO 93/20242 | 10/1993 |
| WO | WO 97/00271 | 1/1997 |

OTHER PUBLICATIONS

Altenhofen et al., "Control of ligand specificity in cyclic nucleotide-gated channels from rod photoreceptors and olfactory epithelium," *Proc. Natl. Acad. Sci. USA* (1991) 88:9868-9872.
DeWitt et al., ""Diversomers": An approach to nonpeptide, nonoligomeric chemical diversity," *Proc. Natl. Acad. Sci. USA* (1993) 90:6909-6913.
Weber, "Ion currents of *Xenopus laevis* oocytes: state of the art," *Biochimica et Biophysica Acta* (1999) 1421:213-233.
LabLife, *Vector Database Sequence—pMEX5*, https://www.lablife.org/ct?a=viewvecseq&soid=3314&view=Sequence&f=v, accessed Nov. 17, 2009 (4 pages).
Stanford Molecular Biology Vector Sequence Database, *E. coli phagemid vector pMEX5*, http://genome-www.stanford.edu/vectordb/vector_descrip/PMEX5.html, accessed Nov. 19, 2009 (1 page).

* cited by examiner

*Primary Examiner*—Robert Landsman
(74) *Attorney, Agent, or Firm*—Dorsey & Whitney LLP

(57) ABSTRACT

The present invention provides expression vectors that facilitate high levels of expression of GPCR proteins. Encompassed by the invention are methods and compositions for recombinant cell lines expressing GPCR proteins with the aid of the expression vectors of the instant invention. The recombinant cell lines of the instant invention express GPCR proteins at levels of at least about 150,000 copies of the protein per cell. The present invention also provides methods and compositions for raising antibodies against GPCR proteins using the high expressing recombinant cells of the instant invention.

33 Claims, 24 Drawing Sheets

FIG. 1

SEQUENCE OF G-PROTEIN COUPLED RECEPTOR C5AR

C5AR AMINO ACID SEQUENCE

SEQ ID NO: 1

MNSFNYTTPDYGHYDDKDTLDLNTPVDKTSNTLRVPDILALVIFAVVFLVGVLGNAL
VVWVTAFEAKRTINAIWFLNLAVADFLSCLALPILFTSIVQHHHWPFGGAACSILPSLI
LLNMYASILLLATISADRFLLVFKPIWCQNFRGAGLAWIACAVAWGLALLLTIPSFLY
RVVREEYFPPKVLCGVDYSHDKRRERAVAIVRLVLGFLWPLLTLTICYTFILLRTWSR
RATRSTKTLKVVVAVVASFFIFWLPYQVTGIMMSFLEPSSPTFLLLNKLDSLCVSFAYI
NCCINPIIYVVAGQGFQGRLRKSLPSLLRNVLTEESVVRESKSFTRSTVDTMAQKTQA
V

C5AR NUCLEOTIDE SEQUENCE

SEQ ID NO: 2 atgaactccttcaattataccaccccctgattatgggcactatgatgacaaggataccctggacctcaacaccccctgtggataaaacttcta
acacgctgcgtgttccagacatcctggccttggtcatctttgcagtcgtcttcctggtgggagtgctgggcaatgccctggtggtctgggt
gacggcattcgaggccaagcggaccatcaatgccatctggttcctcaacttggcggtagccgacttcctctcctgcctggcgctgccc
atcttgttcacgtccattgtacagcatcaccactggccctttggcggggccgcctgcagcatcctgccctccctcatcctgctcaacatgt
acgccagcatcctgctcctggccaccatcagcgccgaccgctttctgctggtgtttaaacccatctggtgccagaacttccgaggggcc
ggcttggcctggatcgcctgtgccgtggcttggggtttagccctgctgctgaccatacccctccttcctgtaccgggtggtccgggagga
gtactttccaccaaaggtgttgtgtggcgtggactacagccacgacaaacggcgggagcgagccgtggccatcgtccggctggtcct
gggcttcctgtggcctctactcacgctcacgatttgttacactttcatcctgctccggacgtggagccgcagggccacgcggtccacca
agacactcaaggtggtggtggcagtggtggccagtttctttatcttctggttgccctaccaggtgacggggataatgatgtccttcctgga
gccatcgtcacccaccttcctgctgctgaataagctggactccctgtgtgtctcctttgcctacatcaactgctgcatcaacccccatcatct
acgtggtggccggccaggcttccagggccgactgcggaaatccctccccagcctcctccggaacgtgttgactgaagagtccgtg
gttagggagagcaagtcattcacgcgctccacagtggacactatggcccagaagacccaggcagtgtag

FIG. 2

SEQUENCE OF G-PROTEIN COUPLED RECEPTOR NMUR1

NMUR1 AMINO ACID SEQUENCE

SEQ ID NO: 3

MTPLCLNCSVLPGDLYPGGARNPMACNGSAARGHFDPEDLNLTDEALRLKYLGPQQ
TELFMPICATYLLIFVVGAVGNGLTCLVILRHKAMRTPTNYYLFSLAVSDLLVLLVGL
PLELYEMWHNYPFLLGVGGCYFRTLLFEMVCLASVLNVTALSVERYVAVVHPLQAR
SMVTRAHVRRVLGAVWGLAMLCSLPNTSLHGIQQLHVPCRGPVPDSAVCMLVRPR
ALYNMVVQTTALLFFCLPMAIMSVLYLLIGLRLRRERLLLMQEAKGRGSAAARSRY
TCRLQQHDRGRRQVTKMLFVLVVVFGICWAPFHADRVMWSVVSQWTDGLHLAFQ
HVHVISGIFFYLGSAANPVLYSLMSSRFRETFQEALCLGACCHRLRPRHSSHSLSRMT
TGSTLCDVGSLGSWVHPLAGNDGPEAQQETDPS

NMUR1 NUCLEOTIDE SEQUENCE

SEQ ID NO: 4 atgactcctctctgcctcaattgctctgtcctccctggagacctgtacccaggggggtgcaaggaacccatggcttgcaatggcagtgc
ggccagggggcactttgaccctgaggacttgaacctgactgacgaggcactgagactcaagtacctggggcccagcagacagag
ctgttcatgcccatctgtgccacatacctgctgatcttcgtggtgggcgctgtgggcaatgggctgacctgtctggtcatcctgcgccac
aaggccatgcgcacgcctaccaactactacctcttcagcctggccgtgtcggacctgctggtgctgctggtgggcctgcccctggagc
tctatgagatgtggcacaactacccccttcctgctgggcgttggtggctgctatttccgcacgctactgtttgagatggtctgcctggcctca
gtgctcaacgtcactgccctgagcgtggaacgctatgtggccgtggtgcacccactccaggccaggtccatggtgacgcgggcccat
gtgcgccgagtgcttggggccgtctggggtcttgccatgctctgctccctgcccaacaccagcctgcacggcatccagcagctgcac
gtgccctgccggggcccagtgccagactcagctgtttgcatgctggtccgcccacgggccctctacaacatggtagtgcagaccacc
gcgctgctcttcttctgcctgcccatggccatcatgagcgtgctctacctgctcattgggctgcgactgcggcgggagaggctgctgct
catgcaggaggccaagggcaggggctctgcagcagccaggtccagatacacctgcaggctccagcagcacgatcggggccgga
gacaagtgaccaagatgctgtttgtcctggtcgtggtgtttggcatctgctgggccccgttccacgccgaccgcgtcatgtggagcgtc
gtgtcacagtggacagatggcctgcacctggccttccagcacgtgcacgtcatctccggcatcttcttctacctgggctcggcggccaa
ccccgtgctctatagcctcatgtccagccgcttccgagagaccttccaggaggccctgtgcctcggggcctgctgccatcgcctcaga
ccccgccacagctcccacagcctcagcaggatgaccacaggcagcaccctgtgtgatgtgggctccctgggcagctgggtccaccc
cctggctgggaacgatggcccagaggcgcagcaagagaccgatccatcctga

FIG. 3

SEQUENCE OF G-PROTEIN COUPLED RECEPTOR P2RY2

P2RY2 AMINO ACID SEQUENCE

SEQ ID NO: 5

MAADLGPWNDTINGTWDGDELGYRCRFNEDFKYVLLPVSYGVVCVPGLCLNAVAL
YIFLCRLKTWNASTTYMFHLAVSDALYAASLPLLVYYYARGDHWPFSTVLCKLVRF
LFYTNLYCSILFLTCISVHRCLGVLRPLRSLRWGRARYARRVAGAVWVLVLACQAP
VLYFVTTSARGGRVTCHDTSAPELFSRFVAYSSVMLGLLFAVPFAVILVCYVLMARR
LLKPAYGTSGGLPRAKRKSVRTIAVVLAVFALCFLPFHVTRTLYYSFRSLDLSCHTLN
AINMAYKVTRPLASANSCLDPVLYFLAGQRLVRFARDAKPPTGPSPATPARRRLGLR
RSDRTDMQRIEDVLGSSEDSRRTESTPAGSENTKDIRL

P2RY2 NUCLEOTIDE SEQUENCE

SEQ ID NO: 6 atggcagcagacctgggcccctggaatgacaccatcaatggcacctgggatggggatgagctgggctacaggtgccgcttcaacga
ggacttcaagtacgtgctgctgcctgtgtcctacggcgtggtgtgcgtgcctgggctgtgtctgaacgccgtggcgctctacatcttcttg
tgccgcctcaagacctggaatgcgtccaccacatatatgttccacctggctgtgtctgatgcactgtatgcggcctccctgccgctgctg
gtctattactacgcccgcggcgaccactggcccttcagcacggtgctctgcaagctggtgcgcttcctcttctacaccaacctttactgc
agcatcctcttcctcacctgcatcagcgtgcaccggtgtctgggcgtcttacgacctctgcgctccctgcgctggggccgggcccgcta
cgctcgccgggtggccggggccgtgtgggtgttggtgctggcctgccaggcccccgtgctctactttgtcaccaccagcgcgcgcg
ggggccgcgtaacctgccacgacacctcggcacccgagctcttcagccgcttcgtggcctacagctcagtcatgctgggcctgctctt
cgcggtgccctttgccgtcatccttgtctgttacgtgctcatggctcggcgactgctaaagccagcctacgggacctcggcggcctgc
ctagggccaagcgcaagtccgtgcgcaccatcgccgtggtgctggctgtcttcgccctctgcttcctgccattccacgtcacccgcacc
ctctactactccttccgctcgctggacctcagctgccacaccctcaacgccatcaacatggcctacaaggttacccggccgctggcca
gtgctaacagttgccttgaccccgtgctctacttcctggctgggcagaggctcgtacgctttgcccgagatgccaagccacccactggc
cccagccctgccaccccggctcgccgcaggctgggcctgcgcagatccgacagaactgacatgcagaggatagaagatgtgttgg
gcagcagtgaggactctaggcggacagagtccacgccggctggtagcgagaacactaaggacattcggctgtag

FIG. 4

SEQUENCE OF G-PROTEIN COUPLED RECEPTOR PTAFR

PTAFR AMINO ACID SEQUENCE

SEQ ID NO: 7

MEPHDSSHMDSEFRYTLFPIVYSIIFVLGVIANGYVLWVFARLYPCKKFNEIKIFMVN
LTMADMLFLITLPLWIVYYQNQGNWILPKFLCNVAGCLFFINTYCSVAFLGVITYNRF
QAVTRPIKTAQANTRKRGISLSLVIWVAIVGAASYFLILDSTNTVPDSAGSGNVTRCF
EHYEKGSVPVLIIHIFIVFSFFLVFLIILFCNLVIIRTLLMQPVQQQRNAEVKRRALWMV
CTVLAVFIICFVPHHVVQLPWTLAELGFQDSKFHQAINDAHQVTLCLLSTNCVLDPVI
YCFLTKKFRKHLTEKFYSMRSSRKCSRATTDTVTEVVVPFNQIPGNSLKN

PTAFR NUCLEOTIDE SEQUENCE

SEQ ID NO: 8 atggagccacatgactcctcccacatggactctgagttccgatacactctcttcccgattgtttacagcatcatctttgtgctcggggtcatt
gctaatggctacgtgctgtgggtctttgcccgcctgtacccttgcaagaaattcaatgagataaagatcttcatggtgaacctcaccatgg
cggacatgctcttcttgatcaccctgccactttggattgtctactaccaaaaccagggcaactggatactccccaaattcctgtgcaacgt
ggctggctgccttttcttcatcaacacctactgctctgtggccttcctgggcgtcatcacttataaccgcttccaggcagtaactcggccca
tcaagactgctcaggccaacacccgcaagcgtggcatctctttgtccttggtcatctgggtggccattgtgggagctgcatcctacttcct
catcctggactccaccaacacagtgcccgacagtgctggctcaggcaacgtcactcgctgctttgagcattacgagaagggcagcgt
gccagtcctcatcatccacatcttcatcgtgttcagcttcttcctggtcttcctcatcatcctcttctgcaacctggtcatcatccgtaccttgc
tcatgcagccggtgcagcagcagcgcaacgctgaagtcaagcgccgggcgctgtggatggtgtgcacggtcttggcggtgttcatca
tctgcttcgtgccccaccacgtggtgcagctgccctggacccttgctgagctgggcttccaggacagcaaattccaccaggccattaat
gatgcacatcaggtcaccctctgcctccttagcaccaactgtgtcttagaccctgttatctactgtttcctcaccaagaagttccgcaagca
cctcaccgaaaagttctacagcatgcgcagtagccggaaatgctcccgggccaccacggatacggtcactgaagtggttgtgccattc
aaccagatccctggcaattccctcaaaaattag

FIG. 5

SEQUENCE OF G-PROTEIN COUPLED RECEPTOR AGTRL1

AGTRL1 AMINO ACID SEQUENCE

SEQ ID NO: 9

MEEGGDFDNYYGADNQSECEYTDWKSSGALIPAIYMLVFLLGTTGNGLVLWTVFRS
SREKRRSADIFIASLAVADLTFVVTLPLWATYTYRDYDWPFGTFFCKLSSYLIFVNMY
ASVFCLTGLSFDRYLAIVRPVANARLRLRVSGAVATAVLWVLAALLAMPVMVLRTT
GDLENTTKVQCYMDYSMVATVSSEWAWEVGLGVSSTTVGFVVPFTIMLTCYFFIAQ
TIAGHFRKERIEGLRKRRRLLSIIVVLVVTFALCWMPYHLVKTLYMLGSLLHWPCDF
DLFLMNIFPYCTCISYVNSCLNPFLYAFFDPRFRQACTSMLCCGQSRCAGTSHSSSGE
KSASYSSGHSQGPGPNMGKGGEQMHEKSIPYSQETLVVD

AGTRL1 AMINO ACID SEQUENCE

SEQ ID NO: 10 atggaggaaggtggtgattttgacaactactatggggcagacaaccagtctgagtgtgagtacacagactggaaatcctcgggggcc
ctcatccctgccatctacatgttggtcttcctcctgggcaccacggggcaacggtctggtgctctggaccgtgtttcggagcagccggga
gaagaggcgctcagctgatatcttcattgctagcctggcggtggctgacctgaccttcgtggtgacgctgcccctgtgggctacctaca
cgtaccgggactatgactggccctttgggaccttcttctgcaagctcagcagctacctcatcttcgtcaacatgtacgccagcgtcttctg
cctcaccggcctcagcttcgaccgctacctggccatcgtgaggccagtggccaatgctcggctgaggctgcgggtcagcggggccg
tggccacggcagttctttgggtgctggccgccctcctggccatgcctgtcatggtgttacgcaccaccggggacttggagaacaccac
taaggtgcagtgctacatggactactccatggtggccactgtgagctcagagtgggcctgggaggtgggccttggggtctcgtccacc
accgtgggctttgtggtgcccttcaccatcatgctgacctgttacttcttcatcgcccaaaccatcgctggccacttccgcaaggaacgc
atcgagggcctgcggaagcggcgccggctgctcagcatcatcgtggtgctggtggtgacctttgccctgtgctggatgccctaccacc
tggtgaagacgctgtacatgctgggcagcctgctgcactggccctgtgactttgacctcttcctcatgaacatcttcccctactgcacctg
catcagctacgtcaacagctgcctcaaccccttcctctatgccttttttcgaccccgcttccgccaggcctgcacctccatgctctgctgt
ggccagagcaggtgcgcaggcacctcccacagcagcagtggggagaagtcagccagctactcttcggggcacagccagggggcc
cggccccaacatgggcaagggtggagaacagatgcacgagaaatccatccctacagccaggagacccttgtggttgactag

FIG. 6

SEQUENCE OF G-PROTEIN COUPLED RECEPTOR C3AR

C3AR AMINO ACID SEQUENCE

SEQ ID NO: 11

MASFSAETNSTDLLSQPWNEPPVILSMVILSLTFLLGLPGNGLVLWVAGLKMQRTVN
TIWFLHLTLADLLCCLSLPFSLAHLALQGQWPYGRFLCKLIPSIIVLNMFASVFLLTAIS
LDRCLVVFKPIWCQNHRNVGMACSICGCIWVVAFVMCIPVFVYREIFTTDNHNRCG
YKFGLSSSLDYPDFYGDPLENRSLENIVQPPGEMNDRLDPSSFQTNDHPWTVPTVFQP
QTFQRPSADSLPRGSARLTSQNLYSNVFKPADVVSPKIPSGFPIEDHETSPLDNSDAFL
STHLKLFPSASSNSFYESELPQGFQDYYNLGQFTDDDQVPTPLVAITITRLVVGFLLPS
VIMIACYSFIVFRMQRGRFAKSQSKTFRVAVVVVAVFLVCWTPYHIFGVLSLLTDPET
PLGKTLMSWDHVCIALASANSCFNPFLYALLGKDFRKKARQSIQGILEAAFSEELTRS
THCPSNNVISERNSTTV

C3AR NUCLEOTIDE SEQUENCE

SEQ ID NO: 12 atggcgtctttctctgctgagaccaattcaactgacctactctcacagccatggaatgagcccccagtaattctctccatggtcattctcag
ccttactttttactgggattgccaggcaatgggctggtgctgtgggtggctggcctgaagatgcagcggacagtgaacacaatttggtt
cctccacctcaccttggcggacctcctctgctgcctctccttgcccttctcgctggctcacttggctctccagggacagtggccctacgg
caggttcctatgcaagctcatccctccatcattgtcctcaacatgtttgccagtgtcttcctgcttactgccattagcctggatcgctgtctt
gtggtattcaagccaatctggtgtcagaatcatcgcaatgtagggatggcctgctctatctgtggatgtatctgggtggtggcttttgtgat
gtgcattcctgtgttcgtgtaccgggaaatcttcactacagacaaccataatagatgtggctacaaatttggtctctccagctcattagatta
tccagacttttatggagatccactagaaaacaggtctcttgaaaacattgttcagccgcctggagaaatgaatgataggttagatccttcct
ctttccaaacaaatgatcatccttggacagtccccactgtcttccaacctcaaacatttcaaagaccttctgcagattcactccctagggt
tctgctaggttaacaagtcaaaatctgtattctaatgtatttaaacctgctgatgtggtctcacctaaaatccccagtgggtttcctattgaag
atcacgaaaccagcccactggataactctgatgcttttctctctactcatttaaagctgttccctagcgcttctagcaattccttctacgagtc
tgagctaccacaaggtttccaggattattacaatttaggccaattcacagatgacgatcaagtgccaacaccctcgtggcaataacgat
cactaggctagtggtgggtttcctgctgccctctgttatcatgatagcctgttacagcttcattgtcttccgaatgcaaaggggccgcttcg
ccaagtctcagagcaaaaccttcgagtggccgtggtggtggtggctgtctttcttgtctgctggactccataccacattttggagtcctg
tcattgcttactgacccagaaactcccttggggaaaactctgatgtcctgggatcatgtatgcattgctctagcatctgccaatagttgcttt
aatcccttccttatgccctcttggggaaagattttaggaagaaagcaaggcagtccattcagggaattctggaggcagccttcagtgag
gagctcacacgttccacccactgtccctcaaacaatgtcatttcagaaagaaatagtacaactgtgtga

FIG. 7

SEQUENCE OF G-PROTEIN COUPLED RECEPTOR CCR5

CCR5 AMINO ACID SEQUENCE

SEQ ID NO: 13

MDYQVSSPIYDINYYTSEPCQKINVKQIAARLLPPLYSLVFIFGFVGNMLVILILINCKR
LKSMTDIYLLNLAISDLFFLLTVPFWAHYAAAQWDFGNTMCQLLTGLYFIGFFSGIFF
IILLTIDRYLAVVHAVFALKARTVTFGVVTSVITWVVAVFASLPGIIFTRSQKEGLHYT
CSSHFPYSQYQFWKNFQTLKIVILGLVLPLLVMVICYSGILKTLLRCRNEKKRHRAVR
LIFTIMIVYFLFWAPYNIVLLLNTFQEFFGLNNCSSSNRLDQAMQVTETLGMTHCCIN
PIIYAFVGEKFRNYLLVFFQKHIAKRFCKCCSIFQQEAPERASSVYTRSTGEQEISVGL
ATGGATTATCAAGTGTCAAGTCCAATCTATGACATCAATTATTATACATCGGAGC
CCTGC

CCR5 NUCLEOTIDE SEQUENCE

SEQ ID NO: 14 caaaaaatcaatgtgaagcaaatcgcagcccgcctcctgcctccgctctactcactggtgttcatctttggttttgtgggcaacatgctgg
tcatcctcatcctgataaaactgcaaaaggctgaagagcatgactgacatctacctgctcaacctggccatctctgacctgttttccttcta
ctgtcccttctgggctcactatgctgccgcccagtggactttggaaatacaatgtgtcaactcttgacagggctctattttataggcttct
tctctggaatcttcttcatcatcctcctgacaatcgataggtacctggctgtcgtccatgctgtgtttgctttaaaagccaggacggtcacct
ttgggggtggtgacaagtgtgatcacttgggtggtggctgtgtttgcgtctctcccaggaatcatctttaccagatctcaaaaagaaggtctt
cattacacctgcagctctcattttccatacagtcagtatcaattctggaagaatttccagacattaaagatagtcatcttggggctggtcctg
ccgctgcttgtcatggtcatctgctactcgggaatcctaaaaactctgcttcggtgtcgaaatgagaagaagaggcacagggctgtgag
gcttatcttcaccatcatgattgtttattttctcttctgggctccctacaacattgtccttctcctgaacaccttccaggaattctttggcctgaat
aattgcagtagctctaacaggttggaccaagctatgcaggtgacagagactcttgggatgacgcactgctgcatcaacccatcatcta
tgcctttgtcggggagaagttcagaaactacctcttagtcttcttccaaaagcacattgccaaacgcttctgcaaatgctgttctattttcca
gcaagaggctcccgagcgagcaagctcagtttacacccgatccactggggagcaggaaatatctgtgggcttgtga

FIG. 8

SEQUENCE OF G-PROTEIN COUPLED RECEPTOR CXCR4

CXCR4 AMINO ACID SEQUENCE

SEQ ID NO: 15

MEGISIYTSDNYTEEMGSGDYDSMKEPCFREENANFNKIFLPTIYSIIFLTGIVGNLVI
LVMGYQKKLRSMTDKYRLHLSVADLLFVITLPFWAVDAVANWYFGNFLCKAVHVI
YTVNLYSSVLILAFISLDRYLAIVHATNSQRPRKLLAEKVVYVGVWIPALLLTIPDFIF
ANVSEADDRYICDRFYPNDLWVVVFQFQHIMVGLILPGIVILSCYCIISKLSHSKGHQ
KRKALKTTVILILAFFACWLPYYIGISIDSFILLEIIKQGCEFENTVHKWISITEALAFFH
CCLNPILYAFLGAKFKTSAQHALTSVSRGSSLKILSKGKRGGHSSVSTESESSSFHSS

CXCR4 AMINO ACID SEQUENCE

SEQ ID NO: 16 atggaggggatcagtatatacacttcagataactacaccgaggaaatgggctcaggggactatgactccatgaaggaaccctgtttcc
gtgaagaaaatgctaatttcaataaaatcttcctgcccaccatctactccatcatcttcttaactggcattgtgggcaatggattggtcatcct
ggtcatgggttaccagaagaaactgagaagcatgacggacaagtacaggctgcacctgtcagtggccgacctcctctttgtcatcacg
cttcccttctgggcagttgatgccgtggcaaactggtactttgggaacttcctatgcaaggcagtccatgtcatctacacagtcaacctct
acagcagtgtcctcatcctggccttcatcagtctggaccgctacctggccatcgtccacgccaccaacagtcagaggccaaggaagct
gttggctgaaaaggtggtctatgttggcgtctggatccctgccctcctgctgactattcccgacttcatctttgccaacgtcagtgaggca
gatgacagatatatctgtgaccgcttctaccccaatgacttgtgggtggttgtgttccagtttcagcacatcatggttggccttatcctgcct
ggtattgtcatcctgtcctgctattgcattatcatctccaagctgtcacactccaagggccaccagaagcgcaaggccctcaagaccaca
gtcatcctcatcctggctttcttcgcctgttggctgccttactacattgggatcagcatcgactccttcatcctcctggaaatcatcaagcaa
gggtgtgagtttgagaacactgtgcacaagtggatttccatcaccgaggccctagctttcttccactgttgtctgaacccatcctctatgc
tttccttggagccaaatttaaaacctctgcccagcacgcactcacctctgtgagcagagggtccagcctcaagatcctctccaaaggaa
agcgaggtggacattcatctgtttccactgagtctgagtcttcaagttttcactccagctaa

FIG. 9

SEQUENCE OF G-PROTEIN COUPLED RECEPTOR PAR2

PAR2 AMINO ACID SEQUENCE

SEQ ID NO: 17

MRSPSAAWLLGAAILLAASLSCSGTIQGTNRSSKGRSLIGKVDGTSHVTGKGVTVET
VFSVDEFSASVLTGKLTTVFLPIVYTIVFVVGLPSNGMALWVFLFRTKKKHPAVIYM
ANLALADLLSVIWFPLKIAYHIHGNNWIYGEALCNVLIGFFYGNMYCSILFMTCLSVQ
RYWVIVNPMGHSRKKANIAIGISLAIWLLILLVTIPLYVVKQTIFIPALNITTCHDVLPE
QLLVGDMFNYFLSLAIGVFLFPAFLTASAYVLMIRMLRSSAMDENSEKKRKRAIKLIV
TVLAMYLICFTPSNLLLVVHYFLIKSQGQSHVYALYIVALCLSTLNSCIDPFVYYFVSH
DFRDHAKNALLCRSVRTVKQMQVSLTSKKHSRKSSSYSSSSTTVKTSY

PAR2 NUCLEOTIDE SEQUENCE

SEQ ID NO: 18 atgcggagccccagcgcggcgtggctgctgggggccgccatcctgctagcagcctctctctcctgcagtggcaccatccaaggaac
caatagatcctcaaaggaagaagccttattggtaaggttgatggcacatcccacgtcactggaaaaggagttacagttgaaacagtctt
ttctgtggatgagttttctgcatctgtcctcactggaaaactgaccactgtcttccttccaattgtctacacaattgtgtttgtggtgggtttgc
caagtaacggcatggccctgtgggtcttctttccgaactaagaagaagcaccctgctgtgatttacatggccaatctggccttggctga
cctcctctctgtcatctggttccccttgaagattgcctatcacatacatggcaacaactggatttatggggaagctctttgtaatgtgcttatt
ggcttttctatggcaacatgtactgttccattctcttcatgacctgcctcagtgtgcagaggtattgggtcatcgtgaacccatggggca
ctccaggaagaaggcaaacattgccattggcatctccctggcaatatggctgctgattctgctggtcaccatcccttgtatgtcgtgaag
cagaccatcttcattcctgccctgaacatcacgacctgtcatgatgttttgcctgagcagctcttggtgggagacatgttcaattacttcctc
tctctggccattgggtcttctgttccagccttcctcacagcctctgcctatgtgctgatgatcagaatgctgcgatcttctgccatggat
gaaaactcagagaagaaaaggaagagggccatcaaactcattgtcactgtcctggccatgtacctgatctgcttcactcctagtaaccct
ctgcttgtggtgcattatttctgattaagagccagggccagagccatgtctatgccctgtacattgtagccctctgcctctctaccccttaac
agctgcatcgacccctttgtctattactttgtttcacatgatttcagggatcatgcaaagaacgctctcctttgccgaagtgtccgcactgta
aagcagatgcaagtatccctcacctcaaagaaacactccaggaaatccagctcttactcttcaagttcaaccactgttaagacctcctatt
ga

FIG. 10

Map and seq of pMEX2 Schematic structure and features of the GPCR expression vector pMEX2

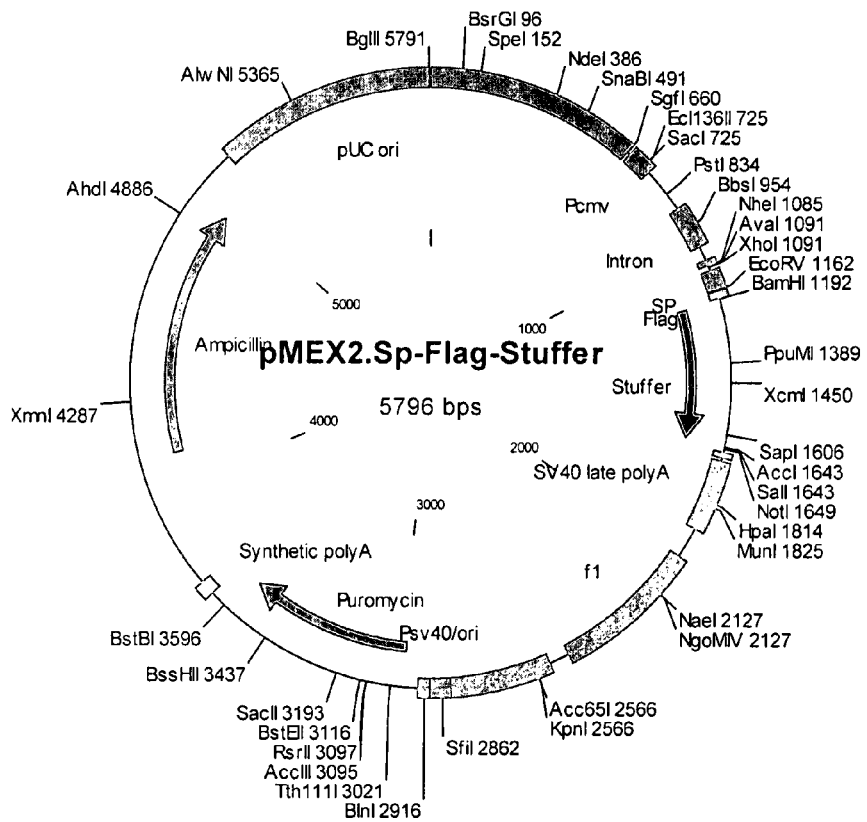

```
Molecule Information
-Molecule: pMEX2.Sp-Flag-Stuffer,  5796 bps DNA Circular
-Description: For expression of an N-ter Flag-tagged GPCR
-Molecule Features:

Type      Start     End    Name             Description
REGION        1     750    Pcmv             CMV early promote/enhancer
REGION     1067    1085                     T7 Promoter
REGION     1102    1164    SP               Secretory signal peptide
REGION     1168    1191    Flag             affinity tag
GENE       1198    1642    Stuffer
REGION     1677    1659 C                   T3 Promoter
REGION     1686    1907    SV40 late polyA  SV40 Polyadenylation signal
REGION     2002    2457    f1               phage f1 origin
REGION     2519    2937    Psv40/ori        SV40 enhancer and early promoter
REGION     2835    2900                     SV40 min. origin of replication
GENE       2982    3558    Puromycin        Selectable marker
GENE       4104    4964    Ampicillin       beta-lactamase
REGION     5115    5791    pUC ori          pUC replication origin
```

FIG. 11A

Nucleotide sequence of pMEX2

SEQ ID NO: 19

```
   1 tcaatattgg ccattagcca tattattcat tggttatata gcataaatca atattggcta
  61 ttggccattg catacgttgt atctatatca taatatgtac atttatattg gctcatgtcc
 121 aatatgaccg ccatgttggc attgattatt gactagttat taatagtaat caattacggg
 181 gtcattagtt catagcccat atatggagtt ccgcgttaca taacttacgg taaatggccc
 241 gcctggctga ccgcccaacg acccccgccc attgacgtca ataatgacgt atgttcccat
 301 agtaacgcca ataggractt tccattgacg tcaatgggtg gagtatttac ggtaaactgc
 361 ccacttggca gtacatcaag tgtatcatat gccaagtccg cccccattg acgtcaatga
 421 cggtaaatgg cccgcctggc attatgccca gtacatgacc ttacgggact ttcctacttg
 481 gcagtacatc tacgtattag tcatcgctat taccatggtg atgcggtttt ggcagtacac
 541 caatgggcgt ggatagcggt ttgactcacg gggatttcca agtctccacc ccattgacgt
 601 caatgggagt ttgttttggc accaaaatca acgggacttt ccaaaatgtc gtaacaactg
 661 cgatcgcccg ccccgttgac gcaaatgggc ggtaggcgtg tacggtggga ggtctatata
 721 agcagagctc gtttagtgaa ccgtcagatc actagaagct ttattgcggt agtttatcac
 781 agttaaattg ctaacgcagt cagtgcttct gacacaacag tctcgaactt aagctgcagt
 841 gactctctta aggtagcctt gcagaagttg gtcgtgaggc actgggcagg taagtatcaa
 901 ggttacaaga caggtttaag gagaccaata gaaactgggc ttgtcgagac agagaagact
 961 cttgcgtttc tgataggcac ctattggtct tactgacatc cactttgcct ttctctccac
1021 aggtgtccac tcccagttca attacagctc ttaaggctag agtacttaat acgactcact
1081 ataggctagc ctcgagccac catggagaca gacacactcc tgctatgggt actgctgctc
1141 tgggttccag gttccactgg tgatatcgac tataaagatg atgacgacaa gggatcctgc
1201 cccagtcctt tggcttcatc gtgccactgc tgatcatgct gttctgctac ggattcaccc
1261 tgcgtacgct gtttaaggcc cacatggggc agaagcaccg ggccatgcgg tcatctttg
1321 ctgtcgtcct catcttcctg ctctgctggc tgccctacaa cctggtcctg ctggcagaca
1381 ccctcatgag gacccaggtg atccaggaga cctgtgagcg ccgcaatcac atcgaccggg
1441 ctctggatgc caccgagatt ctgggcatcc ttcacagctg cctcaacccc ctcatctacg
1501 ccttcattgg ccagaagttt cgccatggac tcctcaagat tctagctata catggcttga
1561 tcagcaagga ctccctgccc aaagacagca ggccttcctt tgttggctct tcttcagggc
1621 acacttccac tactctctga tagtcgacgc ggccgcttcc ctttagtgag ggttaatgct
1681 tcgagcagac atgataagat acattgatga gtttggacaa accacaacta gaatgcagtg
1741 aaaaaaatgc tttatttgtg aaatttgtga tgctattgct ttatttgtaa ccattataag
1801 ctgcaataaa caagttaaca acaacaattg cattcatttt atgtttcagg ttcaggggga
1861 gatgtgggag gtttttaaa gcaagtaaaa cctctacaaa tgtggtaaaa tccgataagg
1921 atcgatccgg gctggcgtaa tagcgaagag gcccgcaccg atcgcccttc ccaacagttg
1981 cgcagcctga atggcgaatg gacgcgccct gtagcggcgc attaagcgcg gcgggtgtgg
2041 tggttacgcg cagcgtgacc gctacacttg ccagcgccct agcgcccgct cctttcgctt
2101 tcttcccttc ctttctcgcc acgttcgccg gctttccccg tcaagctcta aatcggggc
2161 tccctttagg gttccgattt agtgctttac ggcacctcga cccaaaaaa cttgattagg
2221 gtgatggttc acgtagtggg ccatcgccct gatagacggt ttttcgccct ttgacgttgg
2281 agtccacgtt ctttaatagt ggactcttgt tccaaactgg aacaacactc aaccctatct
2341 cggtctattc ttttgattta agggatttt gccgatttc ggcctattgg ttaaaaaatg
2401 agctgattta acaaaattt aacgcgaatt ttaacaaaat attaacgctt acaatttcct
2461 gatgcggtat tttctcctta cgcatctgtg cggtatttca caccgcatac gcggatctgc
2521 gcagcaccat ggcctgaaat aacctctgaa agaggaactt ggttaggtac cttctgaggc
2581 ggaaagaacc agctgtggaa tgtgtgtcag ttagggtgtg aaagtcccc aggctcccca
2641 gcagcagaa gtatgcaaag catgcatctc aattagtcag caaccaggtg tggaaagtcc
2701 ccaggctccc cagcaggcag aagtatgcaa agcatgcatc tcaattagtc agcaaccata
2761 gtcccgcccc taactccgcc catcccgccc taactccgc cagttccgc ccattctccg
2821 ccccatggct gactaatttt ttttatttat gcagaggccg aggccgcctc ggcctctgag
2881 ctattccaga agtagtgagg aggcttttt ggaggcctag gcttttgcaa aaagcttgat
2941 tcttctgaca acagtctc gaacttaagg ctagagccac catgaccgag tacaagccca
3001 cggtgcgcct cgccaccgc gacgacgtcc ccagggccgt acgcaccctc gccgccgcgt
3061 tcgccgacta ccccgccacg cgccacaccg tcgatccgga ccgccacatc gagcgggtca
3121 ccgagctgca agaactcttc ctcacgcgcg tcgggctcga tcggcaag tgtgggtcg
3181 cggacgacgg cgccgcggtg gcggtctgga ccacgccgga gagcgtcgaa gcggggcgg
3241 tgttcgccga gatcggcccg cgcatggccg agttgagcgg ttcccggctg gccgcgcagc
```

FIG. 11B

```
3301  aacagatgga aggcctcctg gcgccgcacc ggcccaagga gcccgcgtgg ttcctggcca
3361  ccgtcggcgt ctcgcccgac caccagggca agggtctggg cagcgccgtc gtgctccccg
3421  gagtggaggc ggccgagcgc gccggggtgc ccgccttcct ggagacctcc gcgccccgca
3481  acctcccctt ctacgagcgg ctcggcttca ccgtcaccgc cgacgtcgag gtgcccgaag
3541  gaccgcgcac ctggtgcatg acccgcaagc ccggtgcata agtagtactc tggagttcga
3601  aatgaccgac caagcgacgc ccaacctgcc atcacgatgg ccgcaataaa atatctttat
3661  tttcattaca tctgtgtgtt ggttttttgt gtgaatcgat agcgataaag atccgcgtat
3721  ggtgcactct cagtacaatc tgctctgatg ccgcatagtt aagccagccc cgacacccgc
3781  caacacccgc tgacgcgccc tgacgggctt gtctgctccc ggcatccgct tacagacaag
3841  ctgtgaccgt ctccgggagc tgcatgtgtc agaggttttc accgtcatca ccgaaacgcg
3901  cgagacgaaa gggcctcgtg atacgcctat ttttataggt taatgtcatg ataataatgg
3961  tttcttagac gtcaggtggc acttttcggg gaaatgtgcg cggaacccct atttgtttat
4021  ttttctaaat acattcaaat atgtatccgc tcatgagaca ataaccctga taaatgcttc
4081  aataatattg aaaaggaag agtatgagta ttcaacattt ccgtgtcgcc cttattccct
4141  tttttgcggc attttgcctt cctgttttg ctcacccaga aacgctggtg aaagtaaaag
4201  atgctgaaga tcagttgggt gcacgagtgg gttacatcga actggatctc aacagcggta
4261  agatccttga gagttttcgc cccgaagaac gttttccaat gatgagcact tttaaagttc
4321  tgctatgtgg cgcggtatta tcccgtattg acgccgggca agagcaactc ggtcgccgca
4381  tacactattc tcagaatgac ttggttgagt actcaccagt cacagaaaag catcttacgg
4441  atggcatgac agtaagagaa ttatgcagtg ctgccataac catgagtgat aacactgcgg
4501  ccaacttact tctgacaacg atcggaggac cgaaggagct aaccgctttt ttgcacaaca
4561  tgggggatca tgtaactcgc cttgatcgtt gggaaccgga gctgaatgaa gccataccaa
4621  acgacgagcg tgacaccacg atgcctgtag caatggcaac aacgttgcgc aaactattaa
4681  ctggcgaact acttactcta gcttcccggc aacaattaat agactggatg gaggcggata
4741  aagttgcagg accacttctg cgctcggccc ttccggctgg ctggtttatt gctgataaat
4801  ctggagccgg tgagcgtggg tctcgcggta tcattgcagc actggggcca gatggtaagc
4861  cctcccgtat cgtagttatc tacacgacgg ggagtcaggc aactatggat gaacgaaata
4921  gacagatcgc tgagataggt gcctcactga ttaagcattg gtaactgtca gaccaagttt
4981  actcatatat actttagatt gatttaaaac ttcatttta atttaaaagg atctaggtga
5041  agatccttt tgataatctc atgaccaaaa tcccttaacg tgagttttcg ttccactgag
5101  cgtcagaccc cgtagaaaag atcaaaggat cttcttgaga tcctttttt ctgcgcgtaa
5161  tctgctgctt gcaaacaaaa aaaccaccgc taccagcggt ggtttgtttg ccggatcaag
5221  agctaccaac tcttttccg aaggtaactg gcttcagcag agcgcagata ccaaatactg
5281  ttcttctagt gtagccgtag ttaggccacc acttcaagaa ctctgtagca ccgcctacat
5341  acctcgctct gctaatcctg ttaccagtgg ctgctgccag tggcgataag tcgtgtctta
5401  ccgggttgga ctcaagacga tagttaccgg ataaggcgca gcggtcgggc tgaacggggg
5461  gttcgtgcac acagcccagc ttggagcgaa cgacctacac cgaactgaga tacctacagc
5521  gtgagctatg agaaagcgcc acgcttcccg aagggagaaa ggcggacagg tatccggtaa
5581  gcggcagggt cggaacagga gagcgcacga gggagcttcc agggggaaac gcctggtatc
5641  tttatagtcc tgtcgggttt cgccacctct gacttgagcg tcgatttttg tgatgctcgt
5701  caggggggcg gagcctatgg aaaaacgcca gcaacgcggc ctttttacgg ttcctggcct
5761  tttgctggcc ttttgctcac atggctcgac agatct
```

FIG. 12

Schematic structure and features of the GPCR inducible expression vector pMEX5

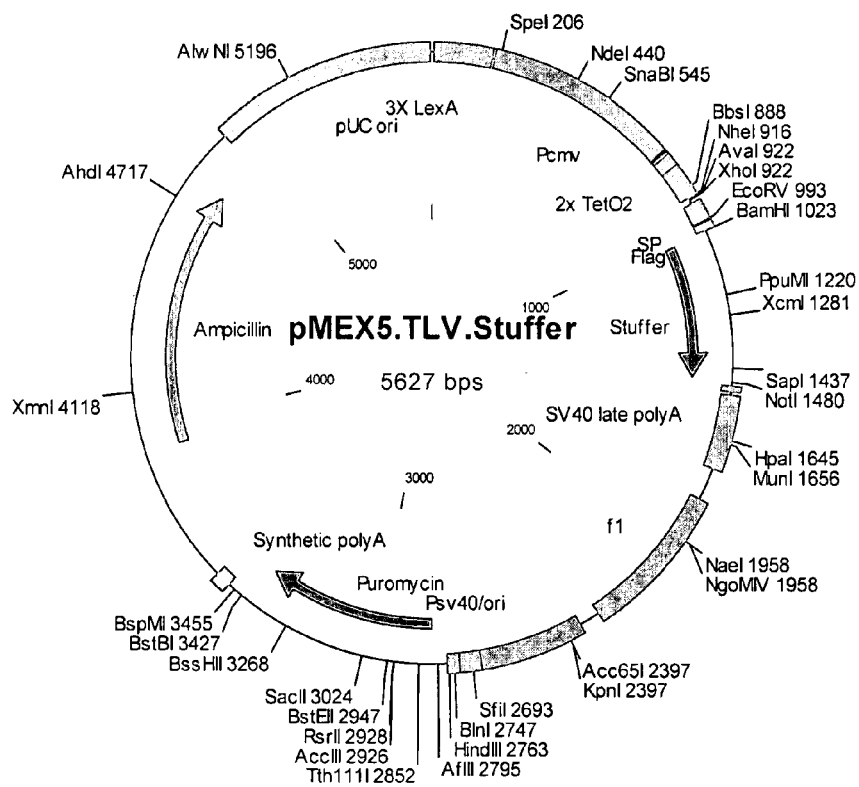

```
Molecule Information
-Molecule: pMEX5.TLV.Stuffer, 5627 bps DNA Circular
-Description: Expression vector for GPCRs under an inducible promoter
 control Molecule Features:
Type      Start   End    Name             Description
REGION       7    182    3X LexA          3 copies of LexA binding sites
REGION     189    915    Pcmv
REGION     761    767                     TATA box
REGION     777    816    2x TetO2         tetracyclin operator
REGION     933    995    SP
REGION     999   1022    Flag
GENE      1029   1473    Stuffer
REGION    1517   1738    SV40 late polyA  SV40 Polyadenylation signal
REGION    1833   2288    f1               phage f1 origin
REGION    2350   2768    Psv40/ori        SV40 enhancer and early promoter
REGION    2666   2731                     SV40 min. origin of replication
GENE      2813   3389    Puromycin        Selectable marker
GENE      3935   4795    Ampicillin       beta-lactamase
REGION    4946   5622    pUC ori          pUC replication origin
```

FIG. 13A

Nucleotide sequence of pMEX5

SEQ ID NO: 20

```
   1 tctagactgt atgtacatac agagttcttg agtgatccct gtatgtacat acaggtcatc
  61 atgaagtagt ctgtatgtac atacagagaa cttgagtgat ccctgtatgt acatacagtt
 121 caagatactt agttctgtat gtacatacag agttcttgag tgatccctgt atgtacatac
 181 agtctagagt tgacattgat tattgactag ttattaatag taatcaatta cggggtcatt
 241 agttcatagc ccatatatgg agttccgcgt tacataactt acggtaaatg gcccgcctgg
 301 ctgaccgccc aacgacccc gccattgac gtcaataatg acgtatgttc ccatagtaac
 361 gccaataggg actttccatt gacgtcaatg ggtggagtat ttacggtaaa ctgcccactt
 421 ggcagtacat caagtgtatc atatgccaag tacgccccct attgacgtca atgacggtaa
 481 atggcccgcc tggcattatg cccagtacat gaccttatgg gactttccta cttggcagta
 541 catctacgta ttagtcatcg ctattaccat ggtgatgcgg ttttggcagt acatcaatgg
 601 gcgtggatag cggtttgact cacggggatt tccaagtctc caccccattg acgtcaatgg
 661 gagtttgttt tggaaccaaa atcaacggga cttccaaaa tgtcgtaaca actccgcccc
 721 attgacgcaa atgggcggta ggcgtgtacg gtgggaggtc tatataagca gagctctccc
 781 tatcagtgat agagatctcc ctatcagtga tagagatcgt cgacgagctc gtttagtgaa
 841 ccgtcagatc gcctggagac gccatccacg ctgttttgac ctccatagaa gacaccggga
 901 ccgatccagc ctccggctag cctcgagcca ccatggagac agacacactc ctgctatggg
 961 tactgctgct ctgggttcca ggttccactg gtgatatcga ctataaagat gatgacgaca
1021 agggatcctg ccccagtcct ttggcttcat cgtgccactg ctgatcatgc tgttctgcta
1081 cggattcacc ctgcgtacgc tgtttaaggc ccacatgggg cagaagcacc gggccatgcg
1141 ggtcatcttt gctgtcgtcc tcatcttcct gctctgctgg ctgccctaca acctggtcct
1201 gctggcagac accctcatga ggacccaggt gatccaggag acctgtgagc gccgcaatca
1261 catcgaccgg gctctggatg ccaccgagat tctgggcatc cttcacagct gcctcaaccc
1321 cctcatctac gccttcattg ccagaagtt cgccatgga ctcctcaaga ttctagctat
1381 acatggcttg atcagcaagg actccctgcc caaagacagc aggccttcct tgttggctc
1441 ttcttcaggg cacacttcca ctactctctg atagtcgacg cggccgcttc cctttagtga
1501 gggttaatgc ttcgagcaga catgataaga tacattgatg agtttggaca accacaact
1561 agaatgcagt gaaaaaatg ctttatttgt gaaatttgtg atgctattgc tttatttgta
1621 accattataa gctgcaataa acaagttaac aacaacaatt gcattcattt tatgtttcag
1681 gttcagggg agatgtggga ggttttttaa agcaagtaaa acctctacaa atgtggtaaa
1741 atccgataag gatcgatccg gctggcgta atagcgaaga ggcccgcacc gatcgccctt
1801 cccaacagtt gcgcagcctg aatggcgaat ggacgcgccc tgtagcggcg cattaagcgc
1861 ggcgggtgtg tggttacgc gcagcgtgac cgctacactt gccagcgccc tagcgcccgc
1921 tcctttcgct ttcttccctt cctttctcgc cacgttcgcc ggctttcccc gtcaagctct
1981 aaatcggggg ctcccttag ggttccgatt tagtgcttta cggcacctcg accccaaaaa
2041 acttgattag ggtgatggtt cacgtagtgg gccatcgccc tgatagacgg ttttcgccc
2101 tttgacgttg gagtccacgt tctttaatag tggactcttg ttccaaactg gaacaacact
2161 caaccctatc tcggtctatt cttttgattt ataagggatt tgccgatttc ggcctattg
2221 gttaaaaaat gagctgattt aacaaaaatt taacgcgaat tttaacaaaa tattaacgct
2281 tacaatttcc tgatgcggta ttttctcctt acgcatctgt gcggtatttc acaccgcata
2341 cgcggatctg cgcagcacca tggcctgaaa taacctctga agagaact tggttaggta
2401 ccttctgagg cggaaagaac cagctgtgga atgtgtgtca gttagggtgt ggaaagtccc
2461 caggctcccc agcaggcaga agtatgcaaa gcatgcatct caattagtca gcaaccaggt
2521 gtggaaagtc cccaggctcc ccagcaggca gaagtatgca aagcatgcat ctcaattagt
2581 cagcaaccat agtcccgccc ctaactccgc ccatcccgcc cctaactccg cccagttccg
2641 cccattctcc gccccatggc tgactaattt ttttatttta tgcagaggcc gaggccgcct
2701 cggcctctga gctattccag aagtagtgag gaggcttttt tggaggccta ggcttttgca
2761 aaaagcttga ttcttctgac acaacagtct cgaacttaag gctagagcca ccatgaccga
2821 gtacaagccc acggtgcgcc tcgccacccg cgacgacgtc cccagggccg tacgcaccct
2881 cgccgccgcg ttcgccgact accccgccac gcgccacacc gtcgatccgg accgccacat
2941 cgagcgggtc accgagctgc aagaactctt cctcacgcgc gtcgggctcg acatcggcaa
3001 ggtgtgggtc gcggacgacg gcgccgcggt ggcggtctgg accacgccgg agagcgtcga
3061 agcggggggcg gtgttcgccg agatcggccc gcgcatggcc gagttgagcg gttccggct
3121 ggccgcgcag caacagatgg aaggcctcct ggcgccgcac cggcccaagg agcccgcgtg
3181 gttcctggcc accgtcggcg tctcgcccga ccaccagggc aagggtctgg gcagcgccgt
3241 cgtgctcccc ggagtggagg cggccgagcg cgccggggtg cccgccttcc tggagacctc
```

FIG. 13B

```
3301  cgcgccccgc aacctcccct tctacgagcg gctcggcttc accgtcaccg ccgacgtcga
3361  ggtgcccgaa ggaccgcgca cctggtgcat gacccgcaag cccggtgcat aagtagtact
3421  ctggagttcg aaatgaccga ccaagcgacg cccaacctgc catcacgatg gccgcaataa
3481  aatatcttta ttttcattac atctgtgtgt tggtttttg tgtgaatcga tagcgataaa
3541  gatccgcgta tggtgcactc tcagtacaat ctgctctgat gccgcatagt taagccagcc
3601  ccgacacccg ccaacacccg ctgacgcgcc ctgacgggct tgtctgctcc cggcatccgc
3661  ttacagacaa gctgtgaccg tctccgggag ctgcatgtgt cagaggtttt caccgtcatc
3721  accgaaacgc gcgagacgaa agggcctcgt gatacgccta tttttatagg ttaatgtcat
3781  gataataatg gtttcttaga cgtcaggtgg cacttttcgg ggaaatgtgc gcggaacccc
3841  tatttgttta ttttctaaa tacattcaaa tatgtatccg ctcatgagac aataaccctg
3901  ataaatgctt caataatatt gaaaaaggaa gagtatgagt attcaacatt tccgtgtcgc
3961  ccttattccc ttttttgcgg cattttgcct tcctgttttt gctcacccag aaacgctggt
4021  gaaagtaaaa gatgctgaag atcagttggg tgcacgagtg ggttacatcg aactggatct
4081  caacagcggt aagatccttg agagttttcg ccccgaagaa cgttttccaa tgatgagcac
4141  ttttaaagtt ctgctatgtg gcgcggtatt atcccgtatt gacgccgggc aagagcaact
4201  cggtcgccgc atacactatt ctcagaatga cttggttgag tactcaccag tcacagaaaa
4261  gcatcttacg gatggcatga cagtaagaga attatgcagt gctgccataa ccatgagtga
4321  taacactgcg gccaacttac ttctgacaac gatcggagga ccgaaggagc taaccgcttt
4381  tttgcacaac atgggggatc atgtaactcg ccttgatcgt tgggaaccgg agctgaatga
4441  agccatacca aacgacgagc gtgacaccac gatgcctgta gcaatggcaa caacgttgcg
4501  caaactatta actggcgaac tacttactct agcttcccgg caacaattaa tagactggat
4561  ggaggcggat aaagttgcag gaccacttct gcgctcggcc cttccggctg gctggtttat
4621  tgctgataaa tctggagccg gtgagcgtgg gtctcgcggt atcattgcag cactggggcc
4681  agatggtaag ccctcccgta tcgtagttat ctacacgacg gggagtcagg caactatgga
4741  tgaacgaaat agacagatcg ctgagatagg tgcctcactg attaagcatt ggtaactgtc
4801  agaccaagtt tactcatata tactttagat tgatttaaaa cttcattttt aatttaaaag
4861  gatctaggtg aagatccttt tgataatct catgaccaaa atcccttaac gtgagttttc
4921  gttccactga gcgtcagacc ccgtagaaaa gatcaaagga tcttcttgag atcctttttt
4981  tctgcgcgta atctgctgct tgcaaacaaa aaaaccaccg ctaccagcgg tggtttgttt
5041  gccggatcaa gagctaccaa ctcttttcc gaaggtaact ggcttcagca gagcgcagat
5101  accaaatact gttcttctag tgtagccgta gttaggccac cacttcaaga actctgtagc
5161  accgcctaca tacctcgctc tgctaatcct gttaccagtg gctgctgcca gtggcgataa
5221  gtcgtgtctt accgggttgg actcaagacg atagttaccg gataaggcgc agcggtcggg
5281  ctgaacgggg ggttcgtgca cacagcccag cttggagcga acgacctaca ccgaactgag
5341  atacctacag cgtgagctat gagaaagcgc cacgcttccc gaagggagaa aggcggacag
5401  gtatccggta agcggcaggg tcggaacagg agagcgcacg agggagcttc caggggaaa
5461  cgcctggtat ctttatagtc ctgtcgggtt tcgccacctc tgacttgagc gtcgattttt
5521  gtgatgctcg tcagggggggc ggagcctatg gaaaaacgcc agcaacgcgg cctttttacg
5581  gttcctggcc ttttgctggc cttttgctca catggctcga cagatct
```

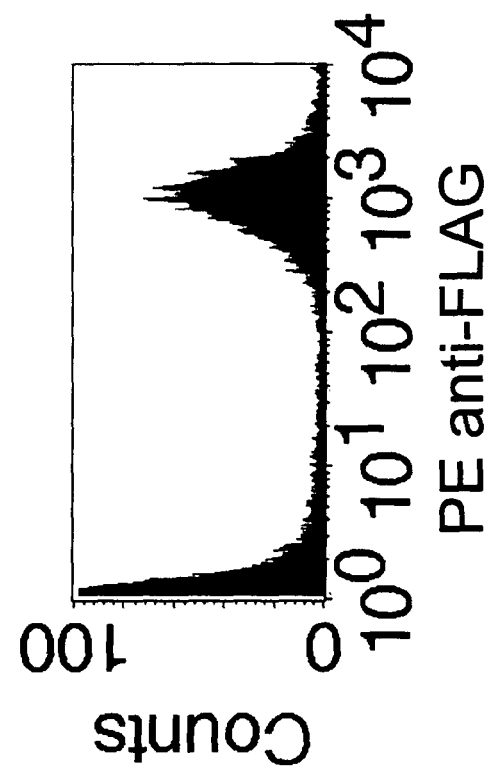
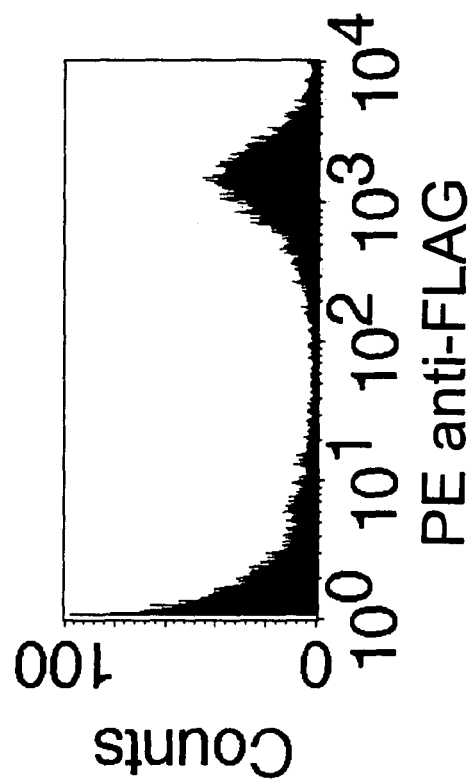
FIG. 17

GPCR-EXPRESSING CELL LINES

CROSS-REFERENCE TO RELATED APPLICATIONS

This application claims the benefit of Provisional Patent Applications No. 60/730,997, filed Oct. 28, 2005, the disclosure of which is incorporated by reference herein in its entirety for all purposes.

BACKGROUND OF THE INVENTION

This invention relates generally to the field of G protein coupled receptor (GPCR) expression and modulation.

G protein-coupled receptors (GPCRs) are a historically successful therapeutic target family, with GPCR-directed drugs covering a wide range of therapeutic indications. As cell surface receptors, GPCRs are vital to cellular functioning, because they are primary mediators of cell to cell communication.

Mammalian cells express very low levels of endogenous GPCRs, generally with no more than three thousand copies per cell. This level is sufficient for receptor function, but offers a challenge to GPCR research, which often requires much higher concentrations of functional proteins. For example, structural studies, small molecule drug design and generation of functional antibodies against the native GPCR conformation require expression levels that are orders of magnitude higher than what is seen using current methods.

Attempts have been made to isolate mammalian cell lines that overexpress exogenous GPCRs, but these past attempts have failed due to the cellular toxicity that occurs with receptor overexpression. Attempts to create expression systems in "lower" organisms have similarly met with limited success due to inefficient folding (bacteria), low yield (yeast) or incorrect post-translation modification (baculovirus).

A need thus exists for stable, high-expression systems capable of providing multiple copies of GPCR proteins for structural and functional studies.

SUMMARY OF THE INVENTION

Accordingly, the present invention provides a novel method for development of mammalian cell lines that overexpress G protein coupled receptor (GPCR) proteins. Exemplary cell lines of the invention express GPCR at levels upwards of one million copies per cell. Such high levels of expression are surprising, given that conventional methods of expression yield much lower levels of expression for transmembrane proteins.

In a first aspect, the present invention provides a vector for facilitating high levels of expression of GPCR proteins in a cell line. The vector includes components such as a cytomegalovirus (CMV) promoter, a signal peptide, and epitope tag, a Kozak sequence, a poly-A site, and a viral origin of replication.

In second aspect, the invention provides a recombinant cell line which expresses GPCR proteins at a level of at least 150,000 copies per cell. In a further aspect, the invention provides methods for producing recombinant cell lines by transfecting a host cell with at least one expression vector. In a preferred embodiment of the invention, the expression vector may include a nucleotide sequence selected from SEQ ID NO: 19 and SEQ ID NO: 20.

In a still further aspect, the invention provides methods for using recombinant cell lines to screen for therapeutic candidates able to interact with a GPCR protein. The method includes expressing a GPCR amino acid sequence in a recombinant cell. A test entity is contacted with a region of the GPCR amino acid sequence, and this region presents a fragment of the GPCR amino acid sequence that is sufficient for the test entity to interact with the fragment. In an embodiment of the invention, the test entity interacts with the fragment in a detectable manner. Detection of the interaction between the test entity and the fragment of the GPCR amino acid sequence identifies the test entity as a therapeutic candidate.

In a still further aspect, the invention provides a method of using a GPCR-expressing cell line to identify a test compound which modulates the activity of the GPCR protein. This method includes making a first measurement, which involves measuring second messenger activity in the cell line in the absence of the test compound, and making a second measurement, which involves measuring second messenger activity in the presence of the test compound. The method encompasses a comparison of the first and second measurement to determine if there is a difference between the two. A difference between the first and second measurement identifies the test compound as a compound that modulates the activity of the GPCR. In a preferred embodiment of the invention, the cell line expresses at least 150,000 copies of the GPCR protein per cell.

In another aspect, the invention provides an antibody or antigen binding fragment that is able to bind to a structural feature of a GPCR protein. In a further aspect of the invention, the antibody or antigen binding fragment is raised against an immunogen which is a cell line expressing between 150,000 and 2,000,000 copies of GPCR protein per cell.

In a further aspect of the invention, a method is provided whereby cells expressing GPCR proteins are detected in a test sample. The test sample is contacted with an antibody specifically binding to a structural feature of a GPCR protein. Specific binding of the antibody to a structural feature of a GPCR protein identifies the presence of GPCR-expressing cells in the test sample. This method further includes the detection of specific binding of the antibody to a structural feature of a GPCR protein.

In a still further aspect of the invention, a method is provided for producing monoclonal antibodies for a GPCR protein. In this aspect of the invention, a test animal is immunized with at least one cell line expressing a GPCR protein, and the cell line preferably expresses at least 50,000 copies of said GPCR protein per cell. The test animal is induced to produce hybridomas, and the method includes isolating the hybridomas and screening for monoclonal antibodies using one or more cell-based assay systems.

In another aspect, the invention provides a kit for high throughput purification and quantification of recombinant proteins of one or more members of one or more GPCR families. A kit according to the invention comprises a vector for expressing the recombinant proteins at levels between 50,000 and 2,000,000 copies per cell. A kit according to the invention can also comprise an affinity chromatography resin, a proteolytic enzyme, an internal quantification standard, a matrix for MALDI-TOF mass spectrometry, as well as instructions for use of the kit.

In still another aspect, the invention provides a method for identifying a DNA sequence encoding a member of a GPCR family. This method includes the process of probing a cDNA library or genomic library with a labeled probe and identifying from the library sequences able to hybridize to the probe under stringent conditions. Encompassed in the scope of the invention are labeled probes comprising nucleotide sequences selected from SEQ ID NO: 1, 3, 5, 7, 9, 11, 13, 15 and 17.

In yet another aspect, the invention provides a method for producing a functional assay cell line. This method includes producing a cell line expressing a GPCR protein and coupling a functional reporter to binding of a ligand to the GPCR protein. The functional reporter is such that a binding event between the ligand and the GPCR protein is detectable as a reporter activity readout. In an exemplary embodiment of the invention, the cell line expresses a GPCR protein comprising an amino acid sequence selected from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, and SEQ ID NO: 17. In a preferred embodiment of the invention, the cell line expresses at least 150,000 copies of the GPCR protein per cell.

BRIEF DESCRIPTION OF THE DRAWINGS

FIG. 1 displays the amino acid sequence (SEQ ID NO: 1) and the nucleotide sequence (SEQ ID NO: 2) for the G-protein coupled receptor C5AR.

FIG. 2 displays the amino acid sequence (SEQ ID NO: 3) and the nucleotide sequence (SEQ ID NO: 4) for the G-protein coupled receptor NMUR1.

FIG. 3 displays the amino acid sequence (SEQ ID NO: 5) and the nucleotide sequence (SEQ ID NO: 6) for the G-protein coupled receptor P2RY2.

FIG. 4 displays the amino acid sequence (SEQ ID NO: 7) and the nucleotide sequence (SEQ ID NO: 8) for the G-protein coupled receptor PTAFR.

FIG. 5 displays the amino acid sequence (SEQ ID NO: 9) and the nucleotide sequence (SEQ ID NO: 10) for the G-protein coupled receptor AGTRL1.

FIG. 6 displays the amino acid sequence (SEQ ID NO: 11) and the nucleotide sequence (SEQ ID NO: 12) for the G-protein coupled receptor C3AR.

FIG. 7 displays the amino acid sequence (SEQ ID NO: 13) and the nucleotide sequence (SEQ ID NO: 14) for the G-protein coupled receptor CCR5.

FIG. 8 displays the amino acid sequence (SEQ ID NO: 15) and the nucleotide sequence (SEQ ID NO: 16) for the G-protein coupled receptor CXCR4.

FIG. 9 displays the amino acid sequence (SEQ ID NO: 17) and the nucleotide sequence (SEQ ID NO: 18) for the G-protein coupled receptor PAR2.

FIG. 10 is a schematic map of the features of the GPCR expression vector pMEX2.

FIG. 11A and FIG. 11B show the nucleotide sequence of the GPCR expression vector pMEX2.

FIG. 12 is a schematic map of the features of the GPCR expression vector pMEX5.

FIG. 13A and FIG. 13B show the nucleotide sequence of the GPCR expression vector pMEX5.

FIG. 17 provides data from a binding assay of transiently expressed histamine receptors (H2).

DETAILED DESCRIPTION OF THE INVENTION

Definitions

Figure 14:
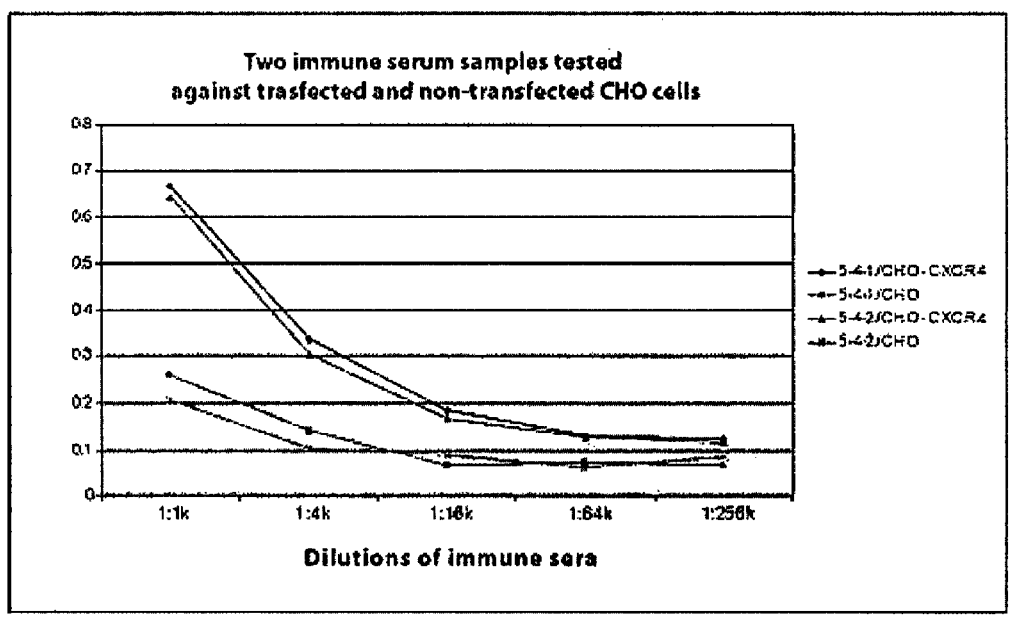
FIG. 14 displays the results of an ELISA assay of mouse immune sera collected after 3 immunizations with CXCR4 transfected cells as the immunogen.

The abbreviation "GPCR" refers to G-protein Coupled Receptor, and as used herein encompasses the protein, amino acid sequence, and nucleotide sequence encoding for a G-protein coupled receptor.

The terms "heterologous protein", "recombinant protein", and "exogenous protein" can be used interchangeably in referring to aspects of this invention. These phrases refer to a polypeptide which is produced by recombinant DNA techniques, wherein DNA encoding the polypeptide is inserted into a suitable expression vector which is in turn used to transform a host cell to produce the heterologous protein.

As used herein, "heterologous G protein coupled receptor" (e.g., a heterologous adenosine receptor) is a receptor encoded by heterologous DNA. Upon expression of the heterologous DNA in a recombinant cell, the heterologous receptor is expressed in the recombinant cell. The term heterologous G protein coupled receptor, or GPCR, as used herein encompasses wildtype proteins (and the nucleotide sequences which encode for them) as well as all variants or mutants, whether those variations or mutations are naturally-occurring or created through genetic or molecular engineering.

The term "signal transduction" encompasses the processing of physical or chemical signals from the extracellular environment through the cell membrane and into the cell, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation.

The term "functionally" couples to (as in a receptor that is "functionally integrated into a signaling pathway in a cell" or "functionally integrated into an endogenous yeast signaling pathway" or "functionally expressed by a host cell") refers to the ability of a receptor to bind to modulators and transduce that binding event into a signal using components of a signaling pathway of the cell. For example, GPCR which is functionally integrated into an endogenous pheromone response or signaling pathway of a yeast cell is expressed on the surface of the yeast cell, couples to a G protein within the yeast cell and transduces a signal in that yeast cell upon binding of a modulator to the receptor.

The term "modulation", as in "modulation of a (heterologous) G protein coupled receptor" and "modulation of a signal transduction activity of a receptor protein" encompasses, in its various grammatical forms, induction and/or potentiation, as well as inhibition and/or downregulation of receptor activity and/or one or more signal transduction pathways downstream of a receptor.

An "oligonucleotide", as used herein, refers to a stretch of nucleotide residues which preferably has a sufficient number of bases to be used as an oligomer, amplimer or probe in a polymerase chain reaction (PCR). Oligonucleotides are prepared synthetically or from genomic or cDNA sequences and are preferably used to amplify, reveal, or confirm the presence of a similar DNA or RNA in a particular cell or tissue. Oligonucleotides or oligomers comprise portions of a DNA sequence having at least about 10 nucleotides and as many as about 35 nucleotides, preferably about 25 nucleotides.

"Probes" refers to oligonucleotides derived from naturally occurring recombinant single- or double-stranded nucleic acids or may be chemically synthetic. Oligonucleotides are useful in detecting the presence of complementary identical or similar sequences. Probes may be labeled with reporter molecules using nick translation, Klenow fill-in reaction, PCR or other methods well known in the art. Nucleic acid probes may be used in Southern, Northern or in situ hybridization to determine whether DNA or RNA encoding a certain protein is present in a cell type, tissue, or organ.

A "fragment of a polynucleotide" is a nucleic acid that comprises all or any part of a given nucleotide molecule. An exemplary fragment is about 6 kb in length, preferably having fewer nucleotides than about 6 kb, more preferably having fewer than about 1 kb.

"Reporter molecules" include chemical, radionucleic, enzymatic, fluorescent, chemiluminescent, or chromogenic agents which associate with a particular nucleotide sequence, receptor, or amino acid sequence, thereby establishing the presence of or quantifying the expression of a certain sequence, receptor or agent binding to the receptor.

"Chimeric" oligonucleotides may be constructed by introducing all or part of a nucleotide sequence of this invention into a vector containing additional nucleic acid sequence which might be expected to change any one or several of the following GPCR characteristics: cellular location, distribution, ligand-binding affinities, interchain affinities, degradation/turnover rate, signaling, etc. Similarly, chimeric peptides are GPCR amino acid sequences which have been constructed to contain additional amino acid sequences which might be expected to change any one or several of the following GPCR characteristics: cellular location, distribution, ligand-binding affinities, interchain affinities, degradation/turnover rate, signaling, etc.

"Active", with respect to a GPCR, refers to those forms, fragments, or domains of a GPCR polypeptide which retain the biological and/or antigenic activity of a GPCR polypeptide.

"Naturally occurring GPCR polypeptide" refers to a polypeptide produced by cells which are not genetically engineered and specifically contemplates various polypeptides arising from post-translational modifications of the polypeptide including but not limited to acetylation, carboxylation, glycosylation, phosphorylation, lipidation and acylation.

"Derivative" refers to polypeptides which are chemically modified by techniques such as ubiquitination, labeling, pegylation (derivatization with polyethylene glycol), insertion or substitution of amino acids such as ornithine which do not normally occur in human proteins, or one or more amino acids from the wild type sequence.

"Conservative amino acid substitutions" result from replacing one amino acid with another having similar structural and/or chemical properties, such as the replacement of a leucine with an isoleucine or valine, an aspartate with a glutamate, or a threonine with a serine.

A "signal sequence" or "leader sequence" can be used, when desired, to direct the polypeptide through a membrane of a cell. Such a sequence may be naturally present on polypeptides produced using the vectors and methods of the present invention or provided from heterologous sources by recombinant DNA techniques.

"Inhibitor" is any substance which retards or prevents chemical or physiological reactions or responses. Common inhibitors include but are not limited to antisense molecules, antibodies, and antagonists.

"Standard expression" is a quantitative or qualitative measurement for comparison. It is based on a statistically appropriate number of normal samples and is created to use as a basis of comparison when performing diagnostic assays, running clinical trials, or following patient treatment profiles.

"Animal", as used herein, includes human, domestic (e.g., cats, dogs, etc.), agricultural (e.g., cows, horses, sheep, etc.) or test species (e.g., mouse, rat, rabbit, etc.).

"Stringent conditions" refers to conditions that allow for the hybridization of essentially complementary nucleic acid sequences. For instance, such conditions will generally allow hybridization of sequence with at least about 85% sequence identity, preferably with at least about 90% to 95% sequence identity, more preferably about 91% sequence identity, about 92% sequence identity, about 93% sequence identity, about 94% sequence identity, more preferably with at least about 95% to 99% sequence identity, preferably about 96% sequence identity, about 97% sequence identity, about 98% sequence identity, still more preferably about 99% sequence identity, or about 100% sequence identity to the complementary nucleic acid sequences.

"Recombinant cells" encompasses one or more individual cells as well as to a recombinant cell line in which the cells are expressing a heterologous protein.

The term "extracellular signal" encompasses molecules and changes in the cellular environment that are transduced intracellularly via cell surface proteins that interact, directly or indirectly, with the extracellular signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface receptors and modulate the activity of such receptors. The term, "extracellular signal" also includes as yet unidentified substances that modulate the activity of a cellular receptor, and thereby influence intracellular functions. Such extracellular signals are potential pharmacological agents that may be used to treat specific diseases by modulating the activity of specific cell surface receptors.

The term "functional assays" as used herein encompasses those assays that take advantage of certain aspects of GPCR protein activity or behavior under particular conditions, for example, the activation of a G protein upon binding of a ligand to the GPCR.

The term "selectively binds" as used herein refers to a compound (e.g., an antibody, a peptide, a lipid or a small organic molecule) that binds to a native polypeptide or to a chimeric polypeptide preferentially relative to other unrelated polypeptides. A compound selectively binds to the native polypeptide or a chimeric polypeptide of the invention if it has at least a 10%, preferably at least a 25%, at least a 50%, at least a 75%, at least a 90%, at least a 95%, or at least a 100% higher affinity and/or avidity for the native polypeptide or chimeric polypeptide than an unrelated polypeptide.

Introduction

G protein coupled receptors (hereinafter termed "GPCRs") comprise a large superfamily of receptors. GPCRs were originally defined as receptors that transduce signals from the extracellular compartment to the interior through biochemical processes involving GTP-binding proteins. Molecular cloning of the first receptor genes suggested protein structures with seven transmembrane α-helical domains (hence "7TM receptors"). Typical GPCRs do share a common structural motif of seven transmembrane helical domains, but some GPCRs are instead single-spanning transmembrane receptors for cytokines such as erythropoietin or insulin, or multi-polypeptide receptors such as the collagen receptor.

As used herein, "GPCR protein" and "a GPCR" refers to a protein in which one response to the binding of a ligand to the GPCR is the activation of a G protein. This term also encompasses the amino acid and nucleotide sequences of these proteins. "A GPCR" is meant to include both the singular and plural forms of the phrase, i.e., "a GPCR" may refer to one or more GPCR molecules.

Modern crystallography and mutational analyses show that GPCRs are versatile receptors for a wide range of extracellular messengers, including biogenic amines, purines and nucleic acid derivatives, lipids, peptides and proteins, odorants, pheromones, tastants, ions like calcium and protons, and photons (in the case of rhodopsin). GPCRs can form homo- and heterodimers, as well as complex receptosomes, which in some cases can incorporate additional intra- and extracellular soluble and transmembrane proteins.

GPCRs play a vital role in the signaling processes that control cellular metabolism, cell growth and motility, inflammation, neuronal signaling, and blood coagulation. G protein coupled receptor proteins also serve as targets for molecules such as hormones, neurotransmitters and physiologically active substances. Thus, GPCRs are a major target for drug action and development.

High Expression Vectors

In a first aspect, the invention provides a vector which facilitates high levels of expression of GPCR proteins in a cell line. Native GPCR proteins are expressed in levels numbering in the upper hundreds to low thousands of copies per cell. Since most molecular and cell biology techniques, such as screening assays and raising antibodies, cannot be conducted with such low levels of protein, high expression vectors are needed to produce proteins on the order of tens of thousands to millions of copies per cell. The vectors encompassed by the instant invention overcome the hurdle to GPCR research posed by the low expression of native GPCR proteins by facilitating high levels of expression of GPCR proteins in mammalian cells.

In an exemplary embodiment, according to FIG. 10, the invention provides a novel vector named pMEX2 for expression of GPCR proteins on the cytoplasmic membrane of mammalian cells. As shown in FIG. 10, this vector includes a pUC origin and a beta-lactamase gene for replication and ampicillin selection of the plasmid in bacteria. A puromycin resistance marker for maintaining the plasmid in mammalian cells is also included in certain embodiments of this vector. Expression of the gene of interest is under control of a strong CMV promoter for high-level transcription activity.

In another exemplary embodiment, according to FIG. 12, the invention provides a novel vector named pMEX5 for expression of GPCR proteins on the cytoplasmic membrane of mammalian cells. This vector allows for expression of GPCR proteins under control of an inducible promoter. As in pMEX2, pMEX5 includes a strong CMV promoter for high-level transcription activity, with the additional feature that the promoter is operably linked to a tetracycline operator, as shown in FIG. 12. In alternative embodiments of the invention, the inducible promoter may be selected from a chemical inducible promoter, such as a steroid-responsive promoter, a tissue responsive promoter, a promoter derived from the genome of mammalian cells, such as the metallothionein promoter, and a promoter derived from mammalian viruses, such as the retrovirus long terminal repeat, the adenovirus late promoter, and the vaccinia virus 7.5K promoter. Promoters produced by recombinant DNA or synthetic techniques may also be used to provide for transcription of a polypeptide-encoding nucleotide sequence.

In both the vectors pictured in FIG. 10 and FIG. 12 respectively, the vectors include Kozak consensus sequence for optimal translation initiation and an SV40 late polyadenylation signal to promote stability in the transcripts. Also included in the vectors are signal sequences (labeled "SP" in FIG. 10 and FIG. 12) which provide efficient delivery of the translated protein to the membrane of the cell. It is intended that the exemplary signal sequences shown in FIG. 10 and FIG. 12 are not meant to be limiting, and that the instant invention encompasses all possibilities of signal sequences which are effective in targeting the translated protein to the cell membrane.

In an exemplary embodiment, the invention provides binding sites for the bacteriophage DNA binding protein LexA that are engineered just upstream of the promoter sequence of the expression vector. An expression vector engineered in this way will express a chimeric protein that includes the LexA DNA binding domain linked to an activation domain, such as that for the herpes simplex virus protein VP16. In principle, this combination of DNA binding site, DNA binding protein and activation domain can be manipulated by using DNA binding sites, DNA binding proteins and/or activation domains to strengthen the ability of the promoter to initiate and sustain transcription of downstream elements in the vector.

In one embodiment of the invention, the expression vector includes a nucleotide sequence for a GPCR protein selected from one of several possible GPCR families of proteins, including: anaphylatoxin, apelin, bombesin, cannabinoid, chemokine, free fatty acid, galanin, glucagon, glycoprotein hormone, leukotriene/lipoxin, lysophospholipid, melanin-concentrating hormone, melatonin, N-formylpeptide, neuromedin U, neuropeptide S, neuropeptide W/neuropeptide B, neuropeptide Y, opioid, platelet activating factor, prolactin releasing peptide, prostanoid, PTH, purinergic, tachykinin, trace amine, and urotensin.

In another embodiment of the invention, the expression vector includes a nucleotide sequence encoding for an "orphan" GPCR, which is a GPCR protein for which there is as of yet no known ligand. There are currently over two hundred GPCR proteins identified as orphan GPCRs. These orphan proteins may be implicated in a number of disease, such as cancer and inflammation associated with arthritis, and thus orphan GPCRs are of particular interest to the pharmaceutical and biotechnology industries.

In a further embodiment of the invention, the expression vector includes a nucleotide sequence encoding for a GPCR that is a member selected from: C3aR, APJ, BB1, BB3, GPR55, CCR1, CCR5, CCR7, CCR9, CMKLR1, CXCR3, CXCR4, FFA1, FFA2, GAL1, GAL2, GAL3, GHRH, TSH, ALX, BLT1, BLT2, CysLT1, LPA2, LPA3, MCH1, MT2, FPR1, NMU1, NPS, NPS(1), NPS(2), NPS Ile107, NPBW1, NPBW2, delta, kappa, mu, NOP, GPR37L1, GPR84, MRGX1, MRGX2, PSGR, PAF, PRP, DP, EP1, GPR44, PTH2, P2Y12, NK2, NK3, TA1, C5aR, PAR2.

In a still further embodiment, the expression vector includes a GPCR protein which has an amino acid sequence that is a member selected from: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, and SEQ ID NO: 17, as pictured in FIG. 1 through FIG. 9.

In a further embodiment of the invention, the expression vector comprises a member selected from: SEQ ID NO: 19 and SEQ ID NO: 20. Vector maps graphically illustrating the expression vectors corresponding to these sequences are shown in FIG. 10 and FIG. 12 respectively. The expression vectors in one embodiment of the invention contain multiple restriction sites which can be used to insert a nucleotide sequence encoding for a GPCR.

In a further embodiment, the invention provides expression vectors that include nucleotide sequences for molecules to aid in the detection of GPCR. In a still further embodiment, such detection includes the ability to determine if the protein is expressed in the correct orientation on the cytoplasmic membrane of mammalian cells.

In a preferred embodiment, the invention provides expression vectors containing a pUC origin and a beta-lactamase gene for replication and ampicillin selection of the plasmid in bacteria. In a further embodiment of the invention, the expression vector can also include a puromycin resistance marker for the gene of interest, which is under control of a strong CMV promoter for high-level transcription activity.

In a preferred embodiment of the invention, a method is provided for creating expression vectors that enable expression of GPCRs, properly folded with appropriate post-translational modifications, with levels of expression of at least one million copies per cell on the cytoplasmic membrane. This level of expression is suitable for whole-cell immunization for raising antibodies as well as for functional and structural studies of the receptor.

Kozak Sequence

Most eukaryotic mRNAs contain a short recognition sequence that facilitates the initial binding of mRNA to the small subunit of the ribosome. The consensus sequence for initiation of translation in vertebrates (also called Kozak sequence) is: ACCATG (see, e.g., SEQ ID NO: 19, position 1099-1104). More generally it is: GCCRCCATGG where R is a purine (A or G) (see, e.g., SEQ ID NO: 19, position 1096-1105). To improve expression levels, it may be advantageous to design the cloned insert according to Kozak's rules in the present invention.

Recombinant Cells

In one aspect, the invention provides recombinant cell lines expressing GPCR proteins. In a preferred embodiment of the invention, expression of GPCR proteins is governed by a high expression vector as described above. As used herein, the terms "recombinant cell line", "cell line", "recombinant cells" can be used interchangeably to refer to cells heterologously expressing an indicated protein.

In one embodiment of the invention, the recombinant cells express levels of GPCR of at least 150,000 protein molecules per cell. In a further embodiment of the invention, GPCR is expressed at a range of 200,000 copies to 2,000,000 copies per cell. In a still further embodiment of the invention, the GPCR protein is expressed at a range of 400,000 copies to 2,000,000 copies per cell. In a still further embodiment of the invention, the recombinant cells express GPCR protein at a range of 600,000 copies to 2,000,000 copies per cell. In a yet further embodiment of the invention, the recombinant cells express GPCR protein at a range of 800,000 copies to 2,000,000 copies per cell. In a preferred embodiment of the invention, the recombinant cells express GPCR protein at a range of 1,000,000 copies to 2,000,000 copies per cell. In another preferred embodiment, the cells express GPCR protein at a range of 1,500,000 copies to 2,000,000 copies per cell.

In yet another embodiment of the invention, the GPCR protein is derived from an animal. In a further embodiment of the invention, the GPCR protein is derived from a mammal, including rat, mouse or human.

In still another embodiment of the invention, the recombinant cell expressing the GPCR protein is derived from a cell line, which may as an example be selected from a Chinese hamster ovary (CHO) cell line, a human embryonic kidney cell line (HEK293T), a C6 glioma cell line, the RH7777 cell line, the SW480 cell line from human adenocarcinoma of the colon, the VS35 cell line, the 1321N1 cell line, and other cell lines that are known in the art to be amenable to stable or transient transfection with heterologous nucleic acids.

In one aspect, the invention provides a method of producing a cell line, which includes creating at least one expression vector selected from nucleotide sequence SEQ ID NO: 19 or SEQ ID NO: 20 and transfecting a host cell with the expression vector. The transfection of the host cell can either be such that it creates a stably transfected cell line or a transiently transfected cell line by methods known in the art.

In one embodiment of the invention, the stably or transiently transfected cell line is a mammalian cell line. In a preferred embodiment, the cell line is derived from a cell line selected from a group consisting of: CHO, HEK293T, C6, RH7777, SW480, VS35, and 1321N1. Mammalian cell lines are particularly preferred, because such cell lines ensure that the protein will receive the proper post-translational modifications before being transported to the cell membrane.

GPCR-Expressing Recombinant Cells

In one embodiment, the invention provides recombinant cells expressing a GPCR protein that has an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9. In a further embodiment of the invention, the GPCR protein is a member selected from C3aR (in accordance with FIG. 6), APJ (in accordance with Accession number NM_005161), BB1 (in accordance with Accession number NM_012799), BB3 (in accordance with Accession number NM_001727), GPR55 (in accordance with Accession number NM_005683), CCR1 (in accordance with Accession number NM_000579), CCR5 (in accordance with FIG. 7), CCR7 (in accordance with Accession number NM_001838), CCR9 (in accordance with Accession number NM_006641), CMKLR1 (in accordance with Accession number NM_004072), CXCR3 (in accordance with Accession number NM_001504), CXCR4 (in accordance with FIG. 8), FFA1 (in accordance with Accession number NM_005303), FFA2 (in accordance with Accession number NM_005304), GAL1 (in accordance with Accession number NM_001480), GAL2 (in accordance with Accession number NM_003857), GAL3 (in accordance with Accession number NM_003614), GHRH (in accordance with Accession number NM_000823), TSH (in accordance with Accession number NM_012888), ALX (in accordance with Accession number NM_003857), BLT1 (in accordance with Accession number BC_004545), BLT2 (in accordance with Accession number NM_0193839.1), CysLT1 (in accordance with Accession number NM_006639), LPA2 (in accordance with Accession number NM_004724.4), LPA3 (in accordance with Accession number NM_012152.1), MCH1 (in accordance with Accession number NM_005297), MT2 (in accordance with Accession number NM_005959), FPR1 (in accordance with Accession number NM_002029), NMU1 (in accordance with FIG. 2), NPS (in accordance with Accession number NM_175678), NPS(1) (in accordance with Accession number NM_207172), NPS (2) (in accordance with Accession number NM_207173), NPS Ile107 (in accordance with Accession number SNP591694), NPBW1 (in accordance with Accession number NM_001014784 and NM_005285), NPBW2 (in accordance with Accession number NM_005286), delta (in accordance with Accession number NM_012617), kappa (in accordance with Accession number L22001), mu (in accordance with Accession number L13069), NOP (in accordance with Accession number BC038433), GPR37L1 (in accordance with Accession number NM_004767), GPR84 (in accordance with Accession number NM_020370), MRGX1 (in accordance with Accession number NM_147199), MRGX2 (in accordance with Accession number NM_054030), PSGR (in accordance with Accession number NM_030774), PAF (in accordance with Accession number NM_000952), PRP (in accordance with Accession number NM_004248), DP (in accordance with Accession number NM_000953), EP1 (in accordance with Accession number NM_000955), GPR44 (in accordance with Accession number NM_004778), PTH2 (in accordance with Accession number NM_005048), P2V 12 (in accordance with Accession number NM_022788), NK2 (in accordance with Accession number NM_001057), NK3 (in accordance with Accession number NM_175057), TA1 (in accordance with Accession number NM_138327), C5aR (in accordance with FIG. 1), PAR2 (in accordance with FIG. 9).

In another embodiment of the invention, recombinant cells express a GPCR protein encoded by a nucleotide sequence selected from SEQ ID NO: 2, SEQ ID NO: 4, SEQ ID NO: 6, SEQ ID NO: 8, SEQ ID NO: 12, SEQ ID NO: 14, SEQ ID NO: 16, and SEQ ID NO: 18, as pictured in FIG. 1 through FIG. 9. In a further embodiment of the invention, transcription of the nucleotide sequence encoding a GPCR protein is operably linked to a promoter, such as the cytomegalovirus (CMV) promoter. In a still further embodiment of the invention, the promoter is itself operably linked to an inducible operator, for example a tetracycline operator.

In another embodiment of the invention, the recombinant cells express GPCR protein at a level of at least 150,000 copies per cell. In a further embodiment, the invention provides GPCR expression levels at a range of about 150,000 copies and 2,000,000 copies per cell. In a still further embodiment, the invention provides GPCR expression levels at a range of about 200,000 copies and 2,000,000 copies per cell. In a still further embodiment, the invention provides GPCR expression levels at a range of about 300,000 copies and 2,000,000 copies per cell. In a further embodiment, the invention provides GPCR expression levels at a range of about 400,000 copies and 2,000,000 copies per cell. In a still further embodiment, the invention provides GPCR expression levels at a range of about 500,000 copies and 2,000,000 copies per cell. In a still further embodiment, the invention provides GPCR expression levels at a range of about 600,000 copies and 2,000,000 copies per cell. In a still further embodiment, the invention provides GPCR expression levels at a range of about 700,000 copies and 2,000,000 copies per cell. In a still further embodiment, the invention provides GPCR expression levels at a range of about 800,000 copies and 2,000,000 copies per cell. In a still further embodiment, the invention provides GPCR expression levels at a range of about 900,000 copies and 2,000,000 copies per cell. In a still further embodiment, the invention provides GPCR expression levels at a range of about 1,000,000 copies and 2,000,000 copies per cell. In a still further embodiment, the invention provides GPCR expression levels at a range of about 1,500,000 copies and 2,000,000 copies per cell. In a still further embodiment, the invention provides GPCR expression levels at a range of about 1,750,000 copies and 2,000,000 copies per cell.

In one aspect, the invention provides a recombinant cell line stably expressing a GPCR protein that has an amino acid sequence selected from SEQ ID NO: 1, SEQ ID NO:3, SEQ ID NO: 5, SEQ ID NO: 7, SEQ ID NO: 9, SEQ ID NO: 11, SEQ ID NO: 13, SEQ ID NO: 15, and SEQ ID NO: 17. It will be understood by those of skill in the art that these amino acid sequences encompass the nucleic acid sequences which encode for them.

Nucleotide and Amino Acid Sequences Encoding for GPCR

In preferred embodiments, the instant invention uses nucleotide and amino acid sequences encoding for GPCR proteins in functional and cell-based assays and to produce recombinant cell lines. The nucleotide sequences encoding GPCRs (or their complements) have numerous applications in techniques known to those skilled in the art of molecular biology. These techniques include their use: as hybridization probes, in the construction of oligomers for PCR, for chromosome and gene mapping, in the recombinant production of GPCR, and in generation of antisense DNA or RNA, their chemical analogs and the like. Uses of nucleotides encoding a GPCR disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of GPCR-encoding nucleotide sequences may be produced. Some of these will bear only minimal homology to the nucleotide sequence of the known and naturally occurring GPCR. The invention has specifically contemplated each and every possible variation of nucleotide sequence that could be made by selecting combinations based on possible codon choices. These combinations are made in accordance with the standard triplet genetic code as applied to the nucleotide sequence of naturally occurring GPCR, and all such variations are to be considered as being specifically disclosed.

Although the nucleotide sequences which encode a GPCR, its derivatives or its variants are preferably capable of hybridizing to the nucleotide sequence of the naturally occurring GPCR polynucleotide under stringent conditions, it may be advantageous to produce nucleotide sequences encoding GPCR polypeptides or their derivatives which posses a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence without altering the encoded amino acid sequence include the production of RNA transcripts with certain desirable properties, such as an increased half-life or greater specificity than is possible with the naturally occurring sequence.

Nucleotide sequences encoding GPCR polypeptides may be joined to a variety of other nucleotide sequences by means of well established recombinant DNA techniques. Useful nucleotide sequences for joining to GPCR-encoding polynucleotides include an assortment of cloning vectors such as plasmids, cosmids, lambda phage derivatives, phagemids, and the like. Vectors of interest include expression vectors, replication vectors, probe generation vectors, sequencing vectors, etc. In general, vectors of interest may contain an origin of replication functional in at least one organism, convenient restriction endonuclease sensitive sites, and selectable markers for one or more host cell systems.

It will be recognized that many deletional or mutational analogs of GPCR polynucleotides will be effective hybridization probes for GPCR polynucleotides. Accordingly, the invention relates to nucleic acid sequences that hybridize with such GPCR encoding nucleic acid sequences under stringent conditions.

Hybridization conditions and probes can be adjusted in well-characterized ways to achieve selective hybridization of human-derived probes. Examplary stringent conditions, include a buffer containing 1 mM EDTA, 0.5 M NaHPO$_4$ (pH 7.2), 7% (w/v) SDS.

Nucleic acid molecules that will hybridize to GPCR polynucleotides under stringent conditions can be identified functionally. Without limitation, examples of hybridization probes include probes and primers used for identifying tissues that express GPCR, measuring mRNA levels, for instance to identity a sample's tissue type or to identify cells that express abnormal levels of GPCR, and detecting polymorphisms of GPCR.

It is possible to produce a DNA sequence, or portions thereof, entirely by synthetic chemistry. After synthesis, the nucleic acid sequence can be inserted into any of the many available DNA vectors and their respective host cells using techniques known in the art. Moreover, synthetic chemistry may be used to introduce mutations into a nucleotide sequence. A portion of sequence in which a mutation is desired can also be synthesized and recombined with longer portion of an existing genomic or recombinant sequence.

GPCR polynucleotides may be used to produce a purified oligo- or polypeptide using well known methods of recombinant DNA technology. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Sequences encoding GPCR can be synthesized, in whole or in part, using chemical methods well known in the art. Alternatively, GPCR itself can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer). Optionally, fragments of GPCR can be separately synthesized and combined using chemical methods to produce a full-length molecule.

The newly synthesized peptide can be substantially purified by preparative high performance liquid chromatography. The composition of a synthetic GPCR can be confirmed by amino acid analysis or sequencing. Additionally, any portion of the amino acid sequence of GPCR can be altered during direct synthesis and/or combined using chemical methods with sequences from other proteins to produce a variant polypeptide or a fusion protein.

As will be understood by those of skill in the art, it may be advantageous to produce GPCR polynucleotides possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences referred to herein can be engineered using methods generally known in the art to alter GPCR polynucleotides for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Similarly, the polypeptide sequences referred to herein can be engineered or modified, preferably with post-translational modification that occur in the naturally occurring polypeptides, such as glycosylation.

Antibodies

In one aspect, the invention provides an antibody or antigen binding fragment that specifically binds to a structural feature of a GPCR protein. Such an antibody or antigen binding fragment is raised against an immunogen, which in a further aspect of the invention is a cell line expressing between 150,000 and 2,000,000 copies of GPCR protein per cell. In one embodiment of the invention, the antibody or antigen binding fragment is a monoclonal antibody or antigen binding fragment.

In one embodiment of the invention, the antibody or antigen binding fragment binds to a structural feature of a GPCR protein which is a member of a GPCR family selected from anaphylatoxin, apelin, bombesin, cannabinoid, chemokine, free fatty acid, galanin, glucagon, glycoprotein hormone, leukotriene/lipoxin, lysophospholipid, melanin-concentrating hormone, melatonin, N-formylpeptide, neuromedin U, neuropeptide S, neuropeptide W/neuropeptide B, neuropeptide Y, opioid, platelet activating factor, prolactin releasing peptide, prostanoid, PTH, purinergic, tachykinin, trace amine, and urotensin.

In a further embodiment, the invention provides an antibody or antigen binding fragment which is raised against a cell line expressing a member of a GPCR-family selected from C3aR, APJ, BB1, BB3, GPR55, CCR1, CCR5, CCR7, CCR9, CMKLR1, CXCR3, CXCR4, FFA1, FFA2, GAL1, GAL2, GAL3, GHRH, TSH, ALX, BLT1, BLT2, CysLT1, LPA2, LPA3, MCH1, MT2, FPR1, NMU1, NPS, NPS(1), NPS(2), NPS Ile107, NPBW1, NPBW2, delta, kappa, mu, NOP, GPR37L1, GPR84, MRGX1, MRGX2, PSGR, PAF, PRP, DP, EP1, GPR44, PTH2, P2Y12, NK2, NK3, TA1, C5aR, and PAR2. In a still further embodiment, the antibody or antigen binding fragment recognizes an epitope on a GPCR protein selected from C3aR, APJ, BB1, BB3, GPR55, CCR1, CCR5, CCR7, CCR9, CMKLR1, CXCR3, CXCR4, FFA1, FFA2, GAL 1, GAL2, GAL3, GHRH, TSH, ALX, BLT1, BLT2, CysLT1, LPA2, LPA3, MCH1, MT2, FPR1, NMU1, NPS, NPS(1), NPS(2), NPS Ile107, NPBW1, NPBW2, delta, kappa, mu, NOP, GPR37L1, GPR84, MRGX1, MRGX2, PSGR, PAF, PRP, DP, EP1, GPR44, PTH2, P2Y12, NK2, NK3, TA1, C5aR, and PAR2.

In another embodiment, the invention provides an antibody or antigen binding fragment which is raised against a cell line expressing a member of GPCR family having an amino acid sequence selected from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, and SEQ ID NO: 17.

In a further embodiment, the invention provides an antibody or antigen binding fragment that binds to a structural feature of a GPCR protein and is raised against an immunogen which is a cell line expressing at least about 150,000 copies of a GPCR protein per cell. In a preferred embodiment, the cell line expresses about 500,000 copies of a GPCR protein per cell. In a particularly preferred embodiment, the cell line expresses between about 1,000,000 and about 2,000,000 copies of a GPCR protein per cell.

In one aspect, the invention provides a method for producing monoclonal antibodies for a GPCR protein. This method includes immunizing a test animal with at least one cell line expressing a member of a GPCR family. In accordance with the invention, this cell line expresses at least about 150,000 copies of said GPCR protein per cell. The test animal is induced to produce hybridomas, which are isolated. The method also includes screening for monoclonal antibodies using one or more cell-based assay systems. In one embodiment of the invention, the cell-based assay systems used to screen for monoclonal antibodies are selected from a group consisting of: FACS, ELISA, calcium imaging, FLIPR, multiplex ligand binding, and electrophysiology.

In one embodiment of the invention, monoclonal antibodies are induced in a test animal selected from a group comprising: rabbit, mouse, rat, pig, dog, monkey and goat. In a preferred embodiment, the invention provides a method of immunizing the test animal with whole cells expressing said member of GPCR family. In accordance with the invention, the whole cells used to immunize the test animal express at least 150,000 copies of the member of the GPCR family per cell.

GPCRs have traditionally been good drug targets for small molecule compounds and peptides. The field of antibody therapeutics for GPCRs is still in early-stage clinical trials. However, cases where small ligands can not be obtained, such as for example, Family II GPCRs, monoclonal antibodies can provide a viable alternative approach. Monoclonal antibodies may bind and lock GPCR in its active form and function as agonists. In addition, since the extracellular domains of GPCRs are more diverse than the rest of GPCR proteins including the transmembrane domains that small molecule compounds typically bind, monoclonal antibodies may bind to GPCRs more specifically than small molecules and thus can better distinguish subtle sequence and structural differences within sub-family members. Since GPCRs are also known to be overexpressed in many tumors, an advantage of GPCR antibody therapeutics is their ability to act as targeting moieties, guiding specific and accurate destruction of cancer cells.

Kits

In one aspect, the invention provides a kit for high throughput purification and quantification of a plurality of recombinant proteins of one or more members of GPCR family. The kit includes a vector for expressing said recombinant proteins in host cells, wherein said vector comprises SEQ ID NO: 19 or 20, an affinity chromatography resin, a proteolytic enzyme, an internal quantification standard, a matrix for MALDI-TOF mass spectrometry, and instructions for use. In one embodiment, the invention further provides a kit that also includes at least one buffer selected from the group consisting of a lysis buffer; a denaturing buffer; an affinity chromatography binding buffer; an affinity chromatography washing buffer; an affinity chromatography elution buffer; and a proteolytic digestion buffer.

In another embodiment, the invention provides a kit for high throughput purification and quantification that includes at least one multi-well plate. In yet another embodiment, the invention provides a kit for high throughput purification and quantification which includes a partially or fully automated high throughput purification and quantification system.

In a further embodiment, the invention provides a kit which includes a vector that induces expression of one or more members of one or more GPCR families at a level of at least about 150,000 copies per cell. In a preferred embodiment, the vector induces between 150,000 and 2,000,000 copies of the GPCR protein per cell.

Screening Methods

In one aspect, the invention provides methods for screening for therapeutic candidates. These methods include the use of a recombinant cell expressing a GPCR protein, where a test entity is contacted with the recombinant cell, and binding is detected between the test entity and the GPCR protein. As an embodiment of the invention, specific binding activity of the test entity to the GPCR protein identifies that test entity as a therapeutic candidate. The recombinant cell in this method expresses at least about 150,000 copies of the GPCR protein per cell. In a further embodiment of the invention, the test entity is contacted with a membrane extract of said recombinant cell. In a preferred embodiment of the invention, the method of screening for a therapeutic candidate employs a high throughput screen for detecting binding of the test entity to the GPCR protein. In a particularly preferred embodiment, the high throughput screen is partially or fully automated.

In one embodiment, the method for screening for therapeutic candidates includes a detection of binding of the test entity to the GPCR protein by means of a fluorescent, chemical, radiological, or enzymatic reporter molecule.

In an embodiment of the invention, the therapeutic candidate is screened for the treatment of cancer or of an illness associated with inflammation. In a preferred embodiment of the invention, the therapeutic candidate is screened for treatment of breast cancer.

In one aspect, the invention provides a method for identifying DNA sequences encoding a member of a GPCR family, which includes probing a cDNA library or a genomic library with a labeled probe with a nucleotide sequence selected from SEQ ID NO: 2, 4, 6, 8, 10, 12, 14, 16, and 18. DNA sequences from the library that are able to hybridize to the probe under stringent conditions are thus identified as encoding a member of a GPCR family. In an embodiment of the invention, the cDNA library or genomic library is derived from human tissue. In a particularly preferred embodiment, the human tissue used to create the cDNA or genomic library includes cancerous cells.

In one embodiment, the invention provides methods of using recombinant cell lines expressing the vectors of the present invention to prepare cDNA libraries of GPCRs. Such high expressing cells will be rich in GPCRs, which can in one embodiment of the invention be screened by low-stringency hybridization, or, alternatively, used in a polymerase chain reaction for amplification of candidate genes using degenerate polymers. Proof-of-function can obtained after the expression of the cloned receptor in heterologous cells with an elicited agonist response.

The compounds tested as modulators of GPCRs can be any small chemical compound, or a biological entity, e.g., a macromolecule such as a protein, sugar, nucleic acid or lipid. Alternatively, modulators can be genetically altered versions of GPCR. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

Blinding Assays

The instant invention provides binding assays using recombinant cell lines claimed and described herein. Candidate or test compounds or agents which bind to GPCR and/or have a stimulatory or inhibitory effect on the activity or the expression of GPCR are identified either in assays that employ cells which express GPCR on the cell surface (cell-based assays) or in assays with isolated GPCR (cell-free assays). The various assays can employ a variety of variants of GPCR (e.g., full-length GPCR, a biologically active fragment of GPCR, or a fusion protein which includes all or a portion of GPCR). Moreover, GPCR can be derived from any suitable mammalian species (e.g., human GPCR, rat GPCR or murine GPCR). The assay can be a binding assay entailing direct or indirect measurement of the binding of a test compound or a known GPCR ligand to GPCR. The assay can also be an activity assay entailing direct or indirect measurement of the activity of GPCR.

In one embodiment, the invention provides assays for screening candidate or test compounds which bind to or modulate the activity of a membrane-bound (cell surface expressed) form of GPCR. Such assays can employ full-length GPCR, a biologically active fragment of GPCR, or a fusion protein which includes all or a portion of GPCR. Such test compounds can be obtained by any suitable means, e.g., from conventional compound libraries. Determining the ability of the test compound to bind to a membrane-bound form of GPCR can be accomplished, for example, by coupling the test compound with a radioisotope or enzymatic label such that binding of the test compound to the GPCR expressing cell can be measured by detecting the labeled compound in a complex. For example, the test compound can be labeled with $^{125}I$, $^{35}S$, $^{14}C$, or $^{3}H$, either directly or indirectly, and the radioisotope detected by-direct counting of radio-emission or by scintillation counting. Alternatively, the test compound can be enzymatically labeled with, for example, horseradish peroxidase, alkaline phosphatase, or luciferase, and the enzymatic label detected by determination of conversion of an appropriate substrate to product.

Binding assays can also be used to detect receptor-mediated G-protein activation (see, e.g., "Regulation of G Protein-Coupled Receptor Function and Expression" ed. Benovic, J. L. pp 119 132, 2000, Wiley-Liss, New York). Such assays include receptor-stimulated GTP Binding to G.alpha. subunits. Activation of GPCR results in GDP-GTP exchange in the G.alpha. subunit, and this exchange can be quantified and used as a direct measurement of receptor-G protein interaction. This typically involves the use of radiolabelled guanine nucleotide with the receptor either in cell free membrane preparations or artificial lipid membranes. The amount of radiolabel incorporated is used as a measure of the extent of G protein activation.

Receptor-G-protein interactions can also be examined. For example, in the absence of GTP, an activator will lead to the formation of a tight complex of a G protein (all three subunits) with the receptor. This complex can be detected in a variety of ways, as noted above. Such an assay can be modified to search for inhibitors. Adding an activator to the receptor and G protein in the absence of GTP, can be used to screen for inhibitors through measurements of the dissociation constants of the receptor-G protein complex. In the presence of GTP, release of the alpha subunit of the G protein from the other two G protein subunits serves as a criterion of activation.

Ligand binding to GPCR, a domain of a GPCR protein, or a chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties, as well as other techniques known in the art.

Other useful binding assays utilize changes in intrinsic tryptophan fluorescence of protein subunits. The intrinsic fluorescence of tryptophan residues undergoes an enhancement during GDP-GTP exchange. Such an enhancement can be detected using methods known in the art.

The assay can also be an expression assay entailing direct or indirect measurement of the expression of GPCR mRNA or GPCR protein. The various screening assays are combined with an in vivo assay entailing measuring the effect of the test compound on the symptoms of hematological and cardiovascular diseases, disorders of the peripheral and central nervous system, COPD, asthma, genito-urological disorders and inflammation diseases.

In a competitive binding format, binding assays comprise contacting GPCR expressing cell with a known compound which binds to GPCR to form an assay mixture, contacting the assay mixture with a test compound, and determining the ability of the test compound to interact with the GPCR expressing cell, wherein determining the ability of the test compound to interact with the GPCR expressing cell comprises determining the ability of the test compound to preferentially bind the GPCR expressing cell as compared to the known compound.

In another embodiment, the assay is a cell-based assay comprising contacting a cell expressing a membrane-bound form of GPCR (e.g., full-length GPCR, a biologically active fragment of GPCR, or a fusion protein which includes all or a portion of GPCR) expressed on the cell surface with a test compound and determining the ability of the test compound to modulate (e.g., stimulate or inhibit) the activity of the membrane-bound form of GPCR. Determining the ability of the test compound to modulate the activity of the membrane-bound form of GPCR can be accomplished by any method suitable for measuring the activity of a G-protein coupled receptor or other seven-transmembrane receptors. The activity of a seven-transmembrane receptors can be measured in a number of ways, not all of which are suitable for any given receptor. Among the measures of activity are: alteration in intracellular $Ca^{2+}$ concentration, activation of phospholipase C, alteration in intracellular inositol triphosphate QP3) concentration, alteration in intracellular diacylglycerol (DAG) concentration, and alteration in intracellular adenosine cyclic 3',5'-monophosphate (cAMP) concentration.

The cell-free assays of the present invention are amenable to use with either a membrane-bound form of a GPCR or a soluble fragment thereof. In the case of cell-free assays comprising the membrane-bound form of the polypeptide, it may be desirable to utilize a solubilizing agent such that the membrane-bound form of the polypeptide is maintained in solution. Examples of such solubilizing agents include but are not limited to non-ionic detergents such as n-octylglucoside, n-dodecyl-glucoside, n-dodecylmaltoside, octanoyl-N-methylglucamide, decanoyl-N-methyl-glucamide, Triton X-100, Triton X-114, Thesit, Isotridecypoly(ethylene glycol ether)n, 3-[(3-cholamidopropyl)dimethylamminio]-1-propane sulfonate (CRAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In some embodiments of the assays used in accordance with the present invention, it may be desirable to immobilize GPCR (or a GPCR target molecule) to facilitate separation of complexed from uncomplexed forms of one or both of the proteins, as well as to accommodate automation of the assay. Binding of a test compound to GPCR, or interaction of GPCR with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase (GST) fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or GPCR, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of GPCR can be determined using standard techniques.

In binding assays, either the test compound or the GPCR polypeptide can comprise a detectable label, such as a fluorescent, radioisotopic, chemiluminescent, or enzymatic-label, such as horseradish peroxidase, alkaline phosphatase, or luciferase. Detection of a test compound which is bound to GPCR polypeptide can then be accomplished, for example, by direct counting of radioemmission, by scintillation counting, or by determining conversion of an appropriate substrate to a detectable product. Alternatively, binding of a test compound to a GPCR polypeptide can be determined without labeling either of the interactants. For example, a microphysiometer can be used to detect binding of a test compound with a GPCR polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and GPCR [Haseloff, (1988)].

In another embodiment of the invention, a GPCR-like polypeptide can be used as a "bait protein" in a two-hybrid assay or three-hybrid assay [Szabo, (1995); U.S. Pat. No. 5,283,317), to identify other proteins which bind to or interact with GPCR and modulate its activity. Methods for detecting such complexes, in addition to those described above for the GST-immobilized complexes, include immunodetection of complexes using antibodies which specifically bind to GPCR polypeptide or test compound, enzyme-linked assays which rely on detecting an activity of GPCR polypeptide, and SDS gel electrophoresis under non-reducing conditions.

Functional Assays

In one aspect, the invention provides methods for producing functional assay cell lines. These methods include producing cell lines expressing GPCR proteins encoded for by nucleotide sequences selected from SEQ ID NO: 2, 4, 6, 8, 10, 12, 14, 16, and 18. A functional reporter is coupled to the binding of a ligand to the GPCR protein, such that a binding event between said ligand and said GPCR protein is detectable as a reporter activity readout. In a preferred embodiment of the invention, the cell line expressing GPCR proteins is expressing at levels of at least 150,000 copies of GPCR protein per cell.

In one embodiment, the reporter readout that is detectable upon binding of a ligand to the GPCR protein includes detection of second messenger activity. In a preferred embodiment, the second messenger activity includes a change in intracellular calcium levels, cAMP activity, and/or NFAT or CRE driven beta-lactamase.

In another embodiment, the reporter activity readout includes detection of GFP, luciferase, and of a radio-labeled molecule.

In a second aspect, the invention provides a method of using a GPCR-expressing cell line to identify a test compound which modulates activity of said GPCR. In this method, second messenger activity is measured in a cell line in the absence of said test compound—this constitutes the first measurement. A second measurement is made of second messenger activity in the presence of a test compound. A comparison of the first and second measurement that shows that there is a difference between the first measurement and the second measurement identifies the test compound as an agent modulates the activity of the GPCR. In accordance with the invention, the cell line expresses at least 150,000 copies of the GPCR protein per cell.

In a preferred embodiment, the second messenger activity measured to determine if a test compound modulates GPCR activity includes a change in intracellular calcium and a change in intracellular cAMP levels. In another preferred embodiment, the detection of second messenger activity includes high throughput screening methods.

In one embodiment of the invention, an affinity tag is attached to a GPCR protein, allowing for detection of the protein when expressed on the cellular membrane. With such an affinity tag, fluorescence-activated cell sorting (FACS) can be used for both detection as well as to quantify protein expression. In a further embodiment of the invention, FACS screening makes use of an anti-tag monoclonal antibody for both detection and quantification. In another embodiment of the invention, recombinant receptors are similarly analyzed using radio-labeled ligands combined with binding assays.

Flow cytometry is a method that can be utilized to detect surface expression of GPCRs. In traditional flow cytometry, it is common to analyze very large numbers of eukaryotic cells in a short period of time. Newly developed flow cytometers can analyze and sort up to 20,000 cells per second. In a typical flow cytometer, individual particles pass through an illumination zone and appropriate detectors, gated electronically, measure the magnitude of a pulse representing the extent of light scattered. The magnitude of these pulses are sorted electronically into "bins" or "channels", permitting the display of histograms of the number of cells possessing a certain quantitative property as a function of channel number (Davey and Kell, 1996). It has been shown that the data accruing from flow cytometric measurements can be analyzed (electronically) rapidly enough that electronic cell-sorting procedures could be used to sort cells with desired properties into separate "buckets", a procedure usually known as fluorescence-activated cell sorting (Davey and Kell, 1996).

Fluorescence-activated cell sorting (FACS) is often used in studies of human and animal cell lines and the control of cell culture processes. Fluorophore labeling of cells and measurement of the fluorescence can provide quantitative data about specific target molecules or subcellular components and their distribution in the cell population. Flow cytometry can quantitate virtually any cell-associated property or cell organelle for which there is a fluorescent probe (or natural fluorescence). The parameters which can be measured have previously been of particular interest in animal cell culture.

FACS machines have been employed in the present invention to analyze the success of various expression vectors and recombinant cell lines in producing high levels of GPCR proteins. Detection and counting capabilities of the FACS system are also encompassed in the methods of the present invention.

Measuring Intracellular Calcium Levels

In one embodiment of the invention, measurement of intracellular calcium levels provides an indication of second messenger activity. Methods of measuring intracellular calcium are known to those of skill in the art. For instance, a commonly used technique is the expression of receptors of interest in *Xenopus laevis* oocytes followed by measurement of calcium activated chloride currents (see Weber, 1999, Biochim Biophys Acta 1421:213 233). In addition, several calcium sensitive dyes are available for the measurement of intracellular calcium. Such dyes can be membrane permeant or non-membrane permeant. Examples of useful membrane permeant dyes include acetoxymethyl ester forms of dyes that can be cleaved by intracellular esterases to form a free acid, which is no longer membrane permeant and remains trapped inside a cell. Dyes that are non-membrane permeant can be introduced into the cell by microinjection, chemical permeabilization, scrape loading and similar techniques (Haughland, 1993, in "Fluorescent and Luminescent Probes for Biological Activity" ed. Mason, W. T. pp 34 43; Academic Press, London; Haughland, 1996, in "Handbook of Fluorescent Probes and Research Chemicals", sixth edition, Molecular Probes, Eugene, Oreg.).

Included in the present invention are assays designed to directly measure levels of cAMP produced upon modulation of adenylate cyclase activity by GPCRs. Such assays are based on the competition between endogenous cAMP and exogenously added biotynilated cAMP. The capture of cAMP is achieved by using a specific antibody conjugated to a solid material such as capture beads. Such assays are efficient at measuring both agonist and antagonist activities.

Other assays can involve determining the activity of receptors which, when activated, result in a change in the level of intracellular cyclic nucleotides, e.g., cAMP or cGMP, by activating or inhibiting downstream effectors such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., Proc. Natl. Acad. Sci. U.S.A. 88:9868-9872 (1991) and Dhallan et al., Nature 347:184-187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm. In one embodiment, changes in intracellular cAMP or cGMP can be measured using immunoassays.

Other screening techniques include the use of cells which express GPCR (for example, transfected CHO cells) in a system which measures extracellular pH changes caused by receptor activation [Iwabuchi, (1993)].

Functional Assay Panels

In one aspect, the present invention provides a series of functional assay panels for use in screening for modulators of GPCRs for various applications, such as for therapeutics for treatment and diagnosis of illnesses associated with GPCR activity.

The functional assay panels of the present invention are based on stable cell lines expressing different classes of GPCR. These cell lines are used as a source of representative targets for surveying drug candidate specificity in functional assays such as calcium influx. These assay panels typically include forty to fifty different GPCR-expressing cell lines, but can include upwards of 300 cell lines. In addition, these panels can be customized to screen particular compounds against GPCR expressing cell lines, such as those cell lines expressing GPCRs known to be involved in certain illnesses.

In one embodiment, samples are assigned a relative GPCR activity value of 100. Inhibition of GPCR is achieved when the GPCR activity value relative to control is about 90%, optionally 50%, optionally 25-0%. Activation of an GPCR is achieved when the GPCR activity value relative to the control is 110%, optionally 150%, 200-500%, or 1000-2000%.

Assays for mRNA

In one embodiment of the invention, transcription levels can be measured to assess the effects of a test compound on signal transduction. A host cell containing the protein of interest is contacted with a test compound for a sufficient time to effect any interactions, and then the level of gene expression is measured. The amount of time to effect such interactions may be empirically determined, such as by measuring the level of transcription as a function of time. The amount of transcription may be measured by using methods known to those of skill in the art. For example, mRNA expression of the protein of interest may be detected using Northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, firefly luciferase, bacterial luciferase, .beta.-galactosidase and alkaline phosphatase. Furthermore, the protein of interest can be used as an indirect reporter via attachment to a second reporter such as green fluorescent protein (see, e.g., Mistili & Spector, Nature Biotechnology 15:961-964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA.

Solid State and Soluble High Throughput Assays

In one embodiment the invention provides soluble assays using molecules corresponding to GPCR protein domains, such as ligand binding domain, an extracellular domain, a transmembrane domain (e.g., one comprising seven transmembrane regions and cytosolic loops), and a cytoplasmic domain, an active site, a subunit association region, etc. Such domains may be covalently linked to a heterologous protein to create a chimeric molecule. In another embodiment, the invention provides solid phase based in vitro assays in a high throughput format, where the domain, chimeric molecule, GPCR, or cell or tissue expressing an GPCR is attached to a solid phase substrate.

In certain high throughput assays, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators.

The molecule of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the signal transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.)

Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of antibodies are commercially available and described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, The Adhesion Molecule Facts Book I (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences of between about 5 and 200 amino acids. Such flexible linkers are known to persons of skill in the art. For example, poly (ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, J. Am. Chem. Soc. 85:2149-2154 (1963) (describing solid phase synthesis of, e.g., peptides); Geysen et al., J. Immun. Meth. 102:259-274 (1987) (describing synthesis of solid phase components on pins); Frank & Doring, Tetrahedron 44:60316040 (1988) (describing synthesis of various peptide sequences on cellulose disks); Fodor et al., Science, 251:767-777 (1991); Sheldon et al., Clinical Chemistry 39(4):718-719 (1993); and Kozal et al., Nature Medicine 2(7):753759 (1996) (all describing arrays of biopolymers fixed to solid substrates). Non-chemical approaches for fixing tag binders to substrates include other common methods, such as heat, cross-linking by UV radiation, and the like.

Treatment of Disease

In one aspect, the invention provides a method of treating a condition associated with a GPCR protein. Such a method involves administering to a subject in need of such treatment an effective amount of an antibody that specifically binds to a structural feature of a GPCR protein. In a preferred embodiment of the invention, the antibody is raised against a cell line expressing at least 150,000 copies of a GPCR protein per cell.

In one embodiment of the invention, the treatment involves administering an effective amount of an antibody that is conjugated to a therapeutic entity. In a preferred embodiment of the invention, the antibody is conjugated to an anti-cancer therapeutic entity.

In one embodiment of the invention, the condition requiring treatment that is associated with a GPCR protein is neoplastic growth.

In another embodiment of the invention, the condition requiring treatment that is associated with a GPCR protein is breast cancer.

In still another embodiment, an element or symptom of the condition requiring treatment that is associated with a GPCR protein is inflammation.

Drug Discovery

In one aspect, the invention provides methods for targeted drug discovery and pharmaceutical design based on secondary and tertiary structures of GPCR proteins. In one embodiment of the invention, structural information on a GPCR protein is obtained from a study of proteins isolated from cells expressing at least 150,000 copies of the GPCR protein per cell.

Modulators of GPCR activity may be tested using GPCR polypeptides. The polypeptide can be isolated, expressed in a cell, expressed in a membrane derived from a cell, expressed in tissue or in an animal, either recombinant or naturally occurring. For example, breast cancer cells, normal prostate epithelial cells, placenta, testis tissue, transformed cells, or membranes can be used. Signal transduction can also be examined in vitro with soluble or solid state reactions, or by using a chimeric molecule such as an extracellular domain of a receptor covalently linked to a heterologous signal transduction domain, or with a heterologous extracellular domain covalently linked to the transmembrane and or cytoplasmic domain of a receptor. Gene amplification can also be examined. Furthermore, ligand-binding domains of the protein of interest can be used in vitro in soluble or solid state reactions to assay for ligand binding.

Test compounds can be tested for the ability to increase or decrease GPCR activity of a GPCR polypeptide. The GPCR activity can be measured after contacting either a purified GPCR, a cell membrane preparation, or an intact cell with a test compound. A test compound which decreases GPCR activity by at least about 10, preferably about 50, more preferably about 75, 90, or 100% is identified as a potential agent for decreasing GPCR activity. A test compound which increases GPCR activity by at least about 10, preferably about 50, more preferably about 75, 90, or 100% is identified as a potential agent for increasing GPCR activity.

GPCR-Directed Compound Libraries

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical and biochemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication NO: WO 91/19735), encoded peptides (e.g., PCT Publication WO 93/20242), random bio-oligomers (e.g., PCT Publication NO: WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem. Tech, Louisville Ky., Symphony, Rainin, Wobum, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Lead-finding libraries can follow molecular mimicry principles and use the substantial medicinal chemistry knowledge that has been generated during the last decade around GPCR compounds. Also useful in drug design are lead/drug likeness and computational combinatorial library design.

Studies suggest that certain classes and structural properties of ligands are important in designing drugs for particular receptors. For example, divalent ligands often selectively target opioid receptor heterodimers, while protein mimetics with $\beta$-turn/$\alpha$-helix domains are important features for drugs mimicking hormones such as somatostatin and angiotensin. Cyclic $\alpha$-peptides and $\beta$/$\gamma$ peptides may also serve as a basis for drug design for some GPCRs.

The use of privileged substructures or molecular master keys that are target-class-specific or that mimic protein secondary structure elements is a commonly used strategy in the art. The privileged-structure approach utilizes molecular scaffolds or selected substructures able to provide high-affinity ligands for diverse receptor targets. Empirically derived privileged structures include spiropiperidines, biphenyl-tetrazoles, benzimidazoles, and benzofurans. Chemoinformatics methods may also enable the automatic identification and extraction of privileged structures, which is particularly important for developing knowledge from high throughput screening data. Software such as Scitegic Pipeline Pilot can also be used to generate a data-pipelining protocol that generates frequency analysis based on the input of different reference sets.

Thematic analysis may also be used to develop drugs for GPCR proteins. In this method, a class of proteins, such as a GPCR family, is analyzed to develop a classification based on the pairing of "sequence themes" and ligand structural motifs. A sequence theme is a consensus collection of amino acids within the central binding cavity, and a motif is a specific structural element binding to such a particular microenvironment of the binding site. This compilation of themes and motifs can then be used to generate focused discovery libraries and to increase the lead optimization efficiency for the drug targets.

Individual compound libraries that target subsets of GPCRs, such as orphan receptors, share a predefined combination of themes consisting of a central dominant theme and peripheral ancillary themes. The library scaffold can then be designed to complement the central theme, with incorporation of a variety of structural motifs that address the individual sequence themes. Such libraries, consisting of approximately 1000 compounds, can then be thought of as representing a number of predefined themes which are either present or absent in a given receptor. This "fingerprinting" approach allows a score to be assigned to a particular library of compounds as to appropriateness of that group of compounds for a particular receptor. Thematic analysis could also be used to develop new combinations of used and unused themes to increase affinity and selectivity of lead compounds in a pipeline.

Other design strategies include related computer-assisted drug design, which makes use of selected reference compound sets and molecular descriptors together with cheminformatics methods to compare and rank the similarity of designed candidate molecules. Homology-based similarity searching can also identify potential ligands for orphan receptors. Artificial neural networks, self-organizing maps, and support vector machines may also be used in the drug design process—these methods align chemical and biological spaces based on mapping procedures to determine which parts of the chemical-property space correspond to specific target-families or therapeutic activities.

Administration and Pharmaceutical Compositions

GPCR modulators can be administered directly to the mammalian subject for modulation of signal transduction in vivo, e.g., for the treatment of a cancer such as breast cancer. Administration is by any of the routes normally used for introducing a modulator compound to the tissue to be treated. GPCR modulators can be administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17.sup.th ed. 1985)).

GPCR modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, by orally, topically, intravenously, intraperitoneally, intravesically or intrathecally. Optionally, the compositions are administered orally or nasally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. Such doses are administered prophylactically or to an individual already suffering from the disease. The compositions are administered to a patient in an amount sufficient to elicit an effective protective or therapeutic response in the patient. An amount adequate to accomplish this is defined as "therapeutically effective dose." The dose will be determined by the efficacy of the particular GPCR modulators (e.g., GPCR antagonists and anti-GPCR antibodies) employed and the condition of the subject, as well as the body weight or surface area of the area to be treated. The size of the dose will also be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicities, and the production of anti-modulator antibodies. In general, the dose equivalent of a modulator is from about 1 ng/kg to 10 mg/kg for a typical subject.

GPCR modulators of the present invention can be administered at a rate determined by the LD-50 of the modulator, and the side-effects of the inhibitor at various concentrations, as applied to the mass and overall health of the subject. Administration can be accomplished via single or divided doses.

Purification of GPCRs from Recombinant Cells

Recombinant proteins are expressed by transformed bacteria or eukaryotic cells such as CHO cells or insect cells in large amounts, typically after promoter induction, but expression can be constitutive. Promoter induction with IPTG is a one example of an inducible promoter system. Cells are grown according to standard procedures in the art. Fresh or frozen cells can be used for isolation of protein.

Proteins expressed in bacteria may form insoluble aggregates ("inclusion bodies"). Several protocols are suitable for purification of GPCR inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternative methods of lysing bacteria are apparent to those of skill in the art (see, e.g., Sambrook et al., supra; Ausubel et al., supra).

If necessary, inclusion bodies are solubilized, and the lysed cell suspension is typically centrifuged to remove unwanted insoluble matter. Proteins that form inclusion bodies may be renatured by elution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. The GPCR is separated from other bacterial proteins by standard separation techniques, e.g., with Ni-NTA agarose resin.

It is also possible to purify the GPCR from bacteria periplasm. After lysis of the bacteria, when the GPCR is exported into the periplasm of the bacteria, the periplasmic fraction of the bacteria can be isolated by cold osmotic shock, as well as by other methods known to those of skill in the art. To isolate recombinant proteins from the periplasm, the bacterial cells are centrifuged to form a pellet. The pellet is resuspended in a buffer containing 20% sucrose. To lyse the cells, the bacteria are centrifuged and the resultant pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of GPCR can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed.

Column Chromatography

GPCRs can also be separated from other proteins on the basis of its size, net surface charge, hydrophobicity, and affinity for ligands using techniques of column chromatography known in the art. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Suitable test compounds for use in the screening assays of the invention can be obtained from any suitable source, e.g., conventional compound libraries. The test compounds can also be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds [Lam, (1997)]. Examples of methods for the synthesis of molecular libraries can be found in the art. Libraries of compounds may be presented in solution or on beads, bacteria, spores, plasmids or phage.

Quantification of Protein Production

Western blot (immunoblot) analysis can be used to detect and quantify the presence of -GPCR in the sample. The technique generally comprises separating sample proteins by gel electrophoresis on the basis of molecular weight, transferring the separated proteins to a suitable solid support, (such as a nitrocellulose filter, a nylon filter, or derivitzed nylon filter), and incubating the sample with the antibodies that specifically bind GPCR. The anti-GPCR antibodies specifically bind to the GPCR on the solid support. These antibodies may be directly labeled or alternatively may be subsequently detected using labeled antibodies (e.g., labeled sheep anti-mouse antibodies) that specifically bind to the anti-GPCR antibodies.

Labels

The particular label or detectable group used in an assay is not a critical aspect of the invention, as long as it does not significantly interfere with the specific binding of the antibody used in the assay. The detectable group can be any material having a detectable physical or chemical property. Such detectable labels have been well-developed in the field and, in general, almost any label useful in assay methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $35S$, $^{14}C$, or $^{32}P$), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. The choice of label used in an assay depends on factors such as the required sensitivity, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize GPCRs, or secondary antibodies that recognize anti-GPCR.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazined-iones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

In addition, techniques developed for the production of "chimeric antibodies", the splicing of antibody genes from different species to obtain a molecule with appropriate antigen specificity and biological activity can be used. Monoclonal and other antibodies can be "humanized" to prevent a patient from mounting an immune response against the antibody when it is used therapeutically. Such antibodies may be sufficiently similar in sequence to human antibodies to be used directly in therapy or may require alteration of a few key residues. For example, sequence differences between rodent antibodies and human sequences can be minimized by replacing residues which differ from those in the human sequences by site directed mutagenesis of individual residues or by grating of entire complementarity determining regions. Antibodies which specifically bind to GPCR can thus contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to GPCR. Antibodies with related specificity, but of distinct idiotypic composition, can be generated by chain shuffling from random combinatorial immunoglobin libraries. Single-chain antibodies also can be constructed using a DNA amplification method, such as PCR, using hybridoma cDNA as a template. Single-chain antibodies can be mono- or bispecific, and can be bivalent or tetravalent. Construction of tetravalent, bispecific single-chain antibodies is taught. A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology.

Antibodies according to the invention can be purified by methods well known in the art. For example, antibodies can be affinity purified by passage over a column to which GPCR is bound. The bound antibodies can then be eluted from the column using a buffer with a high salt concentration Immunoassays In addition to the detection of GPCR genes and gene expression using nucleic acid hybridization technology, one can also use immunoassays to detect GPCRs, e.g., to identify cells such as cancer cells, in particular breast cancer cells, and variants of GPCRs. Immunoassays can be used to qualitatively or quantitatively analyze GPCRs. A general overview of the applicable technology can be found in Harlow & Lane, Antibodies: A Laboratory Manual (1988).

Immunoassays use a labeling agent to specifically bind to and label the complex formed by the antibody and antigen. The labeling agent may itself be one of the moieties comprising the antibody/antigen complex. Alternatively, the labeling agent may be a third moiety, such a secondary antibody that specifically binds to the antibody/GPCR complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., J. Immunol. 111: 1401-1406 (1973); Akerstrom et al., J. Immunol. 135:2589-2542 (1985)). The labeling agent can be modified with a detectable moiety, such as biotin, to which another molecule can specifically bind, such as streptavidin. A variety of detectable moieties are well known to those skilled in the art.

Noncompetitive immunoassays are assays in which the amount of antigen is directly measured. In one preferred "sandwich" assay, for example, the anti-GPCR antibodies can be bound directly to a solid substrate on which they are immobilized. These immobilized antibodies then capture GPCRs present in the test sample. The GPCR thus immobilized is then bound by a labeling agent, such as a second GPCR antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

In competitive assays, the amount of GPCR present in the sample is measured indirectly by measuring the amount of a known, added (exogenous) GPCR displaced (competed away) from an anti-GPCR antibody by the unknown GPCR present in a sample. In one competitive assay, a known amount of GPCR is added to a sample and the sample is then contacted with an antibody that specifically binds to the GPCR. The amount of exogenous GPCR bound to the antibody is inversely proportional to the concentration of GPCR present in the sample. In a particularly preferred embodiment, the antibody is immobilized on a solid substrate. The amount of GPCR bound to the antibody may be determined either by measuring the amount of GPCR present in a GPCR/antibody complex, or alternatively by measuring the amount of remaining uncomplexed protein. The amount of GPCR may be detected by providing a labeled GPCR molecule.

A hapten inhibition assay is another preferred competitive assay. In this assay the known GPCR is immobilized on a solid substrate. A known amount of anti-GPCR antibody is added to the sample, and the sample is then contacted with the immobilized GPCR. The amount of anti-GPCR antibody bound to the known immobilized GPCR is inversely proportional to the amount of GPCR present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can also be used for crossreactivity determinations. For example, a protein at least partially encoded by SEQ ID NOS: 1, 3, 5, 7, 9, 11, 13, 15, or 17 can be immobilized to a solid support. Proteins (e.g., GPCR proteins and homologs) are added to the assay that compete for binding of the antisera to the immobilized antigen. The ability of the added proteins to compete for binding of the antisera to the immobilized protein is compared to the ability of GPCRs encoded by SEQ ID NO: 1, 3, 5, 7, 9, 11, 13, 15, or 17 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of an GPCR, to the immunogen protein (i.e., the GPCR of SEQ ID NOS: 1, 3, 5, 7, 9, 11, 13, 15, or 17). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NOS: 1, 3, 5, 7, 9, 11, 13, 15, or 17 that is required to inhibit 50% of binding, then the second protein is said to specifically bind to the polyclonal antibodies generated to a GPCR immunogen.

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Other assay formats include liposome immunoassays (LIA), which use liposomes designed to bind specific molecules (e.g., antibodies) and release encapsulated reagents or markers upon a binding event. The released chemicals are then detected according to standard techniques (see Monroe et al., Amer. Clin. Prod. Rev. 5:34-41 (1986)).

Deorphanization

Among known GPCR proteins some 200 exist for which their natural ligand is unknown. These "orphan" GPCRs have the potential to serve as targets for novel drugs and novel indications. Yet, to be used in pharmaceutical research, these GPCRs need first to be "deorphanized", i.e. their natural ligands need to be discovered to allow for development of applications such as high-throughput screening assays.

Deorphanization refers to the identification of activating ligands is a key task in reverse molecular pharmacology. Identifying receptor-agonist pairs usually allows the rapid elucidation of the physiological role of both partners, sometimes putting them in unexpected contexts. Although bioinformatics methods are initially helpful to successfully direct ligand-pairing experiments, deorphanization strategies generally rely on biological screening of orphan GPCRs expressed in recombinant expression systems such as immortalized mammalian cells, yeast, and *Xenopus* melanophores.

Agonist ligand libraries used for deorphanization can include small molecules, peptides, proteins, lipids or tissue extracts. Identification of an activating agonistic ligand of the cell-surface-expressed receptors is often dependent on the activation of an intracellular signaling cascade.

A difficulty in assay design for orphan GPCRs is that the signaling cascade is not known for a new orphan receptor. Therefore, generic assay systems amenable for high throughput screening are generally used to screen large surrogate ligand collections. One successful approach for deorphanization uses fluorescent imaging plate reader (FLIPR) screening technology, which detects ligand-induced intracellular $Ca^{+2}$ mobilization.

Given the broad chemical diversity of the molecules that are recognized by GPCRs, deorphanization libraries try to cover as many known active chemical classes as possible. The term "surrogate agonist library" is also appropriate given that the purpose of these libraries is to find a chemical compound that selectively activates a given orphan receptor of interest. Typically, compounds identical or similar to previously identified GPCR agonists are included together with approved drugs and other reference compounds with known bioactivity, such as primary metabolites like the KEGG compound set, or commercially available compilations like the Tocris LOPAC, the Prestwick, or the Sial Biomol sets.

Typically, the size of deorphanization or surrogate libraries is on the order of a few thousand well-characterized compounds amenable for medium-throughput screening. The design of lead-finding libraries follows the same molecular mimicry principles and makes best use of the substantial medicinal chemistry knowledge generated during the last decades around GPCR compounds together with more modern concepts, including lead/drug likeness and computational combinatorial library design. Focused library design concepts target the classical binding sites in general, while design concepts of bivalent ligands and allosteric ligands can be used as the understanding of the GPCR oligomerization phenomenon increases.

Diseases Associated with GPCRs

Mutations in GPCRs have been associated with a wide variety of illnesses, particularly cancers and diseases involving inflammation.

Some disease-causing mutations result in constitutive receptor activation, such as in Jansen's disease, where the hypercalcemia and skeletal dysplasia found in many cases is the result of a constitutively overactive parathyroid hormone/parathyroid hormone related protein receptor. In such diseases, inhibitors of activation are of particular interest as potential therapeutics.

Virally encoded GPCRs may also have a direct role in human diseases. For example, Kaposi's sarcoma-associated herpes virus has been implicated in Kaposi's sarcomagenesis, and the human cytomegalovirus-encoded GPCRs have been implicated in atherosclerosis.

Certain GPCRs are associated with the disorders of the peripheral and central nervous system (CNS), cardiovascular diseases, hematological diseases, cancer, inflammation, urological diseases, respiratory diseases and gastroenterological diseases. Such disorders may include a wide range of diseases, as discussed further below.

Nervous System Disorders

CNS disorders include disorders of the central nervous system as well as disorders of the peripheral nervous system.

CNS disorders include, but are not limited to brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, and Korsakoff's psychosis, within the meaning of the definition are also considered to be CNS disorders. Jakob Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be CNS disorders. Jakob Pain, within the meaning of this definition, is also considered to be a CNS disorder. Pain can be associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neulalgias, and post-herpetic neuralgia. Pain associated with peripheral nerve damage, central pain (i.e. due to cerebral ischemia) and various chronic pain i.e., lumbago, back pain (low back pain), inflammatory and/or rheumatic pain. Headache pain (for example, migraine with aura, migraine without aura, and other migraine disorders), episodic and chronic tension-type headache, tension-type like headache, cluster headache, and chronic paroxysmal hemicrania are also CNS disorders. Jakob Visceral pain such as pancreatits, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome and protatodynia are also CNS disorders. Jakob Also considered to be a disorder of the nervous system are acute pain, for example postoperative pain, and pain after trauma. Jakob The human GPCR is highly expressed in the following brain tissues: brain, Alzheimer brain, cerebellum (right), cerebellum (left), cerebral cortex, Alzheimer brain frontal lobe, occipital lobe, pons, substantia nigra, cerebral meninges, corpus callosum, dorsal root ganglia, neuroblastoma IMR32 cells. The expression in brain tissues and in particular the differential expression between diseased tissue Alzheimer brain and healthy tissue brain, between diseased tissue Alzheimer brain frontal lobe and healthy tissue frontal lobe demonstrates that the human GPCR or mRNA can be utilized to diagnose nervous system diseases. Additionally the activity of the human GPCR can be modulated to treat nervous system diseases.

Cardiovascular Disorders

GPCRs are highly expressed in the following cardiovascular related tissues: heart, pericardium, heart atrium (right), heart atrium (left), artery, coronary artery, coronary artery sclerotic. Expression in the above mentioned tissues and in particular the differential expression between diseased tissue coronary artery sclerotic and healthy tissue coronary artery indicates that GPCR protein, DNA or mRNA can be utilized to diagnose cardiovascular diseases.

Heart failure is defined as a pathophysiological state in which an abnormality of cardiac function is responsible for the failure of the heart to pump blood at a rate commensurate with the requirement of the metabolizing tissue. It includes all forms of pumping failures such as high-output and low-output, acute and chronic, right-sided or left-sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included as well as the acute treatment of MI and the prevention of complications. Ischemic diseases are conditions in which the coronary flow is restricted resulting in a perfusion which is inadequate to meet the myocardial requirement for oxygen. This group of diseases includes stable angina, unstable angina and asymptomatic ischemia.

Arrhythmias include all forms of atrial and ventricular tachyarrhythmas, atrial tachycardia, atrial flutter, atrial fibrillation, atrio-ventricular reentrant tachycardia, preexitation syndrome, ventricular tachycardia, ventricular flutter, ventricular fibrillation, as well as bradycardic forms of arrhythmias.

Hypertensive vascular diseases include primary as well as all kinds of secondary arterial hypertension, renal, endocrine, neurogenic, others. The genes may be used as drug targets for the treatment of hypertension as well as for the prevention of all complications arising from cardiovascular diseases.

Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon and venous disorders.

Cardiovascular diseases include but are not limited to disorders of the heart and the vascular system like congestive heart failure, myocardial infarction, ischemic diseases of the heart, all kinds of atrial and ventricular arrhythmias, hypertensive vascular diseases, peripheral vascular diseases, and atherosclerosis.

Examples of disorders of lipid metabolism are hyperlipidemia (abnormally high levels of fats (cholesterol, triglycerides, or both) in the blood, may be caused by family history of hyperlipidemia), obesity, a high-fat diet, lack of exercise, moderate to high alcohol consumption, cigarette smoking, poorly controlled diabetes, and an underactive thyroid gland), hereditary hyperlipidemias (type I hyperlipoproteinemia (familial hyperchylomicronemia), type II hyperlipoproteinemia (familial hypercholesterolemia), type In hyperlipoproteinemia, type IV hyperlipoproteinemia, or type V hyperlipoproteinemia), hypolipoproteinemia, lipidoses (caused by abnormalities in the enzymes that metabolize fats), Gaucher's disease, Niemann-Pick disease, Fabry's disease, Wolman's disease, cerebrotendinous xanthomatosis, sitosterolemia, Refsum's disease, or Tay-Sachs disease.

Kidney Disorders

Kidney disorders may lead to hypertension or hypotension. Examples of kidney problems possibly leading to hypertension are renal artery stenosis, pyelonephritis, glomerulonephritis, kidney tumors, polycistic kidney disease, injury to the kidney, or radiation therapy affecting the kidney. Excessive urination may lead to hypotension.

Hematological Disorders

Hematological disorders comprise diseases of the blood and all its constituents as well as diseases of organs and tissues involved in the generation or degradation of all the constituents of the blood. They include but are not limited to 1) Anemias, 2) Myeloproliferative Disorders, 3) Hemorrhagic Disorders, 4) Leukopenia, 5) Eosinophilic Disorders, 6) Leukemias, 7) Lymphomas, 8) Plasma Cell Dyscrasias, 9) Disorders of the Spleen in the course of hematological disorders. Disorders according to 1) include, but are not limited to anemias due to defective or deficient hem synthesis, deficient erytlhropoiesis. Disorders according to 2) include, but are not limited to polycythemia vera, tumor-associated erythrocytosis, myelofibrosis, thrombocythemia. Disorders according to 3) include, but are not limited to vasculitis, thrombocytopenia, heparin-induced thrombocytopenia, thrombotic thrombocytopenic purpura, hemolytic-uremic syndrome, hereditary and acquired disorders of platelet function, hereditary coagulation disorders. Disorders according to 4) include, but are not limited to neutropenia, lymphocytopenia. Disorders according to 5) include, but are not limited to hypereosinophilia, idiopathic hypereosinophilic syndrome. Disorders according to 6) include, but are not limited to acute myeloic leukemia, acute lymphoblastic leukemia, chronic myelocytic leukemia, chronic lymphocytic leukemia, myelodysplastic syndrome. Disorders according to 7) include, but are not limited to Hodgkin's disease, non-Hodgkin's lymphoma, Burkitt's lymphoma, mycosis fungoides cutaneous T-cell lymphoma. Disorders according to 8) include, but are not limited to multiple myeloma, macroglobulinemia, heavy chain diseases. In extension of the preceding idiopathic thrombocytopenic purpura, iron deficiency anemia, megaloblastic anemia (vitamin B12 deficiency), aplastic anemia, thalassemia, malignant lymphoma bone marrow invasion, malignant lymphoma skin invasion, hemolytic uremic syndrome, giant platelet disease are considered to be hematological diseases too.

The human GPCR is highly expressed in the following tissues of the hematological system: leukocytes peripheral blood), bone marrow, erythrocytes, lymphnode, thymus, thrombocytes, bone marrow CD34+ cells, bone marrow CD15+ cells, spleen, spleen liver cirrhosis.

Gastrointestinal and Liver Diseases

Gastrointestinal diseases comprise primary or secondary, acute or chronic diseases of the organs of the gastrointestinal tract which may be acquired or inherited, benign or malignant or metaplastic, and which may affect the organs of the gastrointestinal tract or the body as a whole. They comprise but are not limited to 1) disorders of the esophagus like achalasia, vigoruos achalasia, dysphagia, cricopharyngeal incoordination, pre-esophageal dysphagia, diffuse esophageal spasm, globus sensation, Barrett's metaplasia, gastroesophageal reflux, 2) disorders of the stomach and duodenum like functional dyspepsia, inflammation of the gastric mucosa, gastritis, stress gastritis, chronic erosive gastritis, atrophy of gastric glands, metaplasia of gastric tissues, gastric ulcers, duodenal ulcers, neoplasms of the stomach, 3) disorders of the pancreas like acute or chronic pancreatitis, insufficiency of the exocrinic or endocrinic tissues of the pancreas like steatorrhea, diabetes, neoplasms of the exocrine or endocrine pancreas like 3.1) multiple endocrine neoplasia syndrome, ductal adenocarcinoma, cystadenocarcinoma, islet cell tumors, insulinoma, gastrinoma, carcinoid tumors, glucagonoma, Zollinger-Ellison syndrome, Vipoma syndrome, malabsorption syndrome, 4) disorders of the bowel like chronic inflammatory diseases of the bowel, Crohn's disease, ileus, diarrhea and constipation, colonic inertia, megacblon, malabsorption syndrome, ulcerative colitis, 4.1) functional bowel disorders like irritable bowel syndrome, 4.2) neoplasms of the bowel like familial polyposis, adenocarcinoma, primary malignant lymphoma, carcinoid tumors, Kaposi's sarcoma, polyps, cancer of the colon and rectum.

Liver diseases comprise primary or secondary, acute or chronic diseases or injury of the liver which may be acquired or inherited, benign or malignant, and which may affect the liver or the body as a whole. They comprise but are not limited to disorders of the bilirubin metabolism, jaundice, syndroms of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, liver diseases due to alcohol, alcoholic hepatitis or cirrhosis, fibrosis and cirrhosis, fibrosis and cirrhosis of the liver due to inborn errors of metabolism or exogenous substances, storage diseases, syndromes of Gaucher's, Zellweger's, Wilson's-disease, acute or chronic hepatitis, viral hepatitis and its variants, inflammatory conditions of the liver due to viruses, bacteria, fungi, protozoa, helminths; drug induced disorders of the liver, chronic liver diseases like primary sclerosing cholangitis, alpha.sub.1-antitrypsin-deficiency, primary biliary cirrhosis, postoperative liver disorders like postoperative intrahepatic cholestasis, hepatic granulomas, vascular liver disorders associated with systemic disease, benign or malignant neoplasms of the liver, disturbance of liver metabolism in the new-born or prematurely born.

GPCRs are highly expressed in the following tissues of the gastro-enterological system: esophagus, esophagus tumor, stomach tumor, rectum. The expression in the above mentioned tissues and in particular the differential expression between diseased tissue esophagus tumor and healthy tissue esophagus, between diseased tissue stomach tumor and healthy tissue stomach demonstrates that GPCR DNA, mRNA and polypeptides can be utilized to diagnose of gastroenterological disorders. Additionally the activity of the human GPCR can be modulated to treat gastroenterological disorders.

Cancer Disorders

Cancer disorders within the scope of this definition comprise any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. Cells and tissues are cancerous when they grow more rapidly than normal cells, displacing or spreading into the surrounding healthy tissue or any other tissues of the body described as metastatic growth, assume abnormal shapes and sizes, show changes in their nucleocytoplasmatic ratio, nuclear polychromasia, and finally may cease.

Cancerous cells and tissues may affect the body as a whole when causing paraneoplastic syndromes or if cancer occurs within a vital organ or tissue, normal function will be impaired or halted, with possible fatal results. The ultimate involvement of a vital organ by cancer, either primary or metastatic, may lead to the death of the mammal affected. Cancer tends to spread, and the extent of its spread is usually related to an individual's chances of surviving the disease.

Cancers are generally said to be in one of three stages of growth: early, or localized, when a tumor is still confined to the tissue of origin, or primary site; direct extension, where cancer cells from the tumor have invaded adjacent tissue or have spread only to regional lymph nodes; or metastasis, in which cancer cells have migrated to distant parts of the body from the primary site, via the blood or lymph systems, and have established secondary sites of infection.

Cancer is said to be malignant because of its tendency to cause death if not treated. Benign tumors usually do not cause death, although they may if they interfere with a normal body function by virtue of their location, size, or paraneoplastic side effects. Hence benign tumors fall under the definition of cancer within the scope of this definition as well. In general, cancer cells divide at a higher rate than do normal cells, but the distinction between the growth of cancerous and normal tissues is not so much the rapidity of cell division in the former as it is the partial or complete loss of growth restraint in cancer cells and their failure to differentiate into a useful, limited tissue of the type that characterizes the functional equilibrium of growth of normal tissue.

The term "cancer" as referred to herein is not limited to simple benign neoplasia but comprises any other benign and malign neoplasia like 1) Carcinoma, 2) Sarcoma, 3) Carcinosarcoma, 4) Cancers of the blood-forming tissues, 5) tumors of nerve tissues including the brain, 6) cancer of skin cells.

GPCRs are expressed in the following cancer tissues: esophagus tumor, stomach tumor, lung tumor, ovary tumor, kidney tumor. The expression in the above mentioned tissues and in particular the differential expression between diseased tissue esophagus tumor and healthy tissue esophagus, between diseased tissue stomach tumor and healthy tissue stomach, between diseased tissue lung tumor and healthy tissue lung, between diseased tissue ovary tumor and healthy tissue ovary, between diseased tissue kidney tumor and healthy tissue kidney demonstrates that the human GPCR DNA, mRNA and polypeptides can be utilized to diagnose of cancer. Additionally the activity of GPCR can be modulated to treat cancer.

Inflammatory Diseases

Inflammatory diseases comprise diseases triggered by cellular or non-cellular mediators of the immune system or tissues causing the inflammation of body tissues and subsequently producing an acute or chronic inflammatory condition. Examples for such inflammatory diseases are hypersensitivity reactions of type I-IV, for example but not limited to hypersensitivity diseases of the lung including asthma, atopic diseases, allergic rhinitis or conjunctivitis, angioedema of the lids, hereditary angioedema, antireceptor hypersensitivity reactions and autoimmune diseases, Hashimoto's thyroiditis, systemic lupus erythematosus, Goodpasture's syndrome, pemphigus, myasthenia gravis, Grave's and Raynaud's disease, type B insulin-resistant diabetes, rheumatoid arthritis, psoriasis, Crohn's disease, scleroderma, mixed connective tissue disease, polymyositis, sarcoidosis, glomerulonephritis, acute or chronic host versus graft reactions.

GPCR is expressed in the following tissues of the immune system and tissues responsive to components of the immune system as well as in the following tissues responsive to mediators of inflammation: leukocytes (peripheral blood), bone marrow, bone marrow CD15+ cells, spleen liver cirrhosis, lung COPD. The expression in the above mentioned tissues and in particular the differential expression between diseased tissue spleen liver cirrhosis and healthy tissue spleen, between diseased tissue lung COPD and healthy tissue lung demonstrates that GPCR DNA, mRNA and polypeptides can be utilized to diagnose of inflammatory diseases. Additionally the activity of GPCR can be modulated to treat inflammatory diseases.

Disorders Related to Pulmology

Asthma is thought to arise as a result of interactions between multiple genetic and environmental factors and is characterized by three major features: 1) intermittent and reversible airway obstruction caused by bronchoconstriction, increased mucus production, and thickening of the walls of the airways that leads to a narrowing of the airways, 2) airway hyperresponsiveness, and 3) airway inflammation. Certain cells are critical to the inflammatory reaction of asthma and they include T cells and antigen presenting cells, B cells that produce IgE, and mast cells, basophils, eosinophils, and other cells that bind IgE. These effector cells accumulate at the site of allergic reaction in the airways and release toxic products that contribute to the acute pathology and eventually to tissue destruction related to the disorder. Other resident cells, such as smooth muscle cells, lung epithelial cells, mucus-producing cells, and nerve cells may also be abnormal in individuals with asthma and may contribute to its pathology. While the airway obstruction of asthma, presenting clinically as an intermittent wheeze and shortness of breath, is generally the most pressing symptom of the disease requiring immediate treatment, the inflammation and tissue destruction associated with the disease can lead to irreversible changes that eventually make asthma a chronic and disabling disorder requiring long-term management.

Chronic obstructive pulnonary (or airways) disease (COPD) is a condition defined physiologically as airflow obstruction that generally results from a mixture of emphysema and peripheral airway obstruction due to chronic bronchitis [Botstein, 1980]. Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does also occur in non-smokers.

GPCR is highly expressed in the following tissues of the respiratory system: leukocytes (peripheral blood), bone marrow CD15+ cells, lung, lung right upper lobe, lung right mid lobe, lung right lower lobe, lung tumor, lung COPD, trachea. The expression in the above mentioned tissues and in particular the differential expression between diseased tissue lung tumor and healthy tissue lung, between diseased tissue lung COPD and healthy tissue lung demonstrates that GPCR DNA, mRNA and polypeptides can be utilized to diagnose of respiratory diseases. Additionally the activity of GPCR can be modulated to treat those diseases.

Disorders Related to Urology

Genitourinary disorders comprise benign and malign disorders of the organs constituting the genitourinary system of female and male, renal diseases like acute or chronic renal failure, immunologically mediated renal diseases like renal transplant rejection, lupus nephritis, immune complex renal diseases, glomerulopathies, nephritis, toxic nephropathy, obstructive uropathies like benign prostatic hyperplasia (BPH), neurogenic bladder syndrome, urinary incontinence like urge-, stress-, or overflow incontinence, pelvic pain, and erectile dysfunction.

GPCR is expressed in the following urological tissues: ureter, penis, corpus cavernosum, fetal kidney, kidney, kidney tumor. The expression in the above mentioned tissues and in particular the differential expression between diseased tissue kidney tumor and healthy tissue kidney demonstrates that GPCR DNA, mRNA and polypeptides can be utilized to diagnose of urological disorders. Additionally the activity of the human GPCR can be modulated to treat urological disorders.

The present invention provides for both prophylacetic and therapeutic methods for disorders of the peripheral and central nervous system, cardiovascular diseases, hematological diseases, cancer, inflammation, urological diseases, respiratory diseases and gastroenterological diseases.

The present invention provides methods of treating an individual afflicted with a disease or disorder characterized by unwanted expression or activity of GPCR or a protein in the GPCR signaling pathway. In one embodiment, the method involves administering an agent like any agent identified or identifiable in assays as described herein, or a combination of such agents to modulate expression or activity of GPCR or proteins in the GPCR signaling pathway. In another embodiment, the method involves administering a regulator of GPCR as therapy to compensate for reduced or undesirably low expression or activity of GPCR or a protein in the GPCR signaling pathway.

The expression in the above mentioned tissues and in particular the differential expression between diseased tissue spleen liver cirrhosis and healthy tissue spleen demonstrates that GPCR DNA, mRNA and polypeptides can be utilized to diagnose of hematological diseases. Additionally the activity of GPCR can be modulated to treat hematological disorders.

EXAMPLES

The following examples are provided to illustrate the invention and are not intended to limit its scope. Other variants of the invention will be readily apparent to one of ordinary skill in the art and are encompassed by the appended claims.

Example I

Expression Vector Design

A vector (pMEX2) was designed to facilitate expression and detection of a GPCR expressed with correct orientation on the cytoplasmic membrane of mammalian cells. The vector contained a pUC origin and the beta-lactamase gene for replication and ampicillin selection of the plasmid in bacteria, as shown in FIG. 10. A puromycin resistance marker for maintaining the plasmid in mammalian cells is also included in the vector. Expression of the gene of interest was under control of a strong CMV promoter for high-level transcription activity. The expression cassette also contained a Kozak consensus sequence for optimal translation initiation and a SV40 late poly adenylation signal for stability of the transcripts.

Some features were added to the vector to facilitate isolation of GPCR cell lines. First, transportation of the receptor protein to the cytoplasmic membrane was greatly improved by fusion of an amino-terminal cleavable secretory signal peptide (amino acid seq: METDTLLLWVLLLWVPG-STGD, corresponding to SEQ ID NO: 19, position 1102-1164) derived from a murine Ig kappa light chain. Second, a short affinity tag (Flag tag; amino acid seq: DYKDDDDK corresponding to SEQ ID NO: 19, position 1168-1191) was fused downstream from the signal peptide and followed by a short flexible linker (glycine-serine-glycine) upstream from the mature sequence of the target gene.

Addition of the Flag tag at the amino-terminus of the receptor served two functions. First, it facilitated detection of the recombinant receptor and isolation of cells expressing the receptor. Secondly, it served as a marker for correct orientation of the receptor on the cytoplasmic membrane. Therefore, only receptors of correct orientation with the Flag tag exposed to the extracellular side of the cytoplasmic membrane can be detected by the mAb. The use of a universal affinity tag in this application is not limited to the Flag tag and can be extended to any sequence (e.g. Flag, myc, H is tag, C9, HA etc.) which is recognized by a fluorescence-labeled binder, as long as it does not interfere with ligand binding to the fused receptor.

Upon translocation of the full-length protein to the membrane, the signal peptide was processed, leaving the receptor with an amino-terminal Flag tag exposed to the extracellular environment. Open reading frame of the GPCR to be expressed was amplified by polymerase chain reaction (PCR) from either a cDNA library or an EST clone and subcloned into the cloning sites (5'-BamH I and Sal I-3') on the vector. The integrity of the gene sequence was confirmed by sequencing reactions through the whole insert using primers outside the cloning sites on the vector. A typical vector map of pMEX2 and its nucleotide sequence are shown in FIG. 10 and FIG. 11 respectively.

Example II

Screening for GPCR Clones

Figure 15:
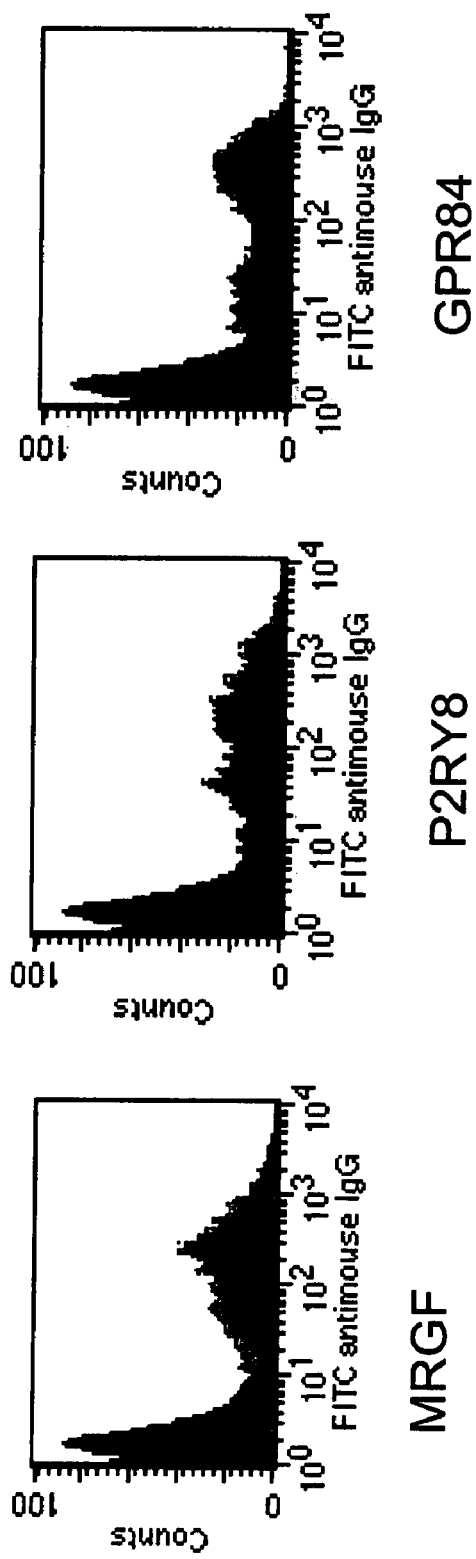
FIG. 15 displays data from FITC analysis of cell surface expression for the identified G-protein coupled receptors (GPCRs).

FACS analysis was carried out to confirm surface expression of the exogenously expressed receptors using the anti-Flag M2 mAb (Sigma) in a transient expression experiment. The plasmid DNA can be delivered into any mammalian cells using any method, including, but not limited to, electroporation, lipid cation and calcium phosphate-mediated transfection, or retrovirus-mediated infection. For the current experiments, the vector was transfected into either human embryonic kidney cells (HEK293) and its derivative (293T) or Chinese hamster ovary cells (CHO-K1) by Lipofectamine 2000 (Invitrogen) according to the manufacturer's protocol. Expression of the recombinant GPCR on cell surface was detected 48 to 60 hours post transfection by fluorescence-activated cell sorting (FACS). A typical expression profile for three GPCRs (MRGF, P2RY8 and GPR84) under transient expression condition is shown in FIG. 15 which shows broad spectrum of expression crossing two to three quadrants in the histograms.

Example III

Ligand-Binding Activity of the Recombinant Receptors

Figure 16:
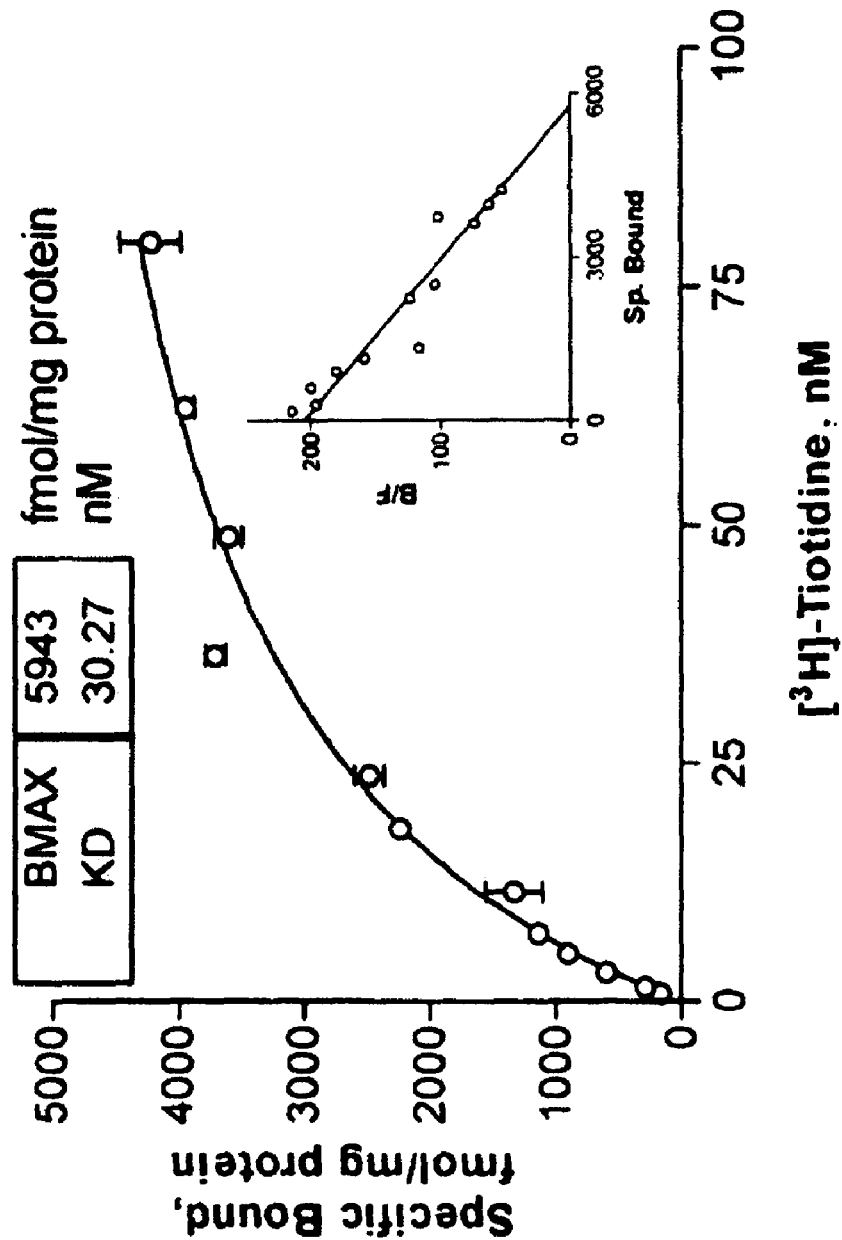
FIG. 16 provides a surface expression profile of 72 recombinant GPCRs as determined by FACS analysis.

A saturation ligand-binding assay was performed to confirm that the recombinant receptors retain its native conformation and ligand-binding activity. The average ligand-binding sites (Bmax; pmol/mg protein) and the affinity (Kd; nM) of the exogenously expressed receptor in a transient expression experiment was measured at 12 radioligand concentrations with duplicate total and non-specific binding determinations. Representative result of specific binding for histamine receptor H2 is shown in FIG. 16. The human receptor exhibited similar affinity for the pig ligand as the endogenous receptor (data not shown). Based on the Bmax value and membrane protein expression per cell, the ligand binding sites was calculated to be 1.05 million copies/cell.

Example IV

Isolation of Stable Cell Lines Expressing High-Level GPCRS

Cell culture. HEK293 cells were maintained in DMEM supplemented with 10% FBS (Invitrogen Inc.), 100 U/ml penicillin/streptomycin. CHOK1 cells were maintained in either DMEM/Ham's F-12 Mix or Ham's F-12 media supplemented with 10% FBS 100 U/ml penicillin/streptomycin (Invitrogen Inc.). Cell transfections were carried out with Lipofectamine 2000 (Invitrogen Inc.) according to the manufacturer's protocol. In order to have large enough amounts of cells, one well of 6-well plate was at 80-90% confluence for HEK293T, Gα16/HEK293T, Gqi5/HEK293T, CHO-K1, Gα16/CHO-K1 and Gqi5/CHO-K1 cells or one T25 at 90% confluence for RH7777, 1321N1 cells.

Flow cytometry analysis. To determine cell-surface GPCR expression, cells were detached from the plates with Cellstripper (Mediatech, Inc.). Cells were washed once with PBS, once with PBS/1% BSA at 4° C. They were incubated with mouse anti-Flag M2 mAb (Sigma Chemical Co) for 30 minutes at 4° C., washed twice with PBS/1% BSA at 4° C., and further incubated on ice in the dark with FITC-labeled goat anti-mouse IgG Sigma Chemical Co) as secondary antibody. Cells were washed twice again and resuspended in 400 µl PBS/1% BSA. The fluorescence of 10,000 cells/tube was assayed by a FACSort flow cytofluorometer (Becton Dickinson). For direct immunofluorescent staining, cells were first incubated with PE-labeled mouse anti-FLAG antibody (Prozyme Inc. San Leandro, Calif.) at 30 ug/ml for 30 minutes on ice, then washed and analyzed as described above.

Stable Pool Selection and Isolation of Stable Cell Lines Expressing High-Level GPCRs To isolate stable populations, the cells were transfected in 6-well plates, transferred to 100-mm Petri dish two days post transfection. The stable pools for were selected by incubation of the cells in culture medium containing 1 ug/ml puromycin (InvivoGen Inc., San Diego, Calif.) for another 10 to 14 days for HEK293 transfectants, or medium containing 10 ug/ml puromycin for 7 to 10 days for CHOK1 transfectants.

Figure 18:
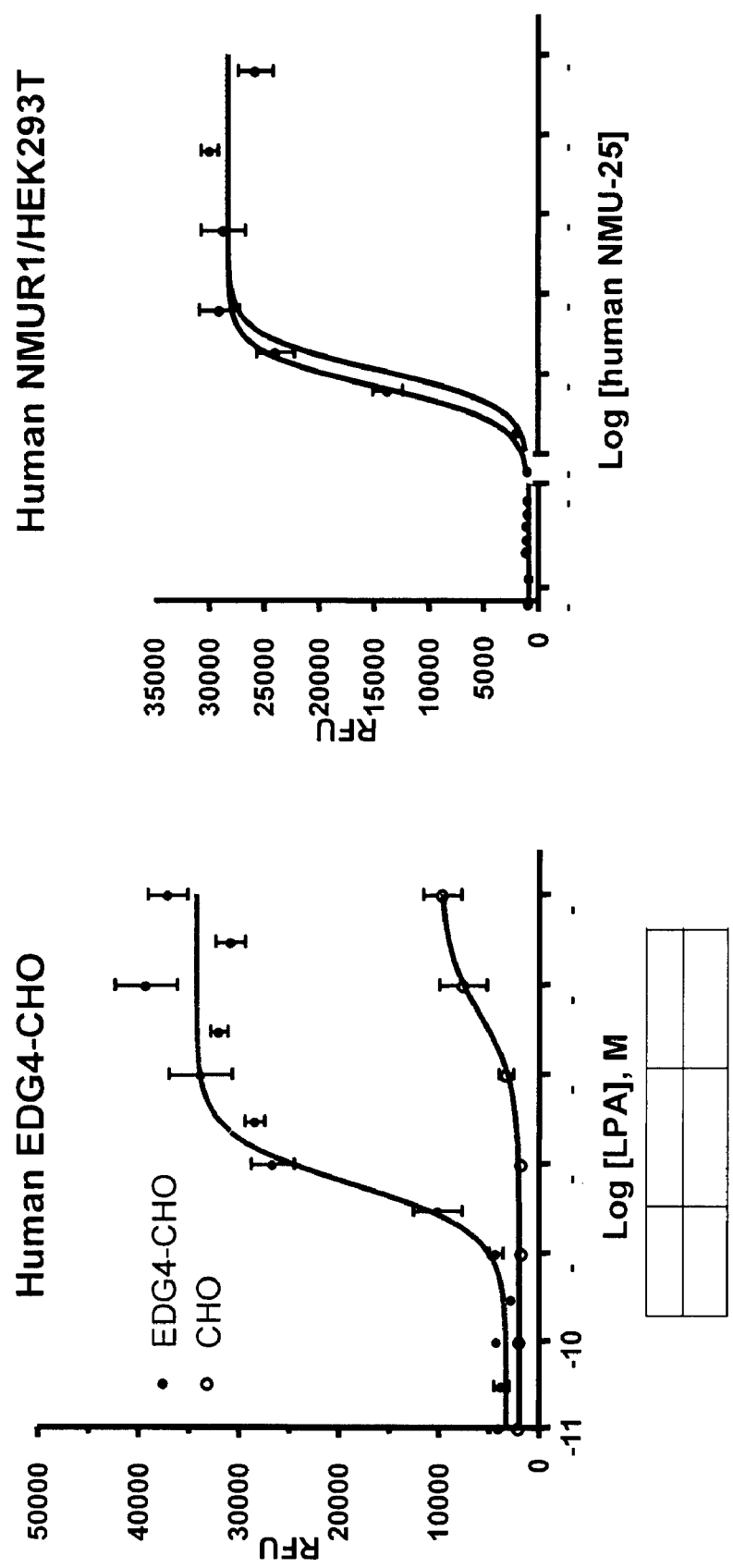
FIG. 18 provides data from a cell surface assay for the identified GPCRs transfected into HEK293T cells.
Figure 19:
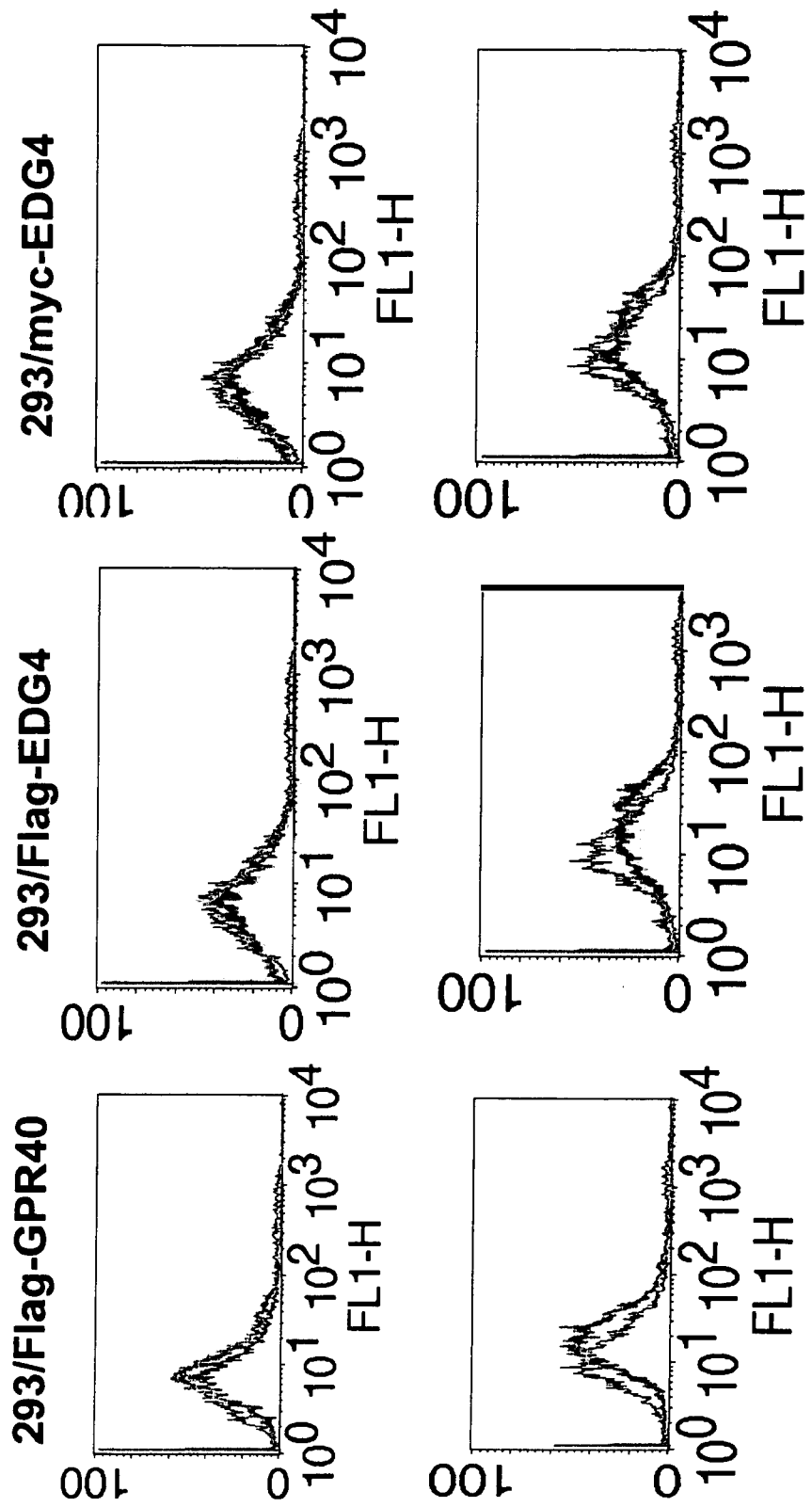
FIG. 19 displays data from a calcium signaling assay for the GPCRs EDG4 (CHO cells) and NMUR1 (HEK293T cells). CHO/Flag-EDG4 is a stable cell line used as an immunogen. The traces in the top row are from negative antiserum tested by Flag peptide ELISA. The traces in the bottom row are from positive antiserum tested by Flag peptide ELISA. The traces labeled 293/Flag-GPR40 are data from a stable cell line. 293/Flag-EDG4 and 293/myc-EDG4 are data from transiently transfected cells.
Figure 20:
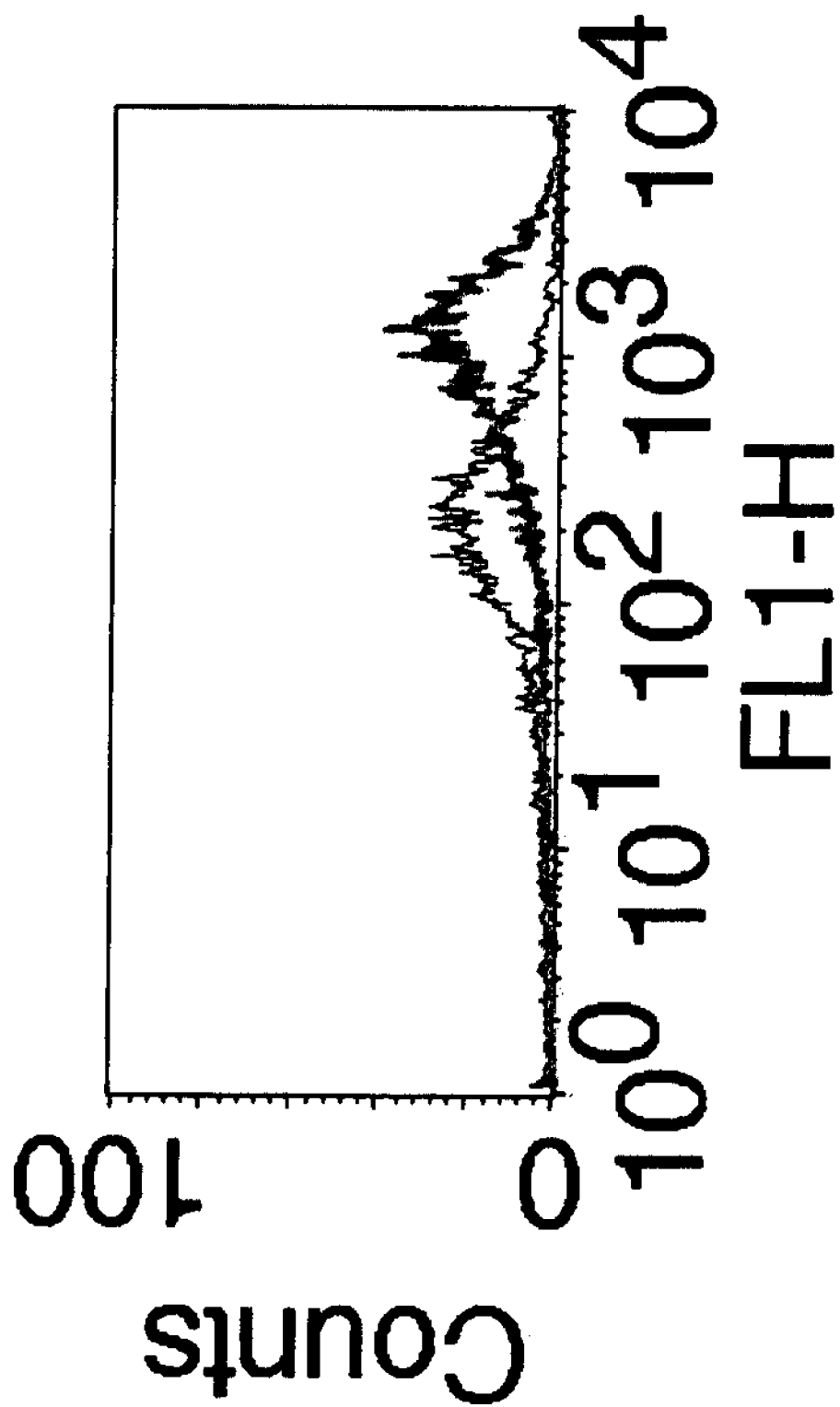
FIG. 20 is data from FACS analysis of mouse immune sera where EDG4 CHO stable cell line was the immunogen. The dark black trace is from a CHO/GPR40 cell line, while the light gray trace is from a CHO/EDG4 cell line.
Figure 21:
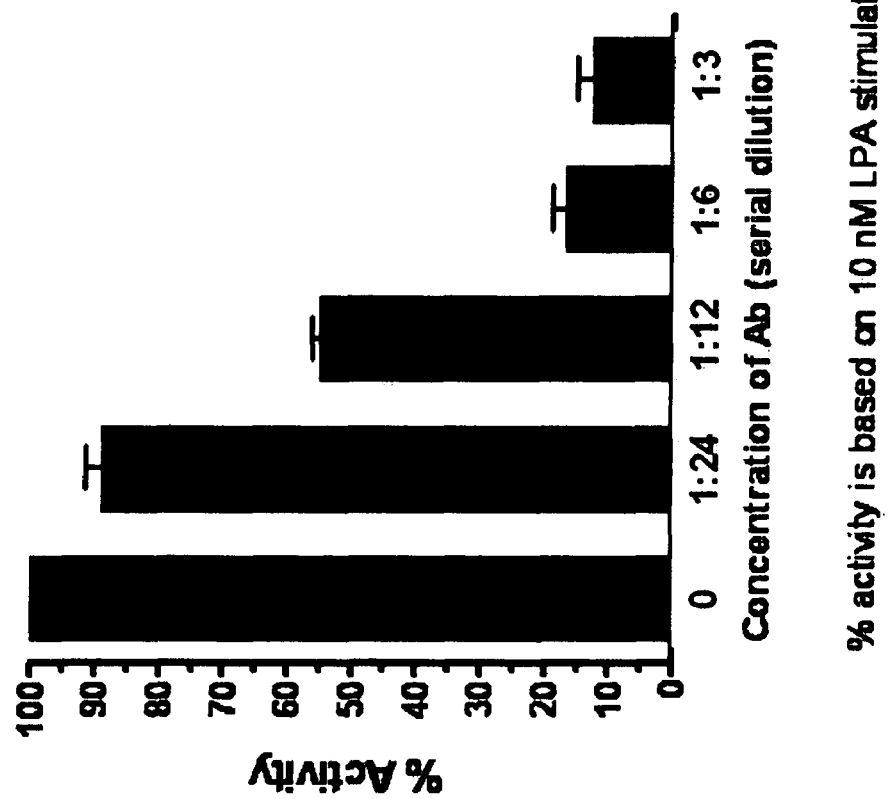
FIG. 21 displays a screening assay of anti-EDG4 monoclonal antibodies from CHO/GPR40 and CHO/EDG4 cell lines.
Figure 22:
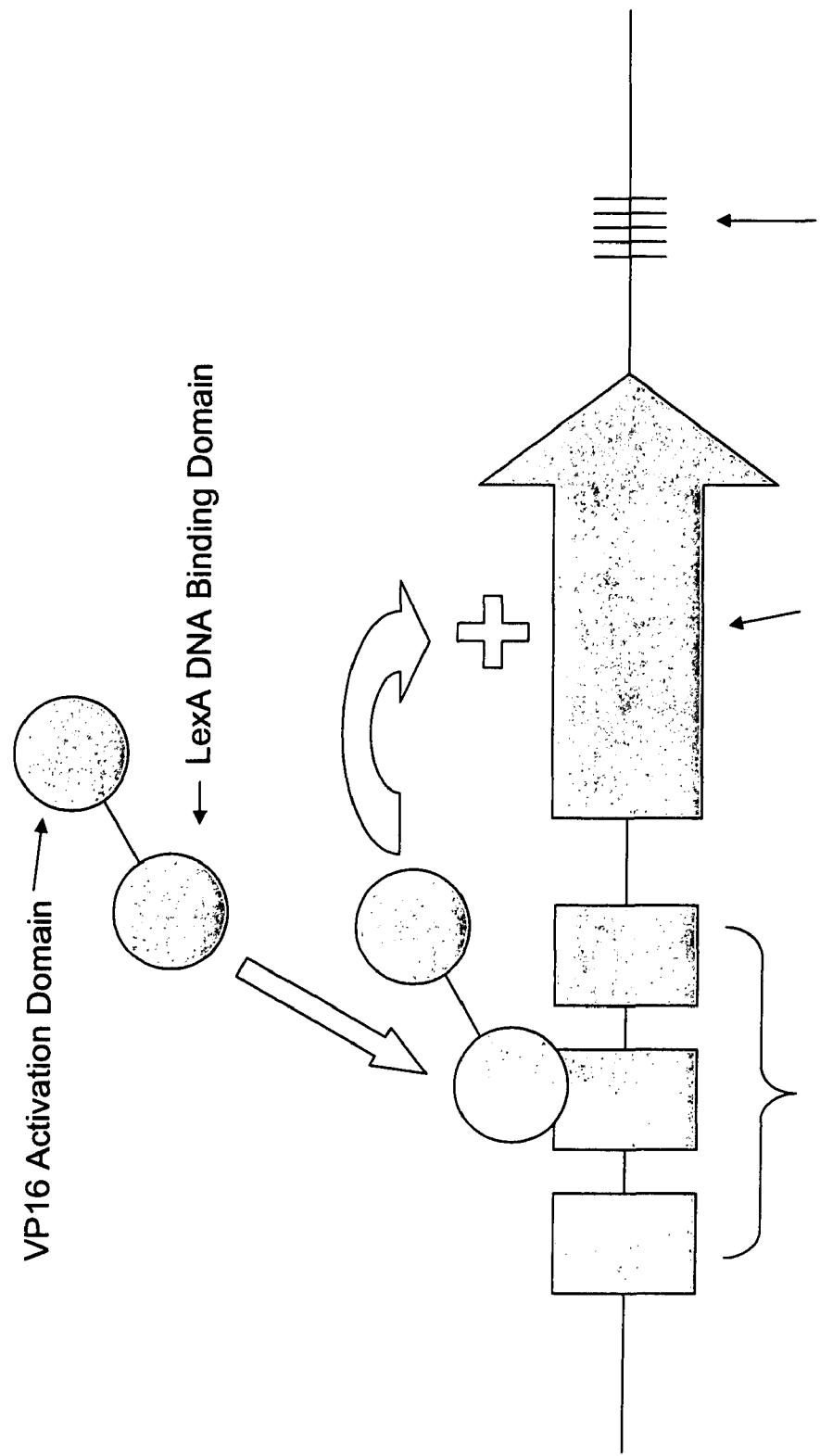
FIG. 22 is a competitive binding assay using EDG4 antibody to block the receptor activation by the G-protein 5G3.

To isolate single cells expressing high levels of the receptors, the stable colonies were pooled together, subjected to cell sorting with FACSort (Becton Dickinson) to separate the high expressers from the rest of the population. The top 0.5% to top 5% high expressers in the total stable population were gated and sorted out subsequently into sterile 50-ml conical tubes pre-soaked with 4% BSA in PBS. The cells were concentrated by centrifugation and either plated on 96-well plates by serial dilution at 0.5, 1, and 5 cells/well, or plated in 150-mm Petri dish in medium containing puromycin. Single-cell colonies were confirmed by examination under a microscope, expanded into 24-well plates, and analyzed by FACS analysis. One such recombinant CHO clone, 9-4, which expresses high level of the human lysophosphatidic acid receptor 4 (EDG4) in CHO-K1 cells is shown by FACS analysis in FIG. 18. The FACS profile for the recombinant HEK293 cell for NMUR1 (colony 3) is shown in FIG. 17. The expression level of EDG4 in CHOK1 (clone 9-4) and NUMR1 in HEK293 (colony 3) are above 200,000 copies per cell, as measured using calibrated standardized phycoerythrin (PE)-conjugated beads (BD QuantiBRITE) and PE-conjugated M2 antibody.

The high-expressing cell lines exhibited good cellular response (such as intracellular calcium release) upon ligand binding to the receptors. The developed GPCR expressing cell lines provide critical tools for cell-based functional drug screening, in vitro ligand-binding assays, crystallization for structural studies and the development of monoclonal antibodies with the use of the recombinant whole cells as immunogens. Data for two representative cell lines are shown in FIG. 17.

Example V

Antibody Development: Whole Cell Immunization Strategy

Immunization of animals GPCR expressing isogenic cell line at an expression level of >100,000 copies per cell was used as immunogen. Female Balb/c mice of 6-8 weeks old are primary choice of animal. Each mouse is immunized with 5-10 millions of live cells per mouse. Mouse: 6-8 weeks Balb/c mouse as primary strain. Another strain with different MHC II Type as backup: Live cells (about $10^6$ per mouse) plus Freund's adjuvant. Cells are destroyed during emulsifying antigen.

On the first day, pre-immune bleeds are taken. Cells (about 20 million) are harvested and washed 3× with large volume (40 ml) of PBS, and re-suspended in PBS. Cell suspension is mixed with equal amount of Complete Freund's adjuvant (CFA), emulsified and injected about 5 millions of cells per mouse intraperitoneally.

The Day 1 procedure was repeated over the next few weeks (except no adjuvant every other 2 weeks) until a specific antibody titer of >1:50,000 is reached.

Tail bleeds were taken 7-10 days after the third, sixth and ninth immunizations and will be tested by whole cell ELISA against immunogen-expressing and non-expressing cells. The cells used in whole cell ELISA ideally should be different from immunogen. Best responders (antibody titer>1:50,000) against desired antigen is expected.

Final boost was given to the best responder(s), 2.5 millions of cells iv and 2.5 millions of cells ip 3-4 days before the hybridoma fusion.

Titering of sera. Serum titers for individual mice within each immunization group were determined in duplicate against the corresponding screening antigens (both cells expressing and non-expressing desired GPCR). Groups of mice that failed to show titers after extended periods of immunization will be terminated.

Lymphoid organ harvest. Immunoresponsive mice as determined by titering were used for hybridoma generation and the designated lymphoid organs (spleen in one embodiment) harvested and processed using conventional practices for B cell isolation.

Fusion. The fusion was done the same day following a standard hybridoma fusion protocol. SP2/0 mouse myeloma cell line will be used as fusion partner. The plated fusion products (10-20 plates per fusion) were plated at intermediate density (not more than 10^7 cells per plate), and then cultured for 11-14 days prior to screening.

Primary screening. Cell culture supernatants were tested against the relevant screening antigens with a whole cell ELISA protocol. Anti-mouse IgG antibody-enzyme reporter conjugate were used to detect antigen specific immunoreactivity in the wells and identify those of interest for retesting and potential cloning. Following data analysis, all strong positive lineages were picked into 24-well cell culture plates.

Cell expansion. The cells in 24-well cell culture plates were cultured to exhaustion and cell culture supernatants (~2 ml) were recovered to verify the original screening antigen reactivities.

Secondary Screening. All 24-well cell culture supernatants were re-tested against the relevant screening antigens following the protocol in Appendix 3 and with the desired applications, such as, Western Blot, ImmunoPrecipitation, Flow Cytometry and immunohistochemistry. Cell lines were also banked at this stage. This activity at times required up to 14 days. Following data analysis, line supernatants whose screening antigen reactivity were verified were advanced to subcloning.

Subcloning. Subcloning by limiting dilution for all hybridoma lines selected were conducted. If there were multiple clones that showed exactly the same functionalities, only the two best were cloned. Up to 3 daughter clones were selected from each linage, based on visual inspection, production and immunoreactivity. Clones were screened with the relevant screening antigen approximately 10-12 days post subcloning, depending on individual growth rates in culture. The complete subclonings and screening procedures required up to 4 weeks, depending how many rounds of subclonings were needed.

The final clones from previous work were processed to scaling up in this phase through ascites generation. Antibody purification was needed depending on the result of application.

Example VI

Hybridoma Screening

ELISA plates (Corning 3369 or similar) were coated with 100 μl of high-density (concentration to be decided) cells expressing desired proteins (in PBS). The plates were allowed to air-dry inside a cell culture hood at room temperature for overnight. Negative control cells (non-transfected cells) were processed in parallel with the transfected cells.

After overnight culture, the plates were washed three times with PBS+0.05% Tween-20 (PBST) and then blocked with 250l/well of PBST-5% skim milk). The plates were then incubated at room temperature for 1 hour (or at 4° C. overnight).

After incubation, the PBST-5% skim Milk was discarded and 50 μl/well cell culture supernatant or other form of testing antibodies was added, followed by another incubation for one hour at room temperature (or overnight at 4° C.).

After another 3× wash with PBST, 1:10,000 diluted goat anti-mouse IgG-HRP conjugate (Jackson Immuno 115-036-071 or similar) was added the plates incubated at room temperature for another hour.

After the incubation and a five time wash in PBST, HRP (horseradish peroxidase) substrate, Sigma Fast OPD was added and the plates incubated in the dark at room temperature for 30-60 min.

Plates were read at OD450 with a 96-well colormetric detector if reaction was not stopped, or at OD492 if stopped with 1.25M sulfuric acid.

Example VII

FACS, Sorting Protocol for Establishing Stable Cell Line

This protocol was designed for use in conjunction with an anti-flag-tag antibody (clone M2 from Sigma-Aldrich) and the mammalian cells transfected with pMEX plasmids carrying a full-length GPCR gene. A fraction of cells, 100K cells, were used to determine GPCR expression level by FACS on FACSort (Becton Dickinson) following a 96-well-microtiter-plate (use any U-shape plate) protocol below:

1. Resuspend cells and transfer them to a 15-ml centrifuge tube, 1200 rpm 5 min;
2. Wash cells once with 10 ml of cold PBS;
3. Wash cells with 10 ml of cold PBS+1% BSA (FB);
4. Resuspend the cells with cold FB and add 100 μl per well;
5. 1200 rpm 2 min, and flick the plate;
6. Vortex briefly to suspend the cells;
7. Add 100 μl of M2 antibody (anti-flag-tag) at 10 μg/ml;
8. Put the plate on top of ice for 30 min;
9. Spin-flick to remove M2 antibody;
10. Wash 2× with 250 μl FB;
11. Vortex, add to each well 100 μl of FITC-labeled antibodies (anti-mouse) at about 10 μl per ml (1:100 dilution from a 1 mg/ml product);
12. Put the plate on top of ice for 20 min;
13. Spin-flick, then Wash 2× with 250 μl FB;
14. Resuspend cells in 250 μl FB and transfer cells to FACS tubes;
15. Ready for FACS.

Two to three cells were collected. The collected cells were centrifuged and resuspended in selection medium, and immediately aliquoted 100 μl or one cell per well to 96-well plate. Cell number was estimated based on the number of cells collected during the sorting.

Example VIII

Protocol for Calcium Mobilization Assay

The Gq-coupled GPCRs expressed in CHO or HEK293T or other cells and the GPCRs coupled with other G-proteins were expressed in the cells transfected with chimeric G-proteins. Functional expression was tested using FLIPR Calcium 4 Assay Kit (Molecular Devices) using the standard protocol, which is reproduced as follows:

A. Preparation of Cells
1. Culture adherent cells in 96-well ploy-D-lysine-coated microplates (Sigma, cat# M-5307), to near confluence. CHO cells can be plated at 30,000-40,000 cells per well and grown overnight. HEK293 cells can be plated at 40,000-50,000 cells per well and grown overnight.

B. Preparation of Reagents
2. Make a 250 mM stock of probenecid acid (100×): dissolve in 1 N NaOH and neutralize with equal volume of HBSS/HEPES.
3. Prepare the dye loading solution (for one microplate): add 10 ml of assay buffer and 100 μl of probenecid acid (final concentration: 2.5 mM) stock solution to a vial of dye mix. Vortex for 1 minute to ensure a complete dissolving.

4. Prepare a solution of receptor agonist (3×) in assay buffer with 0.1% BSA. Make serial dilution in 96-well compound plate (VWR #62409-112, NUNC, V-bottom)

C. Assay

5. Remove the growth medium from the adherent cell cultures. Quickly but carefully add 100 μl of the dye loading solution to each well of a 96-well plate.
6. Incubate the plate at 37° C. for 1 hour.
7. Measure fluorescence using Flexstation (Molecular Device). Instrument settings: excitation at 485 nM, emission at 525 nM, cut-off at 515 nM, compound addition (transfer volume): 50 μl, addition speed (rate): 2, pipette height: 80 μl, assay duration 2-3 minutes.

HBSS/HEPES: Hanks' Balanced Salt Solution (1×) with 20 mM HEPES, pH 7.4.

Although the invention has been described with reference to the presently preferred embodiments, it should be understood that various modifications can be made without departing from the spirit of the invention. Accordingly, the invention is limited only by the following claims.

---

What is claimed is:

1. An expression vector comprising nucleotides 1-1197 of SEQ ID NO 19; a nucleic acid sequence encoding a GPCR polypeptide; and nucleotides 1643-5796 of SEQ ID NO: 19; wherein the expression vector facilitates expression of at least 150,000 copies of the GPCR polypeptide on the cytoplasmic membrane of a cell.

2. The vector of claim 1, wherein the GPCR polypeptide is a member of a GPCR family selected from: an anaphylatoxin receptor, an apelin receptor, a bombesin receptor, a cannabinoid receptor, a chemokine receptor, a free fatty acid receptor, a galanin receptor, a glucagon receptor, a glycoprotein hormone receptor, a leukotriene/lipoxin receptor, a lysophospholipid receptor, a melanin-concentrating hormone receptor, a melatonin receptor, a N-formylpeptide receptor, a neuromedin U receptor, a neuropeptide S receptor, a neuropeptide W/neuropeptide B receptor, a neuropeptide Y receptor, an opioid receptor, a platelet activating factor receptor, a prolactin releasing peptide receptor, a prostanoid receptor, a PTH receptor, a purinergic receptor, a tachykinin receptor, a trace amine receptor, and a urotensin receptor.

3. The vector of claim 1, wherein the GPCR polypeptide is an orphan GPCR.

4. The vector of claim 1, wherein the GPCR polypeptide is selected from: C3aR, APJ, BB1, BB3, GPR55, CCR1, CCR5, CCR7, CCR9, CMKLR1, CXCR3, CXCR4, FFA1, FFA2, GAL1, GAL2, GAL3, GHRH, TSH, ALX, BLT1, BLT2, CysLT1, LPA2, LPA3, MCH1, MT2, FPR1, NMU1, NPS, NPS(1), NPS(2), NPS Ile107, NPBW1, NPBW2, delta, kappa, mu, NOP, GPR37L1, GPR84, MRGX1, MRGX2, PSGR, PAF, PRP, DP, EP1, GPR44, PTH2, P2Y12, NK2, NK3, TM, C5AR, and PAR2.

5. The vector of claim 1, wherein the GPCR polypeptide comprises an amino acid sequence selected from SEQ ID NO: 1, SEQ ID NO:3, SEQ ID NO: 5, SEQ ID NO: 7, SEQ ID NO: 9, SEQ ID NO: 11, SEQ ID NO: 13, SEQ ID NO: 15, and SEQ ID NO: 17.

6. The vector of claim 1, wherein said nucleic acid sequence encoding the GPCR polypeptide is selected from: SEQ ID NO: 2, SEQ ID NO: 4, SEQ ID NO: 6, SEQ ID NO: 8, SEQ ID NO: 12, SEQ ID NO: 14, SEQ ID NO: 16, and SEQ ID NO: 18.

7. An expression vector comprising SEQ ID NO:19.

8. An isolated recombinant cell comprising:
an expression vector comprising nucleotides 1-1197 of SEQ ID NO 19; a nucleic acid sequence encoding a GPCR polypeptide; and nucleotides 1643-5796 of SEQ ID NO: 19;

wherein the expression vector facilitates expression of at least 150,000 copies of the GPCR polypeptide on the cytoplasmic membrane of the cell.

9. The recombinant cell of claim 8, wherein said cell expresses said GPCR polypeptide at a range of 150,000 copies to 2,000,000 copies per cell.

10. The recombinant cell of claim 8, wherein said cell expresses said GPCR polypeptide at a range of 200,000 copies to 2,000,000 copies per cell.

11. The recombinant cell of claim 8, wherein said cell expresses said GPCR polypeptide at a range of 400,000 copies to 2,000,000 copies per cell.

12. The recombinant cell of claim 8, wherein said cell expresses said GPCR polypeptide at a range of 800,000 copies to 2,000,000 copies per cell.

13. The recombinant cell of claim 8, wherein said cell expresses said GPCR polypeptide at a range of 1,000,000 copies to 2,000,000 copies per cell.

14. The recombinant cell of claim 8, wherein said cell expresses said GPCR polypeptide at a range of 1,500,000 copies to 2,000,000 copies per cell.

15. The recombinant cell of claim 8, wherein said cell is a member selected from the group CHO, HEK293T, C6, RH7777, SW480, VS35, and 1321N1 cells.

16. The vector of claim 8, wherein the GPCR polypeptide comprises an amino acid sequence selected from SEQ ID NO: 1, SEQ ID NO:3, SEQ ID NO: 5, SEQ ID NO: 7, SEQ ID NO: 9, SEQ ID NO: 11, SEQ ID NO: 13, SEQ ID NO: 15, and SEQ ID NO: 17.

17. The recombinant cell of claim 8, wherein said nucleic acid sequence encoding the GPCR polypeptide is selected from: SEQ ID NO: 2, SEQ ID NO: 4, SEQ ID NO: 6, SEQ ID NO: 8, SEQ ID NO: 12, SEQ ID NO: 14, SEQ ID NO: 16, and SEQ ID NO: 18.

18. A method of producing a GPCR polypeptide, said method comprising culturing the recombinant cell of claim 8 in vitro under conditions suitable for expression of the GPCR polypeptide; and recovering the GPCR polypeptide.

19. The method of claim 18, wherein said cell is a mammalian cell.

20. The method of claim 18, wherein said cell is selected from CHO, HEK293T, C6, RH7777, SW480, VS35, and 1321N1.

21. The method of claim 18, wherein said nucleic acid sequence encoding the GPCR polypeptide is selected from: SEQ ID NO: 2, SEQ ID NO: 4, SEQ ID NO: 6, SEQ ID NO: 8, SEQ ID NO: 12, SEQ ID NO: 14, SEQ ID NO: 16, and SEQ ID NO: 18.

22. A method of screening for a therapeutic candidate comprising:
culturing the recombinant cell of claim 10 in vitro under conditions suitable for expression of the GPCR polypeptide;
b) contacting a test entity with a region of said GPCR polypeptide, wherein said region presents a fragment of said GPCR polypeptide sufficient for said test entity to interact detectably with said fragment; and
c) detecting interaction of said test entity with said fragment, thereby identifying said test entity as said therapeutic candidate.

23. The method of claim 22, wherein detecting interaction of said test entity with said fragment comprises use of a fluorescent, chemical, radiological, or enzymatic reporter.

24. The method of claim 22, wherein said test entity is contacted with a membrane extract of said recombinant cell.

25. The method of claim 22, wherein said method employs a high, throughput screen for detecting interaction of said test entity with said fragment.

26. A method for producing a functional assay cell line comprising:
a) producing a cell line comprising the recombinant cell of claim 8 by culturing the cell in vitro under conditions suitable for expression of the GPCR polypeptide;
b) coupling a functional reporter to the binding of a ligand to said GPCR polypeptide, such that binding between said ligand and said GPCR polypeptide is detectable as a reporter activity readout.

27. The method of claim 26, wherein said reporter activity readout comprises detection of second messenger activity.

28. The method of claim 27, wherein said second messenger activity comprises: a change in intracellular calcium levels, cAMP activity, and NFAT or CRE, driven beta-lactamase.

29. The method of claim 26, wherein said reporter activity readout comprises detection of GFP, luciferase, or a radiolabeled molecule.

30. A method of using a GPCR-expressing cell line to identify a test compound which modulates activity of said GPCR comprising:
a) producing a cell line comprising the recombinant cell of claim 8 by culturing the cell in vitro under conditions suitable for expression of the GPCR polypeptide;
b) measuring second messenger activity in said cell line in the absence of said test compound, thereby obtaining a first measurement;
c) measuring second messenger activity in said cell line in the presence of said test compound, thereby obtaining a second measurement; and
d) comparing said first measurement and said second measurement and identifying those compounds that result in a difference between said first measurement and said second measurement as test compounds that modulate the activity of said GPCR.

31. The method of claim 30, wherein said second messenger activity comprises a rise in intracellular calcium.

32. The method of claim 30, wherein said second messenger activity comprises a change in intracellular cAMP levels.

33. The method of claim 30, wherein said method includes high, throughput screening methods to detect said second messenger activity.

* * * * *

SEQUENCE LISTING

<160> NUMBER OF SEQ ID NOS: 20

<210> SEQ ID NO 1
<211> LENGTH: 350
<212> TYPE: PRT
<213> ORGANISM: Artificial Sequence
<220> FEATURE:
<223> OTHER INFORMATION: GPCR C5AR

<400> SEQUENCE: 1

```
Met Asn Ser Phe Asn Tyr Thr Thr Pro Asp Tyr Gly His Tyr Asp Asp
1               5                   10                  15

Lys Asp Thr Leu Asp Leu Asn Thr Pro Val Asp Lys Thr Ser Asn Thr
            20                  25                  30

Leu Arg Val Pro Asp Ile Leu Ala Leu Val Ile Phe Ala Val Val Phe
        35                  40                  45

Leu Val Gly Val Leu Gly Asn Ala Leu Val Val Trp Val Thr Ala Phe
    50                  55                  60

Glu Ala Lys Arg Thr Ile Asn Ala Ile Trp Phe Leu Asn Leu Ala Val
65                  70                  75                  80

Ala Asp Phe Leu Ser Cys Leu Ala Leu Pro Ile Leu Phe Thr Ser Ile
                85                  90                  95

Val Gln His His His Trp Pro Phe Gly Gly Ala Ala Cys Ser Ile Leu
            100                 105                 110

Pro Ser Leu Ile Leu Leu Asn Met Tyr Ala Ser Ile Leu Leu Leu Ala
        115                 120                 125

Thr Ile Ser Ala Asp Arg Phe Leu Leu Val Phe Lys Pro Ile Trp Cys
    130                 135                 140

Gln Asn Phe Arg Gly Ala Gly Leu Ala Trp Ile Ala Cys Ala Val Ala
145                 150                 155                 160

Trp Gly Leu Ala Leu Leu Leu Thr Ile Pro Ser Phe Leu Tyr Arg Val
                165                 170                 175

Val Arg Glu Glu Tyr Phe Pro Pro Lys Val Leu Cys Gly Val Asp Tyr
            180                 185                 190

Ser His Asp Lys Arg Arg Glu Arg Ala Val Ala Ile Val Arg Leu Val
        195                 200                 205

Leu Gly Phe Leu Trp Pro Leu Leu Thr Leu Thr Ile Cys Tyr Thr Phe
    210                 215                 220

Ile Leu Leu Arg Thr Trp Ser Arg Arg Ala Thr Arg Ser Thr Lys Thr
225                 230                 235                 240

Leu Lys Val Val Val Ala Val Val Ala Ser Phe Phe Ile Phe Trp Leu
                245                 250                 255

Pro Tyr Gln Val Thr Gly Ile Met Met Ser Phe Leu Glu Pro Ser Ser
            260                 265                 270
```

-continued

```
Pro Thr Phe Leu Leu Asn Lys Leu Asp Ser Leu Cys Val Ser Phe
        275                 280                 285

Ala Tyr Ile Asn Cys Cys Ile Asn Pro Ile Ile Tyr Val Val Ala Gly
        290                 295                 300

Gln Gly Phe Gln Gly Arg Leu Arg Lys Ser Leu Pro Ser Leu Leu Arg
305                 310                 315                 320

Asn Val Leu Thr Glu Glu Ser Val Val Arg Glu Ser Lys Ser Phe Thr
                325                 330                 335

Arg Ser Thr Val Asp Thr Met Ala Gln Lys Thr Gln Ala Val
                340                 345                 350

<210> SEQ ID NO 2
<211> LENGTH: 1053
<212> TYPE: DNA
<213> ORGANISM: Artificial Sequence
<220> FEATURE:
<223> OTHER INFORMATION: GPCR C5AR

<400> SEQUENCE: 2
atgaactcct tcaattatac caccctgat tatgggcact atgatgacaa ggataccctg      60
gacctcaaca cccctgtgga taaaacttct aacacgctgc gtgttccaga catcctggcc     120
ttggtcatct ttgcagtcgt cttcctggtg ggagtgctgg gcaatgccct ggtggtctgg     180
gtgacggcat tcgaggccaa gcggaccatc aatgccatct ggttcctcaa cttggcggta     240
gccgacttcc tctcctgcct ggcgctgccc atcttgttca cgtccattgt acagcatcac     300 cactggcccct ttggcggggc cgcctgcagc atcctgccct ccctcatcct gctcaacatg     360
tacgccagca tcctgctcct ggccaccatc agcgccgacc gctttctgct ggtgtttaaa     420
cccatctggt gccagaactt ccgaggggcc ggcttggcct ggatcgcctg tgccgtggct     480
tggggtttag ccctgctgct gaccataccc tccttcctgt accgggtggt ccggggaggag     540 tactttccac caaaggtgtt gtgtggcgtg gactacagcc acgacaaacg gcgggagcga     600
gccgtggcca tcgtccggct ggtcctgggc ttcctgtggc tctactcac gctcacgatt     660 tgttacactt tcatcctgct ccggacgtgg agccgcaggg ccacgcggtc caccaagaca     720
ctcaaggtgg tggtggcagt ggtggccagt ttctttatct tctggttgcc ctaccaggtg     780
acggggataa tgatgtcctt cctggagcca tcgtcaccca ccttcctgct gctgaataag     840
ctggactccc tgtgtgtctc ctttgcctac atcaactgct gcatcaaccc catcatctac     900
gtggtggccg gccagggctt ccagggccga ctgcggaaat ccctcccag cctcctccgg     960 aacgtgttga ctgaagagtc cgtggttagg gagagcaagt cattcacgcg ctccacagtg    1020
gacactatgg cccagaagac ccaggcagtg tag                                 1053

<210> SEQ ID NO 3
<211> LENGTH: 426
<212> TYPE: PRT
<213> ORGANISM: Artificial Sequence
<220> FEATURE:
<223> OTHER INFORMATION: GPCR NMUR1

<400> SEQUENCE: 3

Met Thr Pro Leu Cys Leu Asn Cys Ser Val Leu Pro Gly Asp Leu Tyr
1               5                   10                  15

Pro Gly Gly Ala Arg Asn Pro Met Ala Cys Asn Gly Ser Ala Ala Arg
                20                  25                  30

Gly His Phe Asp Pro Glu Asp Leu Asn Leu Thr Asp Glu Ala Leu Arg
            35                  40                  45
```

```
Leu Lys Tyr Leu Gly Pro Gln Gln Thr Glu Leu Phe Met Pro Ile Cys
     50                  55                  60

Ala Thr Tyr Leu Leu Ile Phe Val Val Gly Ala Val Gly Asn Gly Leu
 65                  70                  75                  80

Thr Cys Leu Val Ile Leu Arg His Lys Ala Met Arg Thr Pro Thr Asn
                 85                  90                  95

Tyr Tyr Leu Phe Ser Leu Ala Val Ser Asp Leu Leu Val Leu Leu Val
            100                 105                 110

Gly Leu Pro Leu Glu Leu Tyr Glu Met Trp His Asn Tyr Pro Phe Leu
        115                 120                 125

Leu Gly Val Gly Gly Cys Tyr Phe Arg Thr Leu Leu Phe Glu Met Val
    130                 135                 140

Cys Leu Ala Ser Val Leu Asn Val Thr Ala Leu Ser Val Glu Arg Tyr
145                 150                 155                 160

Val Ala Val Val His Pro Leu Gln Ala Arg Ser Met Val Thr Arg Ala
                165                 170                 175

His Val Arg Arg Val Leu Gly Ala Val Trp Gly Leu Ala Met Leu Cys
            180                 185                 190

Ser Leu Pro Asn Thr Ser Leu His Gly Ile Gln Gln Leu His Val Pro
        195                 200                 205

Cys Arg Gly Pro Val Pro Asp Ser Ala Val Cys Met Leu Val Arg Pro
    210                 215                 220

Arg Ala Leu Tyr Asn Met Val Val Gln Thr Thr Ala Leu Leu Phe Phe
225                 230                 235                 240

Cys Leu Pro Met Ala Ile Met Ser Val Leu Tyr Leu Leu Ile Gly Leu
                245                 250                 255

Arg Leu Arg Arg Glu Arg Leu Leu Met Gln Glu Ala Lys Gly Arg
            260                 265                 270

Gly Ser Ala Ala Ala Arg Ser Arg Tyr Thr Cys Arg Leu Gln Gln His
        275                 280                 285

Asp Arg Gly Arg Arg Gln Val Thr Lys Met Leu Phe Val Leu Val Val
    290                 295                 300

Val Phe Gly Ile Cys Trp Ala Pro Phe His Ala Asp Arg Val Met Trp
305                 310                 315                 320

Ser Val Val Ser Gln Trp Thr Asp Gly Leu His Leu Ala Phe Gln His
                325                 330                 335

Val His Val Ile Ser Gly Ile Phe Phe Tyr Leu Gly Ser Ala Ala Asn
            340                 345                 350

Pro Val Leu Tyr Ser Leu Met Ser Ser Arg Phe Arg Glu Thr Phe Gln
        355                 360                 365

Glu Ala Leu Cys Leu Gly Ala Cys Cys His Arg Leu Arg Pro Arg His
    370                 375                 380

Ser Ser His Ser Leu Ser Arg Met Thr Thr Gly Ser Thr Leu Cys Asp
385                 390                 395                 400

Val Gly Ser Leu Gly Ser Trp Val His Pro Leu Ala Gly Asn Asp Gly
                405                 410                 415

Pro Glu Ala Gln Gln Glu Thr Asp Pro Ser
            420                 425

<210> SEQ ID NO 4
<211> LENGTH: 1281
<212> TYPE: DNA
<213> ORGANISM: Artificial Sequence
<220> FEATURE:
```

<223> OTHER INFORMATION: GPCR NMUR1

<400> SEQUENCE: 4

```
atgactcctc tctgcctcaa ttgctctgtc ctccctggag acctgtaccc aggggggtgca    60
aggaacccca tggcttgcaa tggcagtgcg gccaggggggc actttgaccc tgaggacttg   120
aacctgactg acgaggcact gagactcaag tacctggggc cccagcagac agagctgttc   180
atgcccatct gtgccacata cctgctgatc ttcgtggtgg gcgctgtggg caatgggctg   240
acctgtctgg tcatcctgcg ccacaaggcc atgcgcacgc taccaactta ctacctcttc   300
agcctggccg tgtcggacct gctggtgctg ctggtgggcc tgcccctgga gctctatgag   360
atgtggcaca actacccctt cctgctgggc gttggtggct gctatttccg cacgctactg   420
tttgagatgg tctgcctggc ctcagtgctc aacgtcactg ccctgagcgt ggaacgctat   480
gtggccgtgg tgcacccact ccaggccagg tccatggtga cgcgggccca tgtgcgccga   540
gtgcttgggg ccgtctgggg tcttgccatg ctctgctccc tgcccaacac cagcctgcac   600
ggcatccagc agctgcacgt gccctgccgg ggcccagtgc cagactcagc tgtttgcatg   660
ctggtccgcc cacgggccct ctacaacatg gtagtgcaga ccaccgcgct gctcttcttc   720
tgcctgccca tggccatcat gagcgtgctc tacctgctca ttgggctgcg actgcggcgg   780
gagaggctgc tgctcatgca ggaggccaag ggcagggggct ctgcagcagc caggtccaga   840
tacacctgca ggctccagca gcacgatcgg ggccggagac aagtgaccaa gatgctgttt   900
gtcctggtcg tggtgtttgg catctgctgg gcccccgttcc acgccgaccg cgtcatgtgg   960
agcgtcgtgt cacagtggac agatggcctg cacctggcct tccagcacgt gcacgtcatc  1020
tccggcatct tcttctacct gggctcggcg gccaaccccg tgctctatag cctcatgtcc  1080
agccgcttcc gagagacctt ccaggaggcc ctgtgcctcg gggcctgctg ccatcgcctc  1140
agaccccgcc acagctccca cagcctcagc aggatgacca caggcagcac cctgtgtgat  1200
gtgggctccc tgggcagctg ggtccaccccc ctggctggga cgatggccc agaggcgcag  1260
caagagaccg atccatcctg a                                             1281
```

<210> SEQ ID NO 5
<211> LENGTH: 377
<212> TYPE: PRT
<213> ORGANISM: Artificial Sequence
<220> FEATURE:
<223> OTHER INFORMATION: GPCR P2RY2

<400> SEQUENCE: 5

```
Met Ala Ala Asp Leu Gly Pro Trp Asn Asp Thr Ile Asn Gly Thr Trp
  1               5                  10                  15

Asp Gly Asp Glu Leu Gly Tyr Arg Cys Arg Phe Asn Glu Asp Phe Lys
             20                  25                  30

Tyr Val Leu Leu Pro Val Ser Tyr Gly Val Val Cys Val Pro Gly Leu
         35                  40                  45

Cys Leu Asn Ala Val Ala Leu Tyr Ile Phe Leu Cys Arg Leu Lys Thr
     50                  55                  60

Trp Asn Ala Ser Thr Thr Tyr Met Phe His Leu Ala Val Ser Asp Ala
 65                  70                  75                  80

Leu Tyr Ala Ala Ser Leu Pro Leu Leu Val Tyr Tyr Ala Arg Gly
             85                  90                  95

Asp His Trp Pro Phe Ser Thr Val Leu Cys Lys Leu Val Arg Phe Leu
            100                 105                 110
```

```
Phe Tyr Thr Asn Leu Tyr Cys Ser Ile Leu Phe Leu Thr Cys Ile Ser
        115                 120                 125

Val His Arg Cys Leu Gly Val Leu Arg Pro Leu Arg Ser Leu Arg Trp
    130                 135                 140

Gly Arg Ala Arg Tyr Ala Arg Arg Val Ala Gly Ala Val Trp Val Leu
145                 150                 155                 160

Val Leu Ala Cys Gln Ala Pro Val Leu Tyr Phe Val Thr Thr Ser Ala
                165                 170                 175

Arg Gly Gly Arg Val Thr Cys His Asp Thr Ser Ala Pro Glu Leu Phe
            180                 185                 190

Ser Arg Phe Val Ala Tyr Ser Ser Val Met Leu Gly Leu Leu Phe Ala
        195                 200                 205

Val Pro Phe Ala Val Ile Leu Val Cys Tyr Val Leu Met Ala Arg Arg
    210                 215                 220

Leu Leu Lys Pro Ala Tyr Gly Thr Ser Gly Gly Leu Pro Arg Ala Lys
225                 230                 235                 240

Arg Lys Ser Val Arg Thr Ile Ala Val Val Leu Ala Val Phe Ala Leu
                245                 250                 255

Cys Phe Leu Pro Phe His Val Thr Arg Thr Leu Tyr Tyr Ser Phe Arg
            260                 265                 270

Ser Leu Asp Leu Ser Cys His Thr Leu Asn Ala Ile Asn Met Ala Tyr
        275                 280                 285

Lys Val Thr Arg Pro Leu Ala Ser Ala Asn Ser Cys Leu Asp Pro Val
    290                 295                 300

Leu Tyr Phe Leu Ala Gly Gln Arg Leu Val Arg Phe Ala Arg Asp Ala
305                 310                 315                 320

Lys Pro Pro Thr Gly Pro Ser Pro Ala Thr Pro Ala Arg Arg Arg Leu
                325                 330                 335

Gly Leu Arg Arg Ser Asp Arg Thr Asp Met Gln Arg Ile Glu Asp Val
            340                 345                 350

Leu Gly Ser Ser Glu Asp Ser Arg Arg Thr Glu Ser Thr Pro Ala Gly
        355                 360                 365

Ser Glu Asn Thr Lys Asp Ile Arg Leu
    370                 375

<210> SEQ ID NO 6
<211> LENGTH: 1134
<212> TYPE: DNA
<213> ORGANISM: Artificial Sequence
<220> FEATURE:
<223> OTHER INFORMATION: GPCR P2RY2

<400> SEQUENCE: 6
atggcagcag acctgggccc ctggaatgac accatcaatg gcacctggga tggggatgag      60
ctgggctaca ggtgccgctt caacgaggac ttcaagtacg tgctgctgcc tgtgtcctac     120
ggcgtggtgt gcgtgcctgg gctgtgtctg aacgccgtgg cgctctacat cttcttgtgc     180
cgcctcaaga cctggaatgc gtccaccaca tatatgttcc acctggctgt gtctgatgca     240
ctgtatgcgg cctccctgcc gctgctggtc tattactacg cccgcggcga ccactggccc     300
ttcagcacgg tgctctgcaa gctggtgcgc ttcctcttct acaccaacct ttactgcagc     360
atcctcttcc tcacctgcat cagcgtgcac cggtgtctgg gcgtcttacg acctctgcgc     420
tccctgcgct ggggccgggc ccgctacgct cgccgggtgg ccggggccgt gtgggtgttg     480
gtgctggcct gccaggcccc cgtgctctac tttgtcacca ccagcgcgcg cgggggccgc     540
```

```
gtaacctgcc acgacacctc ggcacccgag ctcttcagcc gcttcgtggc ctacagctca    600
gtcatgctgg gcctgctctt cgcggtgccc tttgccgtca tccttgtctg ttacgtgctc    660
atggctcggc gactgctaaa gccagcctac gggacctcgg gcggcctgcc tagggccaag    720
cgcaagtccg tgcgcaccat cgccgtggtg ctggctgtct tcgccctctg cttcctgcca    780
ttccacgtca cccgcaccct ctactactcc ttccgctcgc tggacctcag ctgccacacc    840
ctcaacgcca tcaacatggc ctacaaggtt acccggccgc tggccagtgc taacagttgc    900
cttgaccccg tgctctactt cctggctggg cagaggctcg tacgctttgc ccgagatgcc    960 aagcccaccca ctggccccag ccctgccacc ccggctcgcc gcaggctggg cctgcgcaga   1020
tccgacagaa ctgacatgca gaggatagaa gatgtgttgg gcagcagtga ggactctagg   1080
cggacagagt ccacgccggc tggtagcgag aacactaagg acattcggct gtag         1134
```

<210> SEQ ID NO 7
<211> LENGTH: 342
<212> TYPE: PRT
<213> ORGANISM: Artificial Sequence
<220> FEATURE:
<223> OTHER INFORMATION: GPCR PTAFR

<400> SEQUENCE: 7

```
Met Glu Pro His Asp Ser Ser His Met Asp Ser Glu Phe Arg Tyr Thr
 1               5                  10                  15

Leu Phe Pro Ile Val Tyr Ser Ile Ile Phe Val Leu Gly Val Ile Ala
                20                  25                  30

Asn Gly Tyr Val Leu Trp Val Phe Ala Arg Leu Tyr Pro Cys Lys Lys
            35                  40                  45

Phe Asn Glu Ile Lys Ile Phe Met Val Asn Leu Thr Met Ala Asp Met
        50                  55                  60

Leu Phe Leu Ile Thr Leu Pro Leu Trp Ile Val Tyr Tyr Gln Asn Gln
65                  70                  75                  80

Gly Asn Trp Ile Leu Pro Lys Phe Leu Cys Asn Val Ala Gly Cys Leu
                85                  90                  95

Phe Phe Ile Asn Thr Tyr Cys Ser Val Ala Phe Leu Gly Val Ile Thr
            100                 105                 110

Tyr Asn Arg Phe Gln Ala Val Thr Arg Pro Ile Lys Thr Ala Gln Ala
        115                 120                 125

Asn Thr Arg Lys Arg Gly Ile Ser Leu Ser Leu Val Ile Trp Val Ala
    130                 135                 140

Ile Val Gly Ala Ala Ser Tyr Phe Leu Ile Leu Asp Ser Thr Asn Thr
145                 150                 155                 160

Val Pro Asp Ser Ala Gly Ser Gly Asn Val Thr Arg Cys Phe Glu His
                165                 170                 175

Tyr Glu Lys Gly Ser Val Pro Val Leu Ile Ile His Ile Phe Ile Val
            180                 185                 190

Phe Ser Phe Phe Leu Val Phe Leu Ile Ile Leu Phe Cys Asn Leu Val
        195                 200                 205

Ile Ile Arg Thr Leu Leu Met Gln Pro Val Gln Gln Arg Asn Ala
    210                 215                 220

Glu Val Lys Arg Arg Ala Leu Trp Met Val Cys Thr Val Leu Ala Val
225                 230                 235                 240

Phe Ile Ile Cys Phe Val Pro His His Val Val Gln Leu Pro Trp Thr
                245                 250                 255

Leu Ala Glu Leu Gly Phe Gln Asp Ser Lys Phe His Gln Ala Ile Asn
```

-continued

```
                260                 265                 270
Asp Ala His Gln Val Thr Leu Cys Leu Leu Ser Thr Asn Cys Val Leu
            275                 280                 285

Asp Pro Val Ile Tyr Cys Phe Leu Thr Lys Lys Phe Arg Lys His Leu
        290                 295                 300

Thr Glu Lys Phe Tyr Ser Met Arg Ser Ser Arg Lys Cys Ser Arg Ala
305                 310                 315                 320

Thr Thr Asp Thr Val Thr Glu Val Val Val Pro Phe Asn Gln Ile Pro
                325                 330                 335

Gly Asn Ser Leu Lys Asn
            340

<210> SEQ ID NO 8
<211> LENGTH: 1029
<212> TYPE: DNA
<213> ORGANISM: Artificial Sequence
<220> FEATURE:
<223> OTHER INFORMATION: GPCR PTAFR

<400> SEQUENCE: 8
atggagccac atgactcctc ccacatggac tctgagttcc gatacactct cttcccgatt      60
gtttacagca tcatctttgt gctcggggtc attgctaatg ctacgtgct gtgggtcttt      120 gcccgcctgt acccttgcaa gaaattcaat gagataaaga tcttcatggt gaacctcacc      180
atggcggaca tgctcttctt gatcacccctg ccactttgga ttgtctacta ccaaaaccag      240
ggcaactgga tactccccaa attcctgtgc aacgtggctg gctgccttt cttcatcaac      300 acctactgct ctgtggcctt cctgggcgtc atcacttata accgcttcca ggcagtaact      360
cggcccatca gagactgctca ggccaacacc cgcaagcgtg gcatctcttt gtccttggtc      420
atctgggtgg ccattgtggg agctgcatcc tacttcctca tcctggactc caccaacaca      480
gtgcccgaca gtgctggctc aggcaacgtc actcgctgct tgagcatta cgagaagggc      540 agcgtgccag tcctcatcat ccacatcttc atcgtgttca gcttcttcct ggtcttcctc      600
atcatcctct ctgcaacct ggtcatcatc cgtaccttgc tcatgcagcc ggtgcagcag      660
cagcgcaacg ctgaagtcaa gcgccgggcg ctgtggatgg tgtgcacggt cttggcggtg      720
ttcatcatct gcttcgtgcc ccaccacgtg gtgcagctgc cctggaccct tgctgagctg      780
ggcttccagg acagcaaatt ccaccaggcc attaatgatg cacatcaggt caccctctgc      840
ctccttagca ccaactgtgt cttagaccct gttatctact gtttcctcac caagaagttc      900
cgcaagcacc tcaccgaaaa gttctacagc atgcgcagta gccggaaatg ctcccgggcc      960
accacggata cggtcactga agtggttgtg ccattcaacc agatccctgg caattccctc      1020
aaaaattag                                                             1029

<210> SEQ ID NO 9
<211> LENGTH: 380
<212> TYPE: PRT
<213> ORGANISM: Artificial Sequence
<220> FEATURE:
<223> OTHER INFORMATION: GPCR AGTRL1

<400> SEQUENCE: 9

Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
            20                  25                  30
```

```
Ala Ile Tyr Met Leu Val Phe Leu Leu Gly Thr Thr Gly Asn Gly Leu
         35                  40                  45

Val Leu Trp Thr Val Phe Arg Ser Ser Arg Glu Lys Arg Arg Ser Ala
 50                  55                  60

Asp Ile Phe Ile Ala Ser Leu Ala Val Ala Asp Leu Thr Phe Val Val
 65                  70                  75                  80

Thr Leu Pro Leu Trp Ala Thr Tyr Thr Tyr Arg Asp Tyr Asp Trp Pro
                 85                  90                  95

Phe Gly Thr Phe Phe Cys Lys Leu Ser Ser Tyr Leu Ile Phe Val Asn
                100                 105                 110

Met Tyr Ala Ser Val Phe Cys Leu Thr Gly Leu Ser Phe Asp Arg Tyr
            115                 120                 125

Leu Ala Ile Val Arg Pro Val Ala Asn Ala Arg Leu Arg Leu Arg Val
        130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Ile Phe Pro Tyr Cys Thr Cys Ile Ser Tyr Val Asn Ser Cys Leu
    290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
    370                 375                 380

<210> SEQ ID NO 10
<211> LENGTH: 1143
<212> TYPE: DNA
<213> ORGANISM: Artificial Sequence
<220> FEATURE:
<223> OTHER INFORMATION: GPCR AGTRL1

<400> SEQUENCE: 10
atggaggaag gtggtgattt tgacaactac tatggggcag acaaccagtc tgagtgtgag      60
tacacagact ggaaatcctc gggggcccte atccctgcca tctacatgtt ggtcttcctc     120
```

-continued

```
ctgggcacca cgggcaacgg tctggtgctc tggaccgtgt tcggagcag ccgggagaag    180 aggcgctcag ctgatatctt cattgctagc ctggcggtgg ctgacctgac cttcgtggtg    240
acgctgcccc tgtgggctac ctacacgtac cgggactatg actggccctt gggaccttc    300 ttctgcaagc tcagcagcta cctcatcttc gtcaacatgt acgccagcgt cttctgcctc    360
accggcctca gcttcgaccg ctacctggcc atcgtgaggc cagtggccaa tgctcggctg    420
aggctgcggg tcagcggggc cgtggccacg gcagttcttt gggtgctggc cgccctcctg    480
gccatgcctg tcatggtgtt acgcaccacc ggggacttgg agaacaccac taaggtgcag    540
tgctacatgg actactccat ggtggccact gtgagctcag agtgggcctg ggaggtgggc    600
cttggggtct cgtccaccac cgtgggcttt gtggtgccct tcaccatcat gctgacctgt    660
tacttcttca tcgcccaaac catcgctggc cacttccgca aggaacgcat cgagggcctg    720
cggaagcggc gccggctgct cagcatcatc gtggtgctgg tggtgacctt tgccctgtgc    780
tggatgccct accacctggt gaagacgctg tacatgctgg gcagcctgct gcactggccc    840
tgtgactttg acctcttcct catgaacatc ttccccctact gcacctgcat cagctacgtc    900
aacagctgcc tcaaccccttt cctctatgcc ttttcgacc ccgcttccg ccaggcctgc    960 acctccatgc tctgctgtgg ccagagcagg tgcgcaggca cctcccacag cagcagtggg    1020
gagaagtcag ccagctactc ttcggggcac agccaggggc ccggcccaa catgggcaag    1080 ggtggagaac agatgcacga gaaatccatc ccctacagcc aggagaccct tgtggttgac    1140
tag                                                                 1143
```

<210> SEQ ID NO 11
<211> LENGTH: 482
<212> TYPE: PRT
<213> ORGANISM: Artificial Sequence
<220> FEATURE:
<223> OTHER INFORMATION: GPCR C3AR

<400> SEQUENCE: 11

```
Met Ala Ser Phe Ser Ala Glu Thr Asn Ser Thr Asp Leu Leu Ser Gln
  1               5                  10                  15

Pro Trp Asn Glu Pro Pro Val Ile Leu Ser Met Val Ile Leu Ser Leu
             20                  25                  30

Thr Phe Leu Leu Gly Leu Pro Gly Asn Gly Leu Val Leu Trp Val Ala
         35                  40                  45

Gly Leu Lys Met Gln Arg Thr Val Asn Thr Ile Trp Phe Leu His Leu
     50                  55                  60

Thr Leu Ala Asp Leu Leu Cys Cys Leu Ser Leu Pro Phe Ser Leu Ala
 65                  70                  75                  80

His Leu Ala Leu Gln Gly Gln Trp Pro Tyr Gly Arg Phe Leu Cys Lys
                 85                  90                  95

Leu Ile Pro Ser Ile Ile Val Leu Asn Met Phe Ala Ser Val Phe Leu
            100                 105                 110

Leu Thr Ala Ile Ser Leu Asp Arg Cys Leu Val Val Phe Lys Pro Ile
        115                 120                 125

Trp Cys Gln Asn His Arg Asn Val Gly Met Ala Cys Ser Ile Cys Gly
    130                 135                 140

Cys Ile Trp Val Val Ala Phe Val Met Cys Ile Pro Val Phe Val Tyr
145                 150                 155                 160

Arg Glu Ile Phe Thr Thr Asp Asn His Asn Arg Cys Gly Tyr Lys Phe
                165                 170                 175
```

```
Gly Leu Ser Ser Ser Leu Asp Tyr Pro Asp Phe Tyr Gly Asp Pro Leu
            180                 185                 190
Glu Asn Arg Ser Leu Glu Asn Ile Val Gln Pro Pro Gly Glu Met Asn
        195                 200                 205
Asp Arg Leu Asp Pro Ser Ser Phe Gln Thr Asn Asp His Pro Trp Thr
    210                 215                 220
Val Pro Thr Val Phe Gln Pro Gln Thr Phe Gln Arg Pro Ser Ala Asp
225                 230                 235                 240
Ser Leu Pro Arg Gly Ser Ala Arg Leu Thr Ser Gln Asn Leu Tyr Ser
                245                 250                 255
Asn Val Phe Lys Pro Ala Asp Val Val Ser Pro Lys Ile Pro Ser Gly
            260                 265                 270
Phe Pro Ile Glu Asp His Glu Thr Ser Pro Leu Asp Asn Ser Asp Ala
        275                 280                 285
Phe Leu Ser Thr His Leu Lys Leu Phe Pro Ser Ala Ser Ser Asn Ser
    290                 295                 300
Phe Tyr Glu Ser Glu Leu Pro Gln Gly Phe Gln Asp Tyr Tyr Asn Leu
305                 310                 315                 320
Gly Gln Phe Thr Asp Asp Gln Val Pro Thr Pro Leu Val Ala Ile
                325                 330                 335
Thr Ile Thr Arg Leu Val Val Gly Phe Leu Leu Pro Ser Val Ile Met
            340                 345                 350
Ile Ala Cys Tyr Ser Phe Ile Val Phe Arg Met Gln Arg Gly Arg Phe
        355                 360                 365
Ala Lys Ser Gln Ser Lys Thr Phe Arg Val Ala Val Val Val Ala
    370                 375                 380
Val Phe Leu Val Cys Trp Thr Pro Tyr His Ile Phe Gly Val Leu Ser
385                 390                 395                 400
Leu Leu Thr Asp Pro Glu Thr Pro Leu Gly Lys Thr Leu Met Ser Trp
                405                 410                 415
Asp His Val Cys Ile Ala Leu Ala Ser Ala Asn Ser Cys Phe Asn Pro
            420                 425                 430
Phe Leu Tyr Ala Leu Leu Gly Lys Asp Phe Arg Lys Lys Ala Arg Gln
        435                 440                 445
Ser Ile Gln Gly Ile Leu Glu Ala Ala Phe Ser Glu Glu Leu Thr Arg
    450                 455                 460
Ser Thr His Cys Pro Ser Asn Asn Val Ile Ser Glu Arg Asn Ser Thr
465                 470                 475                 480
Thr Val

<210> SEQ ID NO 12
<211> LENGTH: 1449
<212> TYPE: DNA
<213> ORGANISM: Artificial Sequence
<220> FEATURE:
<223> OTHER INFORMATION: GPCR C3AR

<400> SEQUENCE: 12
atggcgtctt tctctgctga gaccaattca actgacctac tctcacagcc atggaatgag      60
cccccagtaa ttctctccat ggtcattctc agccttactt ttttactggg attgccaggc     120
aatgggctgg tgctgtgggt ggctggcctg aagatgcagc ggacagtgaa cacaatttgg     180
ttcctccacc tcaccttggc ggacctcctc tgctgcctct ccttgccctt ctcgctggct     240
cacttggctc tccagggaca gtggcccta ggcaggttcc tatgcaagct catcccctcc     300
```

```
atcattgtcc tcaacatgtt tgccagtgtc ttcctgctta ctgccattag cctggatcgc    360
tgtcttgtgg tattcaagcc aatctggtgt cagaatcatc gcaatgtagg gatggcctgc    420
tctatctgtg gatgtatctg ggtggtggct tttgtgatgt gcattcctgt gttcgtgtac    480
cgggaaatct tcactacaga caaccataat agatgtggct acaaatttgg tctctccagc    540
tcattagatt atccagactt ttatggagat ccactagaaa acaggtctct tgaaaacatt    600
gttcagccgc tggagaaat gaatgatagg ttagatcctt cctctttcca aacaaatgat    660
catccttgga cagtccccac tgtcttccaa cctcaaacat tcaaagacc ttctgcagat    720 tcactcccta ggggttctgc taggttaaca agtcaaaatc tgtattctaa tgtatttaaa    780
cctgctgatg tggtctcacc taaaatcccc agtgggtttc ctattgaaga tcacgaaacc    840
agcccactgg ataactctga tgcttttctc tctactcatt taaagctgtt ccctagcgct    900
tctagcaatt ccttctacga gtctgagcta ccacaaggtt tccaggatta ttacaattta    960
ggccaattca cagatgacga tcaagtgcca acacccctcg tggcaataac gatcactagg   1020
ctagtggtgg gtttcctgct gccctctgtt atcatgatag cctgttacag cttcattgtc   1080
ttccgaatgc aaaggggccg cttcgccaag tctcagagca aaaccttcg agtggccgtg   1140 gtggtggtgg ctgtctttct tgtctgctgg actccatacc acattttgg agtcctgtca   1200 ttgcttactg acccagaaac tccctggggg aaaactctga tgtcctggga tcatgtatgc   1260
attgctctag catctgccaa tagttgcttt aatccttcc tttatgccct cttggggaaa   1320
gattttagga agaaagcaag gcagtccatt cagggaattc tggaggcagc cttcagtgag   1380
gagctcacac gttccaccca ctgtccctca aacaatgtca tttcagaaag aaatagtaca   1440
actgtgtga                                                          1449
```

```
<210> SEQ ID NO 13
<211> LENGTH: 412
<212> TYPE: PRT
<213> ORGANISM: Artificial Sequence
<220> FEATURE:
<223> OTHER INFORMATION: GPCR CCR5

<400> SEQUENCE: 13
```

```
Met Asp Tyr Gln Val Ser Ser Pro Ile Tyr Asp Ile Asn Tyr Tyr Thr
  1               5                  10                  15

Ser Glu Pro Cys Gln Lys Ile Asn Val Lys Gln Ile Ala Ala Arg Leu
             20                  25                  30

Leu Pro Pro Leu Tyr Ser Leu Val Phe Ile Phe Gly Phe Val Gly Asn
         35                  40                  45

Met Leu Val Ile Leu Ile Leu Ile Asn Cys Lys Arg Leu Lys Ser Met
     50                  55                  60

Thr Asp Ile Tyr Leu Leu Asn Leu Ala Ile Ser Asp Leu Phe Phe Leu
 65                  70                  75                  80

Leu Thr Val Pro Phe Trp Ala His Tyr Ala Ala Ala Gln Trp Asp Phe
                 85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
```

```
            145                 150                 155                 160
Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350

Ala Thr Gly Gly Ala Thr Thr Ala Thr Cys Ala Ala Gly Thr Gly Thr
        355                 360                 365

Cys Ala Ala Gly Thr Cys Cys Ala Ala Thr Cys Thr Ala Thr Gly Ala
    370                 375                 380

Cys Ala Thr Cys Ala Ala Thr Thr Ala Thr Ala Thr Ala Cys Ala
385                 390                 395                 400

Thr Cys Gly Gly Ala Gly Cys Cys Cys Thr Gly Cys
                405                 410
```

<210> SEQ ID NO 14
<211> LENGTH: 999
<212> TYPE: DNA
<213> ORGANISM: Artificial Sequence
<220> FEATURE:
<223> OTHER INFORMATION: GPCR CCR5

<400> SEQUENCE: 14

```
caaaaaatca atgtgaagca aatcgcagcc cgcctcctgc ctccgctcta ctcactggtg      60
ttcatctttg ttttgtggg caacatgctg gtcatcctca tcctgataaa ctgcaaaagg     120
ctgaagagca tgactgacat ctacctgctc aacctggcca tctctgacct gttttcctt     180 cttactgtcc ccttctgggc tcactatgct gccgcccagt gggactttgg aaatacaatg    240
tgtcaactct tgacagggct ctatttata ggcttcttct ctggaatctt cttcatcatc     300
ctcctgacaa tcgataggta cctggctgtc gtccatgctg tgtttgcttt aaaagccagg    360
acggtcacct ttgggtggtg gacaagtgtg atcacttggg tggtggctgt gtttgcgtct    420
ctcccaggaa tcatctttac cagatctcaa aagaaggtc ttcattacac ctgcagctct    480
cattttccat acagtcagta tcaattctgg aagaatttcc agacattaaa gatagtcatc    540
ttggggctgg tcctgccgct gcttgtcatg gtcatctgct actcgggaat cctaaaaact    600
```

-continued

```
ctgcttcggt gtcgaaatga aagaagagg cacagggctg tgaggcttat cttcaccatc    660
atgattgttt attttctctt ctgggctccc tacaacattg tccttctcct gaacaccttc    720
caggaattct ttggcctgaa taattgcagt agctctaaca ggttggacca agctatgcag    780
gtgacagaga ctcttgggat gacgcactgc tgcatcaacc ccatcatcta tgcctttgtc    840
ggggagaagt tcagaaacta cctcttagtc ttcttccaaa agcacattgc caaacgcttc    900
tgcaaatgct gttctatttt ccagcaagag gctcccgagc gagcaagctc agtttacacc    960
cgatccactg gggagcagga aatatctgtg ggcttgtga                           999
```

<210> SEQ ID NO 15
<211> LENGTH: 352
<212> TYPE: PRT
<213> ORGANISM: Artificial Sequence
<220> FEATURE:
<223> OTHER INFORMATION: GPCR CXCR4

<400> SEQUENCE: 15

```
Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
        50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285
```

-continued

```
Ala Leu Ala Phe Phe His Cys Cys Leu Asn Pro Ile Leu Tyr Ala Phe
    290                 295                 300
Leu Gly Ala Lys Phe Lys Thr Ser Ala Gln His Ala Leu Thr Ser Val
305                 310                 315                 320
Ser Arg Gly Ser Ser Leu Lys Ile Leu Ser Lys Gly Lys Arg Gly Gly
                325                 330                 335
His Ser Ser Val Ser Thr Glu Ser Glu Ser Ser Ser Phe His Ser Ser
            340                 345                 350
```

<210> SEQ ID NO 16
<211> LENGTH: 1059
<212> TYPE: DNA
<213> ORGANISM: Artificial Sequence
<220> FEATURE:
<223> OTHER INFORMATION: GPCR CXCR4

<400> SEQUENCE: 16

```
atggagggga tcagtatata cacttcagat aactacaccg aggaaatggg ctcaggggac    60
tatgactcca tgaaggaacc ctgtttccgt gaagaaaatg ctaatttcaa taaaatcttc   120
ctgcccacca tctactccat catcttctta actggcattg tgggcaatgg attggtcatc   180
ctggtcatgg gttaccagaa gaaactgaga agcatgacgg acaagtacag gctgcacctg   240
tcagtggccg acctcctctt tgtcatcacg cttcccttct gggcagttga tgccgtggca   300
aactggtact ttgggaactt cctatgcaag gcagtccatg tcatctacac agtcaacctc   360
tacagcagtg tcctcatcct ggccttcatc agtctggacc gctacctggc catcgtccac   420
gccaccaaca gtcagaggcc aaggaagctg ttggctgaaa aggtggtcta tgttggcgtc   480
tggatccctg cctcctgct gactattccc gacttcatct ttgccaacgt cagtgaggca   540
gatgacagat atatctgtga ccgcttctac cccaatgact tgtgggtggt tgtgttccag   600
tttcagcaca tcatggttgg ccttatcctg cctggtattg tcatcctgtc ctgctattgc   660
attatcatct ccaagctgtc acactccaag ggccaccaga gcgcaaggc cctcaagacc   720
acagtcatcc tcatcctggc tttcttcgcc tgttggctgc cttactacat gggatcagc   780
atcgactcct tcatcctcct ggaaatcatc aagcaagggt gtgagtttga aacactgtg   840
cacaagtgga tttccatcac cgaggcccta gctttcttcc actgttgtct gaaccccatc   900
ctctatgctt tccttggagc caaatttaaa acctctgccc agcacgcact cacctctgtg   960
agcagagggt ccagcctcaa gatcctctcc aaaggaaagc gaggtggaca ttcatctgtt  1020
tccactgagt ctgagtcttc aagttttcac tccagctaa                         1059
```

<210> SEQ ID NO 17
<211> LENGTH: 397
<212> TYPE: PRT
<213> ORGANISM: Artificial Sequence
<220> FEATURE:
<223> OTHER INFORMATION: GPCR PAR2

<400> SEQUENCE: 17

```
Met Arg Ser Pro Ser Ala Ala Trp Leu Leu Gly Ala Ala Ile Leu Leu
  1               5                  10                  15
Ala Ala Ser Leu Ser Cys Ser Gly Thr Ile Gln Gly Thr Asn Arg Ser
                20                  25                  30
Ser Lys Gly Arg Ser Leu Ile Gly Lys Val Asp Gly Thr Ser His Val
            35                  40                  45
Thr Gly Lys Gly Val Thr Val Glu Thr Val Phe Ser Val Asp Glu Phe
        50                  55                  60
```

Ser Ala Ser Val Leu Thr Gly Lys Leu Thr Thr Val Phe Leu Pro Ile
65                  70                  75                  80

Val Tyr Thr Ile Val Phe Val Gly Leu Pro Ser Asn Gly Met Ala
            85                  90                  95

Leu Trp Val Phe Leu Phe Arg Thr Lys Lys His Pro Ala Val Ile
            100                 105                 110

Tyr Met Ala Asn Leu Ala Leu Ala Asp Leu Leu Ser Val Ile Trp Phe
            115                 120                 125

Pro Leu Lys Ile Ala Tyr His Ile His Gly Asn Asn Trp Ile Tyr Gly
        130                 135                 140

Glu Ala Leu Cys Asn Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
            165                 170                 175

Ile Val Asn Pro Met Gly His Ser Arg Lys Lys Ala Asn Ile Ala Ile
            180                 185                 190

Gly Ile Ser Leu Ala Ile Trp Leu Leu Ile Leu Leu Val Thr Ile Pro
        195                 200                 205

Leu Tyr Val Val Lys Gln Thr Ile Phe Ile Pro Ala Leu Asn Ile Thr
    210                 215                 220

Thr Cys His Asp Val Leu Pro Glu Gln Leu Leu Val Gly Asp Met Phe
225                 230                 235                 240

Asn Tyr Phe Leu Ser Leu Ala Ile Gly Val Phe Leu Phe Pro Ala Phe
            245                 250                 255

Leu Thr Ala Ser Ala Tyr Val Leu Met Ile Arg Met Leu Arg Ser Ser
            260                 265                 270

Ala Met Asp Glu Asn Ser Glu Lys Lys Arg Lys Arg Ala Ile Lys Leu
        275                 280                 285

Ile Val Thr Val Leu Ala Met Tyr Leu Ile Cys Phe Thr Pro Ser Asn
    290                 295                 300

Leu Leu Leu Val Val His Tyr Phe Leu Ile Lys Ser Gln Gly Gln Ser
305                 310                 315                 320

His Val Tyr Ala Leu Tyr Ile Val Ala Leu Cys Leu Ser Thr Leu Asn
            325                 330                 335

Ser Cys Ile Asp Pro Phe Val Tyr Tyr Phe Val Ser His Asp Phe Arg
            340                 345                 350

Asp His Ala Lys Asn Ala Leu Leu Cys Arg Ser Val Arg Thr Val Lys
        355                 360                 365

Gln Met Gln Val Ser Leu Thr Ser Lys Lys His Ser Arg Lys Ser Ser
    370                 375                 380

Ser Tyr Ser Ser Ser Ser Thr Thr Val Lys Thr Ser Tyr
385                 390                 395

<210> SEQ ID NO 18
<211> LENGTH: 1194
<212> TYPE: DNA
<213> ORGANISM: Artificial Sequence
<220> FEATURE:
<223> OTHER INFORMATION: GPCR PAR2

<400> SEQUENCE: 18
atgcggagcc ccagcgcggc gtggctgctg ggggccgcca tcctgctagc agcctctctc      60
tcctgcagtg gcaccatcca aggaaccaat agatcctcta aaggaagaag ccttattggt     120
aaggttgatg gcacatccca cgtcactgga aaaggagtta cagttgaaac agtcttttct     180

```
gtggatgagt tttctgcatc tgtcctcact ggaaaactga ccactgtctt ccttccaatt      240
gtctacacaa ttgtgtttgt ggtgggtttg ccaagtaacg gcatggccct gtgggtcttt      300
cttttccgaa ctaagaagaa gcaccctgct gtgatttaca tggccaatct ggccttggct      360
gacctcctct ctgtcatctg gttccccttg aagattgcct atcacataca tggcaacaac      420
tggatttatg gggaagctct tgtaatgtg cttattggct ttttctatgg caacatgtac      480
tgttccattc tcttcatgac ctgcctcagt gtgcagaggt attgggtcat cgtgaacccc      540
atggggcact ccaggaagaa ggcaaacatt gccattggca tctccctggc aatatggctg      600
ctgattctgc tggtcaccat ccctttgtat gtcgtgaagc agaccatctt cattcctgcc      660
ctgaacatca cgacctgtca tgatgttttg cctgagcagc tcttggtggg agacatgttc      720
aattacttcc tctctctggc cattggggtc tttctgttcc cagccttcct cacagcctct      780
gcctatgtgc tgatgatcag aatgctgcga tcttctgcca tggatgaaaa ctcagagaag      840
aaaaggaaga gggccatcaa actcattgtc actgtcctgg ccatgtacct gatctgcttc      900
actcctagta accttctgct tgtggtgcat tattttctga ttaagagcca gggccagagc      960
catgtctatg ccctgtacat tgtagccctc tgcctctcta cccttaacag ctgcatcgac     1020 cccttttgtct attactttgt ttcacatgat tcagggatc atgcaaagaa cgctctcctt     1080
tgccgaagtg tccgcactgt aaagcagatg caagtatccc tcacctcaaa gaaacactcc     1140
aggaaatcca gctcttactc ttcaagttca accactgtta agacctccta ttga            1194

<210> SEQ ID NO 19
<211> LENGTH: 5796
<212> TYPE: DNA
<213> ORGANISM: Artificial Sequence
<220> FEATURE:
<223> OTHER INFORMATION: vector pMEX2
<220> FEATURE:
<221> NAME/KEY: misc_feature
<222> LOCATION: (512)...(517)
<223> OTHER INFORMATION: Kozak sequence

<400> SEQUENCE: 19
tcaatattgg ccattagcca tattattcat tggttatata gcataaatca atattggcta       60
ttggccattg catacgttgt atctatatca taatatgtac atttatattg gctcatgtcc      120
aatatgaccg ccatgttggc attgattatt gactagttat taatagtaat caattacggg      180
gtcattagtt catagcccat atatggagtt ccgcgttaca taacttacgg taaatggccc      240
gcctggctga ccgcccaacg acccccgccc attgacgtca ataatgacgt atgttcccat      300
agtaacgcca atagggactt tccattgacg tcaatgggtg gagtatttac ggtaaactgc      360
ccacttggca gtacatcaag tgtatcatat gccaagtccg cccccattg acgtcaatga      420 cggtaaatgg cccgcctggc attatgccca gtacatgacc ttacgggact ttcctacttg      480
gcagtacatc tacgtattag tcatcgctat taccatggtg atgcggtttt ggcagtacac      540
caatgggcgt ggatagcggt ttgactcacg gggatttcca gtctccacc ccattgacgt      600 caatgggagt ttgttttggc accaaaatca acgggacttt ccaaaatgtc gtaacaactg      660
cgatcgcccg ccccgttgac gcaaatgggc ggtaggcgtg tacggtggga ggtctatata      720
agcagagctc gtttagtgaa ccgtcagatc actagaagct ttattgcggt agtttatcac      780
agttaaattg ctaacgcagt cagtgcttct gacacaacag tctcgaactt aagctgcagt      840
gactctctta aggtagcctt gcagaagttg gtcgtgaggc actgggcagg taagtatcaa      900
```

```
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc ctcgagccac catggagaca gacacactcc tgctatgggt actgctgctc   1140
tgggttccag gttccactgg tgatatcgac tataaagatg atgacgacaa gggatcctgc   1200
cccagtcctt tggcttcatc gtgccactgc tgatcatgct gttctgctac ggattcaccc   1260
tgcgtacgct gtttaaggcc cacatggggc agaagcaccg ggccatgcgg gtcatctttg   1320
ctgtcgtcct catcttcctg ctctgctggc tgccctacaa cctggtcctg ctggcagaca   1380
ccctcatgag gacccaggtg atccaggaga cctgtgagcg ccgcaatcac atcgaccggg   1440
ctctggatgc caccgagatt ctgggcatcc ttcacagctg cctcaacccc ctcatctacg   1500
ccttcattgg ccagaagttt cgccatggac tcctcaagat tctagctata catggcttga   1560
tcagcaagga ctccctgccc aaagacagca ggccttcctt tgttggctct tcttcagggc   1620
acacttccac tactctctga tagtcgacgc ggccgcttcc ctttagtgag ggttaatgct   1680
tcgagcagac atgataagat acattgatga gtttggacaa accacaacta gaatgcagtg   1740
aaaaaaatgc tttatttgtg aaatttgtga tgctattgct ttatttgtaa ccattataag   1800
ctgcaataaa caagttaaca acaacaattg cattcatttt atgtttcagg ttcaggggga   1860
gatgtgggag gttttttaaa gcaagtaaaa cctctacaaa tgtggtaaaa tccgataagg   1920
atcgatccgg gctggcgtaa tagcgaagag gcccgcaccg atcgcccttc ccaacagttg   1980
cgcagcctga atggcgaatg gacgcgccct gtagcggcgc attaagcgcg gcgggtgtgg   2040
tggttacgcg cagcgtgacc gctacacttg ccagcgccct agcgcccgct cctttcgctt   2100
tcttcccttc ctttctcgcc acgttcgccg gctttccccg tcaagctcta aatcgggggc   2160
tccctttagg gttccgattt agtgctttac ggcacctcga cccccaaaaa acttgattagg   2220
gtgatggttc acgtagtggg ccatcgccct gatagacggt ttttcgccct ttgacgttgg   2280
agtccacgtt ctttaatagt ggactcttgt tccaaactgg aacaacactc aaccctatct   2340
cggtctattc ttttgattta agggatttt gccgatttc ggcctattgg ttaaaaaatg   2400
agctgattta acaaaaattt aacgcgaatt ttaacaaaat attaacgctt acaatttcct   2460
gatgcggtat tttctcctta cgcatctgtg cggtatttca caccgcatac gcggatctgc   2520
gcagcaccat ggcctgaaat aacctctgaa agaggaactt ggttaggtac cttctgaggc   2580
ggaaagaacc agctgtggaa tgtgtgtcag ttagggtgtg gaaagtcccc aggctcccca   2640
gcaggcagaa gtatgcaaag catgcatctc aattagtcag caaccaggtg tggaaagtcc   2700
ccaggctccc cagcaggcag aagtatgcaa agcatgcatc tcaattagtc agcaaccata   2760
gtcccgcccc taactccgcc catcccgccc ctaactccgc ccagttccgc ccattctccg   2820
ccccatggct gactaatttt ttttatttat gcagaggccg aggccgcctc ggcctctgag   2880
ctattccaga agtagtgagg aggcttttt ggaggcctag gcttttgcaa aaagcttgat   2940
tcttctgaca acagtctc gaacttaagg ctagagccac catgaccgag tacaagccca   3000
cggtgcgcct cgccacccgc gacgacgtcc cagggccgt acgcaccctc gccgccgcgt   3060
tcgccgacta ccccgccacg cgccacaccg tcgatccgga ccgccacatc gagcgggtca   3120
ccgagctgca agaactcttc ctcacgcgcg tcgggctcga catcggcaag gtgtgggtcg   3180
cggacgacgg cgccgcggtg gcggtctgga ccacgccgga gagcgtcgaa gcgggggcgg   3240
tgttcgccga gatcggcccg cgcatggccg agttgagcgg ttcccggctg gccgcgcagc   3300
```

```
aacagatgga aggcctcctg gcgccgcacc ggcccaagga gcccgcgtgg ttcctggcca    3360
ccgtcggcgt ctcgcccgac caccagggca agggtctggg cagcgccgtc gtgctcccg     3420 gagtggaggc ggccgagcgc gccggggtgc ccgccttcct ggagacctcc gcgcccgca     3480 acctcccctt ctacgagcgg ctcggcttca ccgtcaccgc cgacgtcgag gtgcccgaag    3540
gaccgcgcac ctggtgcatg acccgcaagc ccggtgcata agtagtactc tggagttcga    3600
aatgaccgac caagcgacgc ccaacctgcc atcacgatgg ccgcaataaa atatctttat    3660
tttcattaca tctgtgtgtt ggttttttgt gtgaatcgat agcgataaag atccgcgtat    3720
ggtgcactct cagtacaatc tgctctgatg ccgcatagtt aagccagccc gacacccgc     3780 caacacccgc tgacgcgccc tgacgggctt gtctgctccc ggcatccgct tacagacaag    3840
ctgtgaccgt ctccgggagc tgcatgtgtc agaggttttc accgtcatca ccgaaacgcg    3900
cgagacgaaa gggcctcgtg atacgcctat ttttataggt taatgtcatg ataataatgg    3960
tttcttagac gtcaggtggc acttttcggg gaaatgtgcg cggaacccct atttgtttat    4020
ttttctaaat acattcaaat atgtatccgc tcatgagaca ataaccctga taaatgcttc    4080
aataatattg aaaaggaag agtatgagta ttcaacattt ccgtgtcgcc cttattccct     4140
tttttgcggc attttgcctt cctgttttg ctcacccaga aacgctggtg aaagtaaaag     4200
atgctgaaga tcagttgggt gcacgagtgg gttacatcga actggatctc aacagcggta    4260
agatccttga gagttttcgc cccgaagaac gttttccaat gatgagcact tttaaagttc    4320
tgctatgtgg cgcggtatta tcccgtattg acgccgggca agagcaactc ggtcgccgca    4380
tacactattc tcagaatgac ttggttgagt actcaccagt cacagaaaag catcttacgg    4440
atggcatgac agtaagagaa ttatgcagtg ctgccataac catgagtgat aacactgcgg    4500
ccaacttact tctgacaacg atcggaggac cgaaggagct aaccgctttt ttgcacaaca    4560
tgggggatca tgtaactcgc cttgatcgtt gggaaccgga gctgaatgaa gccataccaa    4620
acgacgagcg tgacaccacg atgcctgtag caatggcaac aacgttgcgc aaactattaa    4680
ctggcgaact acttactcta gcttcccggc aacaattaat agactggatg gaggcggata    4740
aagttgcagg accacttctg cgctcggccc ttccggctgg ctggtttatt gctgataaat    4800
ctggagccgg tgagcgtggg tctcgcggta tcattgcagc actggggcca gatggtaagc    4860
cctcccgtat cgtagttatc tacacgacgg ggagtcaggc aactatggat gaacgaaata    4920
gacagatcgc tgagataggt gcctcactga ttaagcattg gtaactgtca gaccaagttt    4980
actcatatat actttagatt gatttaaaac ttcatttta atttaaaagg atctaggtga    5040 agatccttt tgataatctc atgaccaaaa tcccttaacg tgagttttcg ttccactgag    5100
cgtcagaccc cgtagaaaag atcaaaggat cttcttgaga tcctttttt ctgcgcgtaa    5160 tctgctgctt gcaaacaaaa aaaccaccgc taccagcggt ggtttgtttg ccggatcaag    5220
agctaccaac tcttttccg aaggtaactg gcttcagcag agcgcagata ccaaatactg     5280
ttcttctagt gtagccgtag ttaggccacc acttcaagaa ctctgtagca ccgcctacat    5340
acctcgctct gctaatcctg ttaccagtgg ctgctgccag tggcgataag tcgtgtctta    5400
ccgggttgga ctcaagacga tagttaccgg ataaggcgca gcggtcgggc tgaacggggg    5460
gttcgtgcac acagcccagc ttggagcgaa cgacctacac cgaactgaga tacctacagc    5520
gtgagctatg agaaagcgcc acgcttcccg aagggagaaa ggcggacagg tatccggtaa    5580
gcggcagggt cggaacagga gagcgcacga gggagcttcc agggggaaac gcctggtatc    5640
```

-continued

```
tttatagtcc tgtcgggttt cgccacctct gacttgagcg tcgatttttg tgatgctcgt    5700
caggggggcg gagcctatgg aaaaacgcca gcaacgcggc ctttttacgg ttcctggcct    5760
tttgctggcc ttttgctcac atggctcgac agatct                              5796
```

<210> SEQ ID NO 20
<211> LENGTH: 5627
<212> TYPE: DNA
<213> ORGANISM: Artificial Sequence
<220> FEATURE:
<223> OTHER INFORMATION: vector pMEX5

<400> SEQUENCE: 20

```
tctagactgt atgtacatac agagttcttg agtgatccct gtatgtacat acaggtcatc      60
atgaagtagt ctgtatgtac atacagagaa cttgagtgat ccctgtatgt acatacagtt     120
caagatactt agttctgtat gtacatacag agttcttgag tgatccctgt atgtacatac     180
agtctagagt tgacattgat tattgactag ttattaatag taatcaatta cggggtcatt     240
agttcatagc ccatatatgg agttccgcgt tacataactt acggtaaatg gcccgcctgg     300
ctgaccgccc aacgaccccc gcccattgac gtcaataatg acgtatgttc ccatagtaac     360
gccaataggg actttccatt gacgtcaatg ggtggagtat ttacggtaaa ctgcccactt     420
ggcagtacat caagtgtatc atatgccaag tacgccccct attgacgtca atgacggtaa     480
atggcccgcc tggcattatg cccagtacat gaccttatgg actttcctac ttggcagta     540 catctacgta ttagtcatcg ctattaccat ggtgatgcgg ttttggcagt acatcaatgg     600
gcgtggatag cggtttgact cacggggatt tccaagtctc caccccattg acgtcaatgg     660
gagtttgttt tggaaccaaa atcaacggga ctttccaaaa tgtcgtaaca actccgcccc     720
attgacgcaa atgggcggta ggcgtgtacg gtgggaggtc tatataagca gagctctccc     780
tatcagtgat agagatctcc ctatcagtga tagagatcgt cgacgagctc gtttagtgaa     840
ccgtcagatc gcctggagac gccatccacg ctgttttgac ctccatagaa gacaccggga     900
ccgatccagc ctccggctag cctcgagcca ccatggagac agacacactc ctgctatggg     960
tactgctgct ctgggttcca ggttccactg gtgatatcga ctataaagat gatgacgaca    1020
agggatcctg ccccagtcct ttggcttcat cgtgccactg ctgatcatgc tgttctgcta    1080
cggattcacc ctgcgtacgc tgtttaaggc ccacatgggg cagaagcacc gggccatgcg    1140
ggtcatcttt gctgtcgtcc tcatcttcct gctctgctgg ctgccctaca acctggtcct    1200
gctggcagac accctcatga ggaccaggt gatccaggag acctgtgagc gccgcaatca    1260
catcgaccgg gctctggatg ccaccgagat tctgggcatc cttcacagct gcctcaaccc    1320
cctcatctac gccttcattg gccagaagtt tcgccatgga ctcctcaaga ttctagctat    1380
acatggcttg atcagcaagg actccctgcc caaagacagc aggccttcct tgttggctc    1440 ttcttcaggg cacacttcca ctactctctg atagtcgacg cggccgcttc cctttagtga    1500
gggttaatgc ttcgagcaga catgataaga tacattgatg agtttggaca aaccacaact    1560
agaatgcagt gaaaaaaatg ctttatttgt gaaatttgtg atgctattgc tttatttgta    1620
accattataa gctgcaataa acaagttaac aacaacaatt gcattcattt tatgtttcag    1680 gttcagggg agatgtggga ggttttttaa agcaagtaaa acctctacaa atgtggtaaa    1740
atccgataag gatcgatccg ggctggcgta atagcgaaga ggcccgcacc gatcgccctt    1800
cccaacagtt gcgcagcctg aatggcgaat ggacgcgccc tgtagcggcg cattaagcgc    1860
ggcgggtgtg gtggttacgc gcagcgtgac cgctacactt gccagcgccc tagcgcccgc    1920
```

```
tcctttcgct ttcttcccct cctttctcgc cacgttcgcc ggctttcccc gtcaagctct    1980
aaatcggggg ctccctttag ggttccgatt tagtgcttta cggcacctcg accccaaaaa    2040
acttgattag ggtgatggtt cacgtagtgg gccatcgccc tgatagacgg ttttcgccc     2100
tttgacgttg gagtccacgt tctttaatag tggactcttg ttccaaactg gaacaacact    2160
caaccctatc tcggtctatt cttttgattt ataagggatt ttgccgattt cggcctattg    2220
gttaaaaaat gagctgattt aacaaaaatt taacgcgaat tttaacaaaa tattaacgct    2280
tacaatttcc tgatgcggta ttttctcctt acgcatctgt gcggtatttc acaccgcata    2340
cgcggatctg cgcagcacca tggcctgaaa taacctctga agaggaact tggttaggta     2400
ccttctgagg cggaaagaac cagctgtgga atgtgtgtca gttagggtgt ggaaagtccc    2460
caggctcccc agcaggcaga agtatgcaaa gcatgcatct caattagtca gcaaccaggt    2520
gtggaaagtc cccaggctcc ccagcaggca gaagtatgca aagcatgcat ctcaattagt    2580
cagcaaccat agtcccgccc ctaactccgc ccatcccgcc cctaactccg cccagttccg    2640
cccattctcc gccccatggc tgactaattt tttttattta tgcagaggcc gaggccgcct    2700
cggcctctga gctattccag aagtagtgag gaggcttttt tggaggccta ggcttttgca    2760
aaaagcttga ttcttctgac acaacagtct cgaacttaag gctagagcca ccatgaccga    2820
gtacaagccc acggtgcgcc tcgccacccg cgacgacgtc cccagggccg tacgcaccct    2880
cgccgccgcg ttcgccgact accccgccac gcgccacacc gtcgatccgg accgccacat    2940
cgagcgggtc accgagctgc aagaactctt cctcacgcgc gtcgggctcg acatcggcaa    3000
ggtgtgggtc gcggacgacg gcgccgcggt ggcggtctgg accacgccgg agagcgtcga    3060
agcggggcg gtgttcgccg agatcggccc gcgcatggcc gagttgagcg gttcccggct     3120
ggccgcgcag caacagatgg aaggcctcct ggcgccgcac cggcccaagg agcccgcgtg    3180
gttcctggcc accgtcggcg tctcgcccga ccaccagggc aagggtctgg gcagcgccgt    3240
cgtgctcccc ggagtggagg cggccgagcg cgccggggtg cccgccttcc tggagacctc    3300
cgcgccccgc aacctcccct tctacgagcg gctcggcttc accgtcaccg ccgacgtcga    3360
ggtgcccgaa ggaccgcgca cctggtgcat gacccgcaag cccggtgcat aagtagtact    3420
ctggagttcg aaatgaccga ccaagcgacg cccaacctgc catcacgatg gccgcaataa    3480
aatatcttta ttttcattac atctgtgtgt tggttttttg tgtgaatcga tagcgataaa    3540
gatccgcgta tggtgcactc tcagtacaat ctgctctgat gccgcatagt taagccagcc    3600
ccgacacccg ccaacacccg ctgacgcgcc ctgacgggct tgtctgctcc cggcatccgc    3660
ttacagacaa gctgtgaccg tctccgggag ctgcatgtgt cagaggtttt caccgtcatc    3720
accgaaacgc gcgagacgaa agggcctcgt gatacgccta ttttatagg ttaatgtcat     3780
gataataatg gttccttaga cgtcaggtgg cacttttcgg ggaaatgtgc gcggaacccc    3840
tatttgttta tttttctaaa tacattcaaa tatgtatccg ctcatgagac aataaccctg    3900
ataaatgctt caataatatt gaaaaaggaa gagtatgagt attcaacatt tccgtgtcgc    3960
ccttattccc tttttgcgg cattttgcct tcctgttttt gctcacccag aaacgctggt      4020
gaaagtaaaa gatgctgaag atcagttggg tgcacgagtg ggttacatcg aactggatct    4080
caacagcggt aagatccttg agagttttcg ccccgaagaa cgttttccaa tgatgagcac    4140
ttttaaagtt ctgctatgtg gcgcggtatt atcccgtatt gacgccgggc aagagcaact    4200
cggtcgccgc atacactatt ctcagaatga cttggttgag tactcaccag tcacagaaaa    4260
```

-continued

```
gcatcttacg gatggcatga cagtaagaga attatgcagt gctgccataa ccatgagtga    4320
taacactgcg gccaacttac ttctgacaac gatcggagga ccgaaggagc taaccgcttc    4380
tttgcacaac atgggggatc atgtaactcg ccttgatcgt tgggaaccgg agctgaatga    4440
agccatacca aacgacgagc gtgacaccac gatgcctgta gcaatggcaa caacgttgcg    4500
caaactatta actggcgaac tacttactct agcttcccgg caacaattaa tagactggat    4560
ggaggcggat aaagttgcag gaccacttct gcgctcggcc cttccggctg gctggtttat    4620
tgctgataaa tctggagccg gtgagcgtgg gtctcgcggt atcattgcag cactggggcc    4680
agatggtaag ccctcccgta tcgtagttat ctacacgacg gggagtcagg caactatgga    4740
tgaacgaaat agacagatcg ctgagatagg tgcctcactg attaagcatt ggtaactgtc    4800
agaccaagtt tactcatata tactttagat tgatttaaaa cttcattttt aatttaaaag    4860
gatctaggtg aagatccttt ttgataatct catgaccaaa atcccttaac gtgagttttc    4920
gttccactga gcgtcagacc ccgtagaaaa gatcaaagga tcttcttgag atcctttttt    4980
tctgcgcgta atctgctgct tgcaaacaaa aaaaccaccg ctaccagcgg tggtttgttt    5040
gccggatcaa gagctaccaa ctcttttttcc gaaggtaact ggcttcagca gagcgcagat    5100
accaaatact gttcttctag tgtagccgta gttaggccac cacttcaaga actctgtagc    5160
accgcctaca tacctcgctc tgctaatcct gttaccagtg gctgctgcca gtggcgataa    5220
gtcgtgtctt accgggttgg actcaagacg atagttaccg gataaggcgc agcggtcggg    5280
ctgaacgggg ggttcgtgca cacagcccag cttggagcga acgacctaca ccgaactgag    5340
atacctacag cgtgagctat gagaaagcgc cacgcttccc gaagggagaa aggcggacag    5400
gtatccggta agcggcaggg tcggaacagg agagcgcacg agggagcttc caggggggaaa    5460 cgcctggtat ctttatagtc ctgtcgggtt tcgccacctc tgacttgagc gtcgattttt    5520
gtgatgctcg tcaggggggc ggagcctatg gaaaaacgcc agcaacgcgg cctttttacg    5580
gttcctggcc ttttgctggc cttttgctca catggctcga cagatct                 5627
```